US011400072B2

(12) United States Patent
Mantzoros

(10) Patent No.: US 11,400,072 B2
(45) Date of Patent: *Aug. 2, 2022

(54) METHODS FOR THE TREATMENT OF NONALCOHOLIC FATTY LIVER DISEASE AND/OR LIPODYSTROPHY

(71) Applicant: Coherus Biosciences, Inc., Redwood City, CA (US)

(72) Inventor: Christos Mantzoros, Watertown, MA (US)

(73) Assignee: Coherus Biosciences, Inc., Redwood City, CA (US)

( * ) Notice: Subject to any disclaimer, the term of this patent is extended or adjusted under 35 U.S.C. 154(b) by 85 days.

This patent is subject to a terminal disclaimer.

(21) Appl. No.: 16/911,721

(22) Filed: Jun. 25, 2020

(65) Prior Publication Data

US 2020/0383945 A1 Dec. 10, 2020

Related U.S. Application Data

(63) Continuation of application No. 16/744,433, filed on Jan. 16, 2020, now Pat. No. 10,772,865, which is a continuation of application No. 15/062,331, filed on Mar. 7, 2016, now Pat. No. 10,555,929.

(60) Provisional application No. 62/130,488, filed on Mar. 9, 2015.

(51) Int. Cl.
*A61K 31/355* (2006.01)
*A61K 31/4709* (2006.01)

(52) U.S. Cl.
CPC ........ *A61K 31/355* (2013.01); *A61K 31/4709* (2013.01)

(58) Field of Classification Search
CPC .......................... A61K 31/355; A61K 31/4709
USPC ........................................................ 514/312
See application file for complete search history.

(56) References Cited

U.S. PATENT DOCUMENTS

| 4,166,452 A | 9/1979 | Generales, Jr. |
| 4,256,108 A | 3/1981 | Theeuwes |
| 4,265,874 A | 5/1981 | Bonsen et al. |
| 4,917,885 A | 4/1990 | Chiba et al. |
| 5,424,286 A | 6/1995 | Eng |
| 5,431,917 A | 6/1995 | Yamamoto et al. |
| 5,462,928 A | 10/1995 | Bachovchin et al. |
| 5,595,898 A | 1/1997 | Robinson et al. |
| 5,939,560 A | 8/1999 | Jenkins et al. |
| 6,011,155 A | 1/2000 | Villhauer |
| 6,040,145 A | 3/2000 | Huber et al. |
| 6,100,234 A | 8/2000 | Huber et al. |
| 6,107,317 A | 8/2000 | Villhauer |
| 6,110,949 A | 8/2000 | Villhauer |
| 6,124,305 A | 9/2000 | Villhauer |
| 6,166,063 A | 12/2000 | Villhauer |
| 6,172,081 B1 | 1/2001 | Damon |
| 6,200,995 B1 | 3/2001 | De la Brouse-Elwood et al. |
| 6,201,132 B1 | 3/2001 | Jenkins et al. |
| 6,242,422 B1 | 6/2001 | Karanewsky et al. |
| 6,303,661 B1 | 10/2001 | Demuth et al. |
| 6,319,893 B1 | 11/2001 | Demuth et al. |
| 6,380,398 B2 | 4/2002 | Kanstrup et al. |
| 6,395,767 B2 | 5/2002 | Robi et al. |
| 6,407,213 B1 | 6/2002 | Carter et al. |
| 6,413,463 B1 | 7/2002 | Yamamoto et al. |
| 6,432,969 B1 | 8/2002 | Villhauer |
| 6,573,287 B2 | 6/2003 | Sulsky et al. |
| 6,583,157 B2 | 6/2003 | McGee et al. |
| 6,617,340 B1 | 9/2003 | Villhauer |
| 6,645,995 B2 | 11/2003 | Kanstrup et al. |
| 6,649,180 B1 | 11/2003 | Matsuura et al. |
| 6,653,332 B2 | 11/2003 | Jaen et al. |
| 6,699,871 B2 | 3/2004 | Edmondsun et al. |
| 6,706,742 B2 | 3/2004 | De Nanteuil et al. |
| 6,710,040 B1 | 3/2004 | Hulin et al. |
| 6,716,843 B2 | 4/2004 | De Nanteuil et al. |
| 6,727,261 B2 | 4/2004 | Gobbi et al. |
| 6,770,648 B2 | 8/2004 | McGee et al. |
| 6,800,650 B2 | 10/2004 | Boehringer et al. |
| 6,803,357 B1 | 10/2004 | Bachovchin et al. |
| 6,812,350 B2 | 11/2004 | Hulin |
| 6,825,169 B1 | 11/2004 | Bachovchin et al. |
| 6,844,316 B2 | 1/2005 | Niestroj et al. |
| 6,849,622 B2 | 2/2005 | Yasuda et al. |
| 6,861,440 B2 | 3/2005 | Boehringer et al. |
| 6,867,205 B2 | 3/2005 | Boehringer et al. |
| 6,869,947 B2 | 3/2005 | Kanstrup et al. |
| 6,890,898 B2 | 5/2005 | Bachovchin et al. |

(Continued)

FOREIGN PATENT DOCUMENTS

| CA | 2123128 | 5/1993 |
| CA | 2289124 | 11/1998 |

(Continued)

OTHER PUBLICATIONS

Bacioglu et al., "Neurofilament Light Chain in Blood and CSF as Marker of Disease Progression in Mouse Models and in Neurodegenerative Diseases" Neuron 91: 56-66, 2016.

(Continued)

*Primary Examiner* — Yevgeny Valenrod
(74) *Attorney, Agent, or Firm* — Fish & Richardson P.C.

(57) ABSTRACT

The present invention relates to methods for treating a disease associated with insulin resistance selected from a nonalcoholic fatty liver disease (NAFLD) and its sequelae, a lipodystrophic syndrome or a combination thereof with the selective PPARγ agonist, INT131 and optionally vitamin E or compositions thereof. NAFLDs that may be treated with methods and compositions of the present invention include, but are not limited to, simple nonalcoholic fatty liver and nonalcoholic steatohepatitis (NASH). Lipodystrophic syndromes that may be treated with the methods and compositions of the present invention include, but are not limited to, generalized lipodystrophy including congenital generalized lipodystrophy and acquired generalized lipodystrophy and/or partial lipodystrophy, including congenital partial lipodystrophy and acquired partial lipodystrophy, all of which may or may not include hyperlipidemia and/or hyperglycemia and may or may not include NAFLD.

27 Claims, No Drawings

(56) References Cited

U.S. PATENT DOCUMENTS

| | | |
|---|---|---|
| 6,890,905 B2 | 5/2005 | Demuth et al. |
| 6,902,744 B1 | 6/2005 | Kolterman et al. |
| 6,911,467 B2 | 6/2005 | Evans |
| 7,026,316 B2 | 4/2006 | Ashton et al. |
| 7,034,039 B2 | 4/2006 | Oi et al. |
| 7,041,691 B1 | 5/2006 | McGee et al. |
| 7,053,055 B2 | 5/2006 | Demuth et al. |
| 7,060,269 B1 | 6/2006 | Baca et al. |
| 7,060,722 B2 | 6/2006 | Kitajima et al. |
| 7,074,794 B2 | 7/2006 | Kitajima et al. |
| 7,078,281 B2 | 7/2006 | Tanaka et al. |
| 7,078,397 B2 | 7/2006 | Arch et al. |
| 7,084,120 B2 | 8/2006 | Demuth et al. |
| 7,098,239 B2 | 8/2006 | Edmondsun et al. |
| 7,101,871 B2 | 9/2006 | Biftu et al. |
| 7,109,192 B2 | 9/2006 | Hauel et al. |
| 7,115,650 B1 | 10/2006 | Broqua |
| 7,122,555 B2 | 10/2006 | Boehringer et al. |
| 7,125,863 B2 | 10/2006 | Evans et al. |
| 7,125,873 B2 | 10/2006 | Edmondsun et al. |
| 7,132,443 B2 | 11/2006 | Haffner et al. |
| 7,144,886 B2 | 12/2006 | Evans et al. |
| 7,157,490 B2 | 1/2007 | Colandrea et al. |
| 7,166,579 B2 | 1/2007 | Demuth et al. |
| 7,169,806 B2 | 1/2007 | Evans |
| 7,169,926 B1 | 1/2007 | Burgess et al. |
| 7,179,809 B2 | 2/2007 | Eckhardt et al. |
| 7,183,280 B2 | 2/2007 | Himmelsbach et al. |
| 7,183,290 B2 | 2/2007 | Haffner et al. |
| 7,186,731 B2 | 3/2007 | Shima et al. |
| 7,186,846 B2 | 3/2007 | Sharma et al. |
| 7,189,728 B2 | 3/2007 | Evans et al. |
| 7,192,952 B2 | 3/2007 | Kanstrup et al. |
| 7,196,201 B2 | 3/2007 | Haffner et al. |
| 7,205,323 B2 | 4/2007 | Thomas et al. |
| 7,205,409 B2 | 4/2007 | Pei et al. |
| 7,208,498 B2 | 4/2007 | Mathvink et al. |
| 7,217,711 B2 | 5/2007 | Eckhardt et al. |
| 7,223,573 B2 | 5/2007 | Patel et al. |
| 7,223,761 B2 | 5/2007 | Kurk et al. |
| 7,229,969 B2 | 6/2007 | Ansorge et al. |
| 7,230,002 B2 | 6/2007 | Thomas et al. |
| 7,230,074 B2 | 6/2007 | Bachovchin et al. |
| 7,235,538 B2 | 6/2007 | Kanstrup et al. |
| 7,236,683 B2 | 6/2007 | Quan |
| 7,238,720 B2 | 7/2007 | Yasuda et al. |
| 7,238,724 B2 | 7/2007 | Madar et al. |
| 7,241,756 B2 | 7/2007 | Arch et al. |
| 7,253,172 B2 | 8/2007 | Brockunier et al. |
| 7,297,761 B2 | 11/2007 | Beeley et al. |
| 7,368,427 B1 | 5/2008 | Dong et al. |
| 7,601,841 B2 | 10/2009 | McGee et al. |
| 7,626,033 B2 | 12/2009 | McGee et al. |
| 7,754,447 B2 | 7/2010 | Glover et al. |
| 7,939,551 B2 | 5/2011 | Jaen et al. |
| 7,960,408 B2 | 6/2011 | McGee et al. |
| 7,968,567 B2 | 6/2011 | McGee et al. |
| 8,003,665 B2 | 8/2011 | Kurk et al. |
| 8,202,893 B2 | 6/2012 | Makriyannis |
| RE44,512 E | 10/2013 | Glover et al. |
| 9,061,020 B2 | 6/2015 | Weinsten |
| 9,267,164 B2 | 2/2016 | O'Keefe |
| 9,675,603 B2 | 6/2017 | Lee et al. |
| 9,872,844 B2 | 1/2018 | Zemel et al. |
| 10,555,929 B2 * | 2/2020 | Mantzoros .......... A61K 31/4709 |
| 10,772,865 B2 * | 9/2020 | Mantzoros ............... A61P 1/16 |
| 2001/0020006 A1 | 9/2001 | Demuth et al. |
| 2002/0006899 A1 | 1/2002 | Posipilik |
| 2002/0019411 A1 | 2/2002 | Robl et al. |
| 2002/0049164 A1 | 4/2002 | Demuth et al. |
| 2002/0061839 A1 | 5/2002 | Scharpe et al. |
| 2002/0065239 A1 | 5/2002 | Caplan et al. |
| 2002/0071838 A1 | 6/2002 | Demuth et al. |
| 2002/0103384 A1 | 8/2002 | Kanstrup et al. |
| 2002/0110560 A1 | 8/2002 | Demuth et al. |
| 2002/0161001 A1 | 10/2002 | Kanstrup et al. |
| 2002/0165164 A1 | 11/2002 | Demuth et al. |
| 2002/0169185 A1 | 11/2002 | McGee et al. |
| 2002/0183367 A1 | 12/2002 | Sulsky et al. |
| 2002/0198205 A1 | 12/2002 | Himmelsbach et al. |
| 2002/0198242 A1 | 12/2002 | Demuth et al. |
| 2003/0060494 A1 | 3/2003 | Yasuda et al. |
| 2003/0078247 A1 | 4/2003 | De Nanteuil et al. |
| 2003/0087950 A1 | 5/2003 | De Nanteuil et al. |
| 2003/0092630 A2 | 5/2003 | Demuth et al. |
| 2003/0096857 A1 | 5/2003 | Evans |
| 2003/0100563 A1 | 5/2003 | Edmondsun et al. |
| 2003/0105077 A1 | 6/2003 | Kanstrup et al. |
| 2003/0119738 A1 | 6/2003 | Niestroj et al. |
| 2003/0119750 A1 | 6/2003 | Demuth et al. |
| 2003/0125304 A1 | 7/2003 | Demuth et al. |
| 2003/0130199 A1 | 7/2003 | von Hoersten et al. |
| 2003/0130281 A1 | 7/2003 | Boehringer et al. |
| 2003/0134802 A1 | 7/2003 | Demuth et al. |
| 2003/0136390 A1 | 7/2003 | McGee et al. |
| 2003/0139390 A1 | 7/2003 | McGee et al. |
| 2003/0149071 A1 | 8/2003 | Gobbi et al. |
| 2003/0162820 A1 | 8/2003 | Demuth et al. |
| 2003/0166578 A1 | 9/2003 | Arch et al. |
| 2003/0195188 A1 | 10/2003 | Boehringer et al. |
| 2003/0199528 A1 | 10/2003 | Kanstrup et al. |
| 2003/0216382 A1 | 11/2003 | Boehringer et al. |
| 2003/0216450 A1 | 11/2003 | Evans et al. |
| 2003/0225102 A1 | 12/2003 | Sankaranarayanan |
| 2003/0232788 A1 | 12/2003 | Karanewsky et al. |
| 2004/0034014 A1 | 2/2004 | Kanstrup et al. |
| 2004/0063935 A1 | 4/2004 | Yasuda et al. |
| 2004/0072892 A1 | 4/2004 | Fukushima et al. |
| 2004/0077645 A1 | 4/2004 | Himmelsbach et al. |
| 2004/0082497 A1 | 4/2004 | Evans et al. |
| 2004/0082570 A1 | 4/2004 | Yoshikawa et al. |
| 2004/0087587 A1 | 5/2004 | Himmelsbach et al. |
| 2004/0097510 A1 | 5/2004 | Himmelsbach et al. |
| 2004/0106655 A1 | 6/2004 | Kitajima et al. |
| 2004/0106656 A1 | 6/2004 | Ashton et al. |
| 2004/0106802 A1 | 6/2004 | Sankaranarayanan |
| 2004/0110817 A1 | 6/2004 | Hulin |
| 2004/0116328 A1 | 6/2004 | Yoshikawa et al. |
| 2004/0121964 A1 | 6/2004 | Madar et al. |
| 2004/0138214 A1 | 7/2004 | Himmelsbach et al. |
| 2004/0138215 A1 | 7/2004 | Eckhardt et al. |
| 2004/0147434 A1 | 7/2004 | Ansorge et al. |
| 2004/0152745 A1 | 8/2004 | Jackson et al. |
| 2004/0167133 A1 | 8/2004 | Edmondsun et al. |
| 2004/0167341 A1 | 8/2004 | Haffner et al. |
| 2004/0171555 A1 | 9/2004 | Demuth et al. |
| 2004/0171848 A1 | 9/2004 | Haffner et al. |
| 2004/0176406 A1 | 9/2004 | Gobbi et al. |
| 2004/0176428 A1 | 9/2004 | Edmondsun et al. |
| 2004/0180925 A1 | 9/2004 | Matsuno |
| 2004/0186153 A1 | 9/2004 | Yasuda et al. |
| 2004/0209891 A1 | 10/2004 | Broqua et al. |
| 2004/0224995 A1 | 11/2004 | Simpkins et al. |
| 2004/0229820 A1 | 11/2004 | Bachovchin et al. |
| 2004/0229848 A1 | 11/2004 | Demuth et al. |
| 2004/0229926 A1 | 11/2004 | Yasuda et al. |
| 2004/0235752 A1 | 11/2004 | Pitt et al. |
| 2004/0236102 A1 | 11/2004 | Brockunier et al. |
| 2004/0242566 A1 | 12/2004 | Feng et al. |
| 2004/0242568 A1 | 12/2004 | Feng et al. |
| 2004/0242636 A1 | 12/2004 | Haffner et al. |
| 2004/0242898 A1 | 12/2004 | Hulin |
| 2004/0254226 A1 | 12/2004 | Feng et al. |
| 2004/0259843 A1 | 12/2004 | Madar et al. |
| 2004/0259870 A1 | 12/2004 | Feng et al. |
| 2004/0259883 A1 | 12/2004 | Sakashita et al. |
| 2004/0259902 A1 | 12/2004 | Boehringer et al. |
| 2004/0259903 A1 | 12/2004 | Boehringer et al. |
| 2005/0004117 A1 | 1/2005 | Feng et al. |
| 2005/0004205 A1 | 1/2005 | Evans et al. |
| 2005/0026921 A1 | 2/2005 | Eckhardt et al. |
| 2005/0032804 A1 | 2/2005 | Cypes et al. |
| 2005/0038020 A1 | 2/2005 | Hamann et al. |
| 2005/0043292 A1 | 2/2005 | Parker et al. |

(56) References Cited

U.S. PATENT DOCUMENTS

| | | |
|---|---|---|
| 2005/0043299 A1 | 2/2005 | Evans et al. |
| 2005/0059716 A1 | 3/2005 | Wagner et al. |
| 2005/0059724 A1 | 3/2005 | Schoenafinger et al. |
| 2005/0065144 A1 | 3/2005 | Feng et al. |
| 2005/0065145 A1 | 3/2005 | Cao et al. |
| 2005/0065148 A1 | 3/2005 | Feng et al. |
| 2005/0065183 A1 | 3/2005 | Nandi et al. |
| 2005/0070530 A1 | 3/2005 | Feng et al. |
| 2005/0070531 A1 | 3/2005 | Feng et al. |
| 2005/0070535 A1 | 3/2005 | Feng et al. |
| 2005/0070706 A1 | 3/2005 | Feng et al. |
| 2005/0070719 A1 | 3/2005 | Belyakov et al. |
| 2005/0075330 A1 | 4/2005 | Feng et al. |
| 2005/0090539 A1 | 4/2005 | Vu et al. |
| 2005/0096348 A1 | 5/2005 | Boehringer et al. |
| 2005/0107309 A1 | 5/2005 | Demuth et al. |
| 2005/0107390 A1 | 5/2005 | Brockunier et al. |
| 2005/0113310 A1 | 5/2005 | Striggow et al. |
| 2005/0130981 A1 | 6/2005 | Aranyl et al. |
| 2005/0130985 A1 | 6/2005 | Himmelsbach et al. |
| 2005/0131019 A1 | 6/2005 | Pei et al. |
| 2005/0137224 A1 | 6/2005 | Shima et al. |
| 2005/0143377 A1 | 6/2005 | Himmelsbach et al. |
| 2005/0143405 A1 | 6/2005 | Boehringer et al. |
| 2005/0143416 A1 | 6/2005 | Kurk et al. |
| 2005/0165989 A1 | 7/2005 | Kim |
| 2005/0171093 A1 | 8/2005 | Eckhardt et al. |
| 2005/0176771 A1 | 8/2005 | Hayawaka |
| 2005/0187227 A1 | 8/2005 | Himmelsbach et al. |
| 2005/0192324 A1 | 9/2005 | Thomas et al. |
| 2005/0203027 A1 | 9/2005 | Bachovchin et al. |
| 2005/0203031 A1 | 9/2005 | Evans |
| 2005/0203095 A1 | 9/2005 | Eckhardt et al. |
| 2005/0209159 A1 | 9/2005 | Demuth et al. |
| 2005/0209249 A1 | 9/2005 | Akritopoulou-Zanze et al. |
| 2005/0215603 A1 | 9/2005 | Akritopoulou-Zanze et al. |
| 2005/0215784 A1 | 9/2005 | Madar et al. |
| 2005/0215882 A1 | 9/2005 | Chenevert et al. |
| 2005/0222140 A1 | 10/2005 | Colandrea et al. |
| 2005/0222222 A1 | 10/2005 | Jiaang et al. |
| 2005/0222242 A1 | 10/2005 | Sharma et al. |
| 2005/0233978 A1 | 10/2005 | Niestroj et al. |
| 2005/0234108 A1 | 10/2005 | Himmelsbach et al. |
| 2005/0234235 A1 | 10/2005 | Eckhardt et al. |
| 2005/0245538 A1 | 11/2005 | Kitajima et al. |
| 2005/0250820 A1 | 11/2005 | Chen |
| 2005/0254167 A1 | 11/2005 | Matsutani et al. |
| 2005/0260712 A1 | 11/2005 | Politino et al. |
| 2005/0260732 A1 | 11/2005 | Hiramatsu et al. |
| 2005/0261271 A1 | 11/2005 | Feng et al. |
| 2005/0272652 A1 | 12/2005 | Gault et al. |
| 2005/0272765 A1 | 12/2005 | Feng et al. |
| 2006/0004074 A1 | 1/2006 | Eckhardt et al. |
| 2006/0014764 A1 | 1/2006 | Feng et al. |
| 2006/0014953 A1 | 1/2006 | Kim |
| 2006/0023870 A1 | 2/2006 | Stenmark |
| 2006/0027022 A1 | 2/2006 | Flora et al. |
| 2006/0039974 A1 | 2/2006 | Akiyama et al. |
| 2006/0040963 A1 | 2/2006 | Mathvink et al. |
| 2006/0046978 A1 | 3/2006 | Pierau et al. |
| 2006/0052382 A1 | 3/2006 | Duffy et al. |
| 2006/0058323 A1 | 3/2006 | Eckhardt et al. |
| 2006/0069116 A1 | 3/2006 | Ashton et al. |
| 2006/0074058 A1 | 4/2006 | Holmes et al. |
| 2006/0074087 A1 | 4/2006 | Ashton et al. |
| 2006/0079541 A1 | 4/2006 | Langkopf |
| 2006/0111336 A1 | 5/2006 | Duffy et al. |
| 2006/0111428 A1 | 5/2006 | Wang |
| 2006/0116393 A1 | 6/2006 | Boehringer et al. |
| 2006/0135512 A1 | 6/2006 | Boehringer et al. |
| 2006/0135561 A1 | 6/2006 | Boehringer et al. |
| 2006/0135767 A1 | 6/2006 | Feng et al. |
| 2006/0142585 A1 | 6/2006 | Thomas et al. |
| 2006/0153940 A1 | 7/2006 | Prous |
| 2006/0154866 A1 | 7/2006 | Chu et al. |
| 2006/0173056 A1 | 8/2006 | Kitajima et al. |
| 2006/0205675 A1 | 9/2006 | Arch et al. |
| 2006/0205711 A1 | 9/2006 | Himmelsbach et al. |
| 2006/0211682 A1 | 9/2006 | Liang et al. |
| 2006/0217428 A1 | 9/2006 | Abrecht et al. |
| 2006/0223870 A1 | 10/2006 | Doken |
| 2006/0229286 A1 | 10/2006 | Kakigami et al. |
| 2006/0247226 A1 | 11/2006 | Himmelsbach et al. |
| 2006/0258646 A1 | 11/2006 | Biftu et al. |
| 2006/0259621 A1 | 11/2006 | Ranganathan et al. |
| 2006/0264400 A1 | 11/2006 | Campbell et al. |
| 2006/0264401 A1 | 11/2006 | Campbell et al. |
| 2006/0264433 A1 | 11/2006 | Backes et al. |
| 2006/0264457 A1 | 11/2006 | Devasthale et al. |
| 2006/0264481 A1 | 11/2006 | Chen |
| 2006/0270701 A1 | 11/2006 | Kroth et al. |
| 2006/0270722 A1 | 11/2006 | Thornberry et al. |
| 2006/0276410 A1 | 12/2006 | Campbell et al. |
| 2006/0276487 A1 | 12/2006 | Aranyl et al. |
| 2006/0281727 A1 | 12/2006 | Ashton et al. |
| 2006/0281796 A1 | 12/2006 | Edmondsun et al. |
| 2006/0293297 A1 | 12/2006 | Fukushima et al. |
| 2007/0016750 A1 | 1/2007 | Suzuki |
| 2007/0021477 A1 | 1/2007 | Edmondsun et al. |
| 2007/0049596 A1 | 3/2007 | Pei et al. |
| 2007/0049619 A1 | 3/2007 | Akahoshi et al. |
| 2007/0060547 A1 | 3/2007 | Campbell et al. |
| 2007/0072803 A1 | 3/2007 | Chu et al. |
| 2007/0072804 A1 | 3/2007 | Chu et al. |
| 2007/0072810 A1 | 3/2007 | Asakawa |
| 2007/0082908 A1 | 4/2007 | Nakahira et al. |
| 2007/0082932 A1 | 4/2007 | Jiaang et al. |
| 2007/0093492 A1 | 4/2007 | Jiaang et al. |
| 2007/0098781 A1 | 5/2007 | Loeffler et al. |
| 2007/0105890 A1 | 5/2007 | Nakahira et al. |
| 2007/0112059 A1 | 5/2007 | Fukushima et al. |
| 2007/0123579 A1 | 5/2007 | Sharma et al. |
| 2007/0142383 A1 | 6/2007 | Eckhardt et al. |
| 2007/0142436 A1 | 6/2007 | Bubendorf et al. |
| 2007/0149451 A1 | 6/2007 | Holmes et al. |
| 2007/0172525 A1 | 7/2007 | Sesha |
| 2007/0185061 A1 | 8/2007 | Campbell et al. |
| 2007/0239536 A1 | 12/2007 | Bollapragada |
| 2007/0293536 A1 | 12/2007 | Kruk |
| 2008/0020046 A1 | 1/2008 | Dawson |
| 2008/0132555 A1 | 6/2008 | Gant |
| 2009/0074862 A1 | 3/2009 | Schioppi |
| 2010/0087481 A1 | 4/2010 | Lee |
| 2010/0184783 A1 | 7/2010 | Raud et al. |
| 2011/0034380 A1 | 2/2011 | Lanfear et al. |
| 2011/0112097 A1 | 5/2011 | Jaehne et al. |
| 2012/0137162 A1 | 5/2012 | Huang et al. |
| 2012/0322719 A1 | 12/2012 | Pavlov et al. |
| 2013/0243865 A1 | 9/2013 | Lee |
| 2013/0245024 A1 | 9/2013 | Lanfear et al. |
| 2014/0107154 A1 | 4/2014 | Filippi |
| 2014/0213612 A1 | 7/2014 | Weinsten |
| 2014/0303018 A1 | 10/2014 | Nikrad et al. |
| 2014/0336113 A1 | 11/2014 | Hawiger et al. |
| 2014/0369965 A1 | 12/2014 | Herranz et al. |
| 2014/0377222 A1 | 12/2014 | Huang et al. |
| 2015/0023878 A1 | 1/2015 | Gredes et al. |
| 2015/0051143 A1 | 2/2015 | Harada et al. |
| 2015/0051261 A1 | 2/2015 | Zhao et al. |
| 2015/0224140 A1 | 8/2015 | Komorowski |
| 2015/0238478 A1 | 8/2015 | Weinsten |
| 2016/0146715 A1 | 5/2016 | Shim et al. |
| 2016/0260398 A1 | 9/2016 | Mantzoros |
| 2016/0287608 A1 | 10/2016 | Carnazza |
| 2017/0143687 A1 | 5/2017 | Weinsten |
| 2017/0273969 A1 | 9/2017 | Lee |
| 2018/0140219 A1 | 5/2018 | Yin et al. |
| 2019/0167660 A1 | 6/2019 | Lanfear |
| 2019/0224186 A1 | 7/2019 | Finck |
| 2019/0298708 A1 | 10/2019 | Jain |
| 2019/0350918 A1 | 11/2019 | Finck |
| 2020/0147036 A1 | 5/2020 | Mantzoros |

(56) References Cited

U.S. PATENT DOCUMENTS

2021/0283121 A1 9/2021 Finck et al.
2021/0379049 A1 12/2021 Mantzoros

FOREIGN PATENT DOCUMENTS

| | | |
|---|---|---|
| CA | 2289125 | 11/1998 |
| CA | 2339537 | 3/2000 |
| CA | 2353462 | 6/2000 |
| CA | 2433090 | 7/2002 |
| CA | 2466870 | 6/2003 |
| CN | 1440383 | 9/2003 |
| DE | 296075 | 11/1991 |
| DE | 19616486 | 10/1997 |
| DE | 19823831 | 12/1999 |
| DE | 19828113 | 1/2000 |
| DE | 19834591 | 2/2000 |
| DE | 10143840 | 3/2003 |
| DE | 10238243 | 3/2004 |
| DE | 10238470 | 3/2004 |
| DE | 10238477 | 3/2004 |
| DE | 10251927 | 5/2004 |
| DE | 10256264 | 6/2004 |
| DE | 10327439 | 1/2005 |
| DE | 10333935 | 2/2005 |
| EP | 0528858 | 3/1993 |
| EP | 0610317 | 8/1994 |
| EP | 0641347 | 3/1995 |
| EP | 0731789 | 9/1996 |
| EP | 0975359 | 2/2000 |
| EP | 0980249 | 2/2000 |
| EP | 0995440 | 4/2000 |
| EP | 1043328 | 10/2000 |
| EP | 1050540 | 11/2000 |
| EP | 1082314 | 3/2001 |
| EP | 1104293 | 6/2001 |
| EP | 1123272 | 8/2001 |
| EP | 1137635 | 10/2001 |
| EP | 1192137 | 4/2002 |
| EP | 1215207 | 6/2002 |
| EP | 1228061 | 8/2002 |
| EP | 1245568 | 10/2002 |
| EP | 1248604 | 10/2002 |
| EP | 1254113 | 11/2002 |
| EP | 1258476 | 11/2002 |
| EP | 1261586 | 12/2002 |
| EP | 1280797 | 2/2003 |
| EP | 1282600 | 2/2003 |
| EP | 1296974 | 4/2003 |
| EP | 1301187 | 4/2003 |
| EP | 1304327 | 4/2003 |
| EP | 1333025 | 8/2003 |
| EP | 1338592 | 8/2003 |
| EP | 1354882 | 10/2003 |
| EP | 1355886 | 10/2003 |
| EP | 1377288 | 1/2004 |
| EP | 1385508 | 2/2004 |
| EP | 1399154 | 3/2004 |
| EP | 1399420 | 3/2004 |
| EP | 1399433 | 3/2004 |
| EP | 1399469 | 3/2004 |
| EP | 1399470 | 3/2004 |
| EP | 1399471 | 3/2004 |
| EP | 1404675 | 4/2004 |
| EP | 1406622 | 4/2004 |
| EP | 1406872 | 4/2004 |
| EP | 1406873 | 4/2004 |
| EP | 1412357 | 4/2004 |
| EP | 1426366 | 6/2004 |
| EP | 1441719 | 8/2004 |
| EP | 1442049 | 8/2004 |
| EP | 1446116 | 8/2004 |
| EP | 1450794 | 9/2004 |
| EP | 1461337 | 9/2004 |
| EP | 1463727 | 10/2004 |
| EP | 1465891 | 10/2004 |
| EP | 1469873 | 10/2004 |
| EP | 147643 5 | 11/2004 |
| EP | 1476429 | 11/2004 |
| EP | 1480961 | 12/2004 |
| EP | 1489088 | 12/2004 |
| EP | 1490335 | 12/2004 |
| EP | 1492777 | 1/2005 |
| EP | 1513808 | 3/2005 |
| EP | 1517907 | 3/2005 |
| EP | 1296967 | 5/2006 |
| EP | 1664278 | 6/2006 |
| EP | 1738754 | 1/2007 |
| EP | 1782828 | 5/2007 |
| EP | 1905450 | 4/2008 |
| EP | 1677797 | 2/2012 |
| EP | 3267994 | 1/2018 |
| EP | 2618827 | 2/2021 |
| FR | 2822826 | 10/2002 |
| FR | 2824825 | 11/2002 |
| JP | 2000191616 | 7/2000 |
| JP | 2000/256208 | 9/2000 |
| JP | 2000511559 | 9/2000 |
| JP | 2000327689 | 11/2000 |
| JP | 2007/507537 | 3/2001 |
| JP | 2001510442 | 7/2001 |
| JP | 2002516318 | 6/2002 |
| JP | 2002517401 | 6/2002 |
| JP | 2002527504 | 8/2002 |
| JP | 2002265439 | 9/2002 |
| JP | 2002531541 | 9/2002 |
| JP | 2002531547 | 9/2002 |
| JP | 2002356471 | 12/2002 |
| JP | 2002356472 | 12/2002 |
| JP | 2002363157 | 12/2002 |
| JP | 2003520849 | 7/2003 |
| JP | 2003238566 | 8/2003 |
| JP | 2003524591 | 8/2003 |
| JP | 2003300977 | 10/2003 |
| JP | 2003531118 | 10/2003 |
| JP | 2003531191 | 10/2003 |
| JP | 2003531204 | 10/2003 |
| JP | 2003327532 | 11/2003 |
| JP | 2003535034 | 11/2003 |
| JP | 2003535898 | 12/2003 |
| JP | 2004002367 | 1/2004 |
| JP | 2004002368 | 1/2004 |
| JP | 2004026678 | 1/2004 |
| JP | 2004026820 | 1/2004 |
| JP | 2004035574 | 2/2004 |
| JP | 2004043429 | 2/2004 |
| JP | 2004503531 | 2/2004 |
| JP | 2004521149 | 7/2004 |
| JP | 2004522786 | 7/2004 |
| JP | 2004525179 | 8/2004 |
| JP | 2004525929 | 8/2004 |
| JP | 2004244412 | 9/2004 |
| JP | 2004530729 | 10/2004 |
| JP | 2004532220 | 10/2004 |
| JP | 2004315496 | 11/2004 |
| JP | 2004534815 | 11/2004 |
| JP | 2004534836 | 11/2004 |
| JP | 2004535433 | 11/2004 |
| JP | 2004535445 | 11/2004 |
| JP | 2004536115 | 12/2004 |
| JP | 2005023038 | 1/2005 |
| JP | 2005500308 | 1/2005 |
| JP | 2005500321 | 1/2005 |
| JP | 2005502624 | 1/2005 |
| JP | 2005505531 | 2/2005 |
| JP | 2005507261 | 3/2005 |
| JP | 2010/265216 | 11/2010 |
| JP | 2016506956 | 3/2016 |
| JP | 2018507914 | 3/2018 |
| MX | MX06003313 | 6/2006 |
| WO | WO 1991/016339 | 10/1991 |
| WO | WO 1993/008259 | 4/1993 |
| WO | WO 1993/010127 | 5/1993 |
| WO | WO 1995/015309 | 6/1995 |
| WO | WO 1995/029691 | 11/1995 |

(56) References Cited

FOREIGN PATENT DOCUMENTS

| | | |
|---|---|---|
| WO | WO 1997/040832 | 11/1997 |
| WO | WO 1998/018763 | 5/1998 |
| WO | WO 1998/019998 | 5/1998 |
| WO | WO 1998/025621 | 6/1998 |
| WO | WO 1998/050046 | 11/1998 |
| WO | WO 1998/050066 | 11/1998 |
| WO | WO 1999/016864 | 4/1999 |
| WO | WO 1999/025719 | 5/1999 |
| WO | WO 1999/056753 | 11/1999 |
| WO | WO 1999/061431 | 12/1999 |
| WO | WO 1999/062914 | 12/1999 |
| WO | WO 1999/067278 | 12/1999 |
| WO | WO 2000/010549 | 3/2000 |
| WO | WO 2000/023421 | 4/2000 |
| WO | WO 2000/034241 | 6/2000 |
| WO | WO 2000/056297 | 9/2000 |
| WO | WO 2000/069868 | 11/2000 |
| WO | WO 2000/071135 | 11/2000 |
| WO | WO 2001/000579 | 1/2001 |
| WO | WO 2001/27128 | 4/2001 |
| WO | WO 2001/034594 | 5/2001 |
| WO | WO 2001/052825 | 7/2001 |
| WO | WO 2001/055105 | 8/2001 |
| WO | WO 2001/068603 | 9/2001 |
| WO | WO 2001/081304 | 11/2001 |
| WO | WO 2001/081337 | 11/2001 |
| WO | WO 2001/096295 | 12/2001 |
| WO | WO 2001/097808 | 12/2001 |
| WO | WO 2002/000633 | 1/2002 |
| WO | WO 2002/002560 | 1/2002 |
| WO | WO 2002/014271 | 2/2002 |
| WO | WO 2002/030890 | 4/2002 |
| WO | WO 2002/030891 | 4/2002 |
| WO | WO 2002/034900 | 5/2002 |
| WO | WO 2002/038541 | 5/2002 |
| WO | WO 2002/051836 | 7/2002 |
| WO | WO 2002/055088 | 7/2002 |
| WO | WO 2002/068420 | 9/2002 |
| WO | WO 2002/062764 | 10/2002 |
| WO | WO 2002/076450 | 10/2002 |
| WO | WO 2002/083109 | 10/2002 |
| WO | WO 2002/083128 | 10/2002 |
| WO | WO 2003/000180 | 1/2003 |
| WO | WO 2003/000181 | 1/2003 |
| WO | WO 2003/000250 | 1/2003 |
| WO | WO 2003/002530 | 1/2003 |
| WO | WO 2003/002531 | 1/2003 |
| WO | WO 2003/002553 | 1/2003 |
| WO | WO 2003/002593 | 1/2003 |
| WO | WO 2003/002595 | 1/2003 |
| WO | WO 2003/002596 | 1/2003 |
| WO | WO 2003/004496 | 1/2003 |
| WO | WO 2003/004498 | 1/2003 |
| WO | WO 2003/015775 | 2/2003 |
| WO | WO 2003/022871 | 3/2003 |
| WO | WO 2003/024942 | 3/2003 |
| WO | WO 2003/024965 | 3/2003 |
| WO | WO 2003/035057 | 5/2003 |
| WO | WO 2003/035067 | 5/2003 |
| WO | WO 2003/037327 | 5/2003 |
| WO | WO 2003/038123 | 5/2003 |
| WO | WO 2003/040174 | 5/2003 |
| WO | WO 2003/045228 | 6/2003 |
| WO | WO 2003/045977 | 6/2003 |
| WO | WO 2003/055881 | 7/2003 |
| WO | WO 2003/057144 | 7/2003 |
| WO | WO 2003/057666 | 7/2003 |
| WO | WO 2003/068748 | 8/2003 |
| WO | WO 2003/068757 | 8/2003 |
| WO | WO 2003/072528 | 9/2003 |
| WO | WO 2003/072556 | 9/2003 |
| WO | WO 2003/074500 | 9/2003 |
| WO | WO 2003/080633 | 10/2003 |
| WO | WO 2003/082817 | 10/2003 |
| WO | WO 2003/084940 | 10/2003 |
| WO | WO 2003/095425 | 11/2003 |
| WO | WO 2003/099279 | 12/2003 |
| WO | WO 2003/099836 | 12/2003 |
| WO | WO 2003/101448 | 12/2003 |
| WO | WO 2003/101958 | 12/2003 |
| WO | WO 2003/104229 | 12/2003 |
| WO | WO 2003/106456 | 12/2003 |
| WO | WO 2004/000327 | 12/2003 |
| WO | WO 2004/004661 | 1/2004 |
| WO | WO 2004/007446 | 1/2004 |
| WO | WO 2004/007468 | 1/2004 |
| WO | WO 2004/009544 | 1/2004 |
| WO | WO 2004/014860 | 2/2004 |
| WO | WO 2004/018467 | 3/2004 |
| WO | WO 2004/018468 | 3/2004 |
| WO | WO 2004/018469 | 3/2004 |
| WO | WO 2004/020407 | 3/2004 |
| WO | WO 2004/032836 | 4/2004 |
| WO | WO 2004/033455 | 4/2004 |
| WO | WO 2004/037169 | 5/2004 |
| WO | WO 2004/037181 | 5/2004 |
| WO | WO 2004/041795 | 5/2004 |
| WO | WO 2004/041820 | 5/2004 |
| WO | WO 2004/043940 | 5/2004 |
| WO | WO 2004/046106 | 6/2004 |
| WO | WO 2004/048379 | 6/2004 |
| WO | WO 2004/050022 | 6/2004 |
| WO | WO 2004/050658 | 6/2004 |
| WO | WO 2004/052362 | 6/2004 |
| WO | WO 2004/052850 | 6/2004 |
| WO | WO 2004/058266 | 7/2004 |
| WO | WO 2004/064778 | 8/2004 |
| WO | WO 2004/067509 | 8/2004 |
| WO | WO 2004/069162 | 8/2004 |
| WO | WO 2004/071454 | 8/2004 |
| WO | WO 2004/076433 | 9/2004 |
| WO | WO 2004/076434 | 9/2004 |
| WO | WO 2004/085378 | 10/2004 |
| WO | WO 2004/085661 | 10/2004 |
| WO | WO 2004/087053 | 10/2004 |
| WO | WO 2004/087650 | 10/2004 |
| WO | WO 2004/092128 | 10/2004 |
| WO | WO 2004/096806 | 11/2004 |
| WO | WO 2004/099134 | 11/2004 |
| WO | WO 2004/103276 | 12/2004 |
| WO | WO 2004/103993 | 12/2004 |
| WO | WO 2004/104215 | 12/2004 |
| WO | WO 2004/104216 | 12/2004 |
| WO | WO 2004/108730 | 12/2004 |
| WO | WO 2004/110375 | 12/2004 |
| WO | WO 2004/110436 | 12/2004 |
| WO | WO 2004/111041 | 12/2004 |
| WO | WO 2004/111051 | 12/2004 |
| WO | WO 2004/112701 | 12/2004 |
| WO | WO 2005/000846 | 1/2005 |
| WO | WO 2005/000848 | 1/2005 |
| WO | WO 2005/003135 | 1/2005 |
| WO | WO 2005/009956 | 2/2005 |
| WO | WO 2005/011581 | 2/2005 |
| WO | WO 2005/012249 | 2/2005 |
| WO | WO 2005/012308 | 2/2005 |
| WO | WO 2005/012312 | 2/2005 |
| WO | WO 2005/019168 | 3/2005 |
| WO | WO 2005/020920 | 3/2005 |
| WO | WO 2005/023762 | 3/2005 |
| WO | WO 2005/025554 | 3/2005 |
| WO | WO 2005/026148 | 3/2005 |
| WO | WO 2005/030127 | 4/2005 |
| WO | WO 2005/030751 | 4/2005 |
| WO | WO 2005/032590 | 4/2005 |
| WO | WO 2005/033074 | 4/2005 |
| WO | WO 2005/033099 | 4/2005 |
| WO | WO 2005/034940 | 4/2005 |
| WO | WO 2005/037779 | 4/2005 |
| WO | WO 2005/037828 | 4/2005 |
| WO | WO 2005/040095 | 5/2005 |
| WO | WO 2005/042003 | 5/2005 |
| WO | WO 2005/042488 | 5/2005 |
| WO | WO 2005/044195 | 5/2005 |

(56) References Cited

FOREIGN PATENT DOCUMENTS

| WO | WO 2005/047297 | 5/2005 |
|---|---|---|
| WO | WO 2005/049022 | 6/2005 |
| WO | WO 2005/058849 | 6/2005 |
| WO | WO 2005/063750 | 7/2005 |
| WO | WO 2005/072530 | 8/2005 |
| WO | WO 2005/075426 | 8/2005 |
| WO | WO 2005/079795 | 9/2005 |
| WO | WO 2005/082348 | 9/2005 |
| WO | WO 2005/082849 | 9/2005 |
| WO | WO 2005/086904 | 9/2005 |
| WO | WO 2005/087235 | 9/2005 |
| WO | WO 2005/092877 | 10/2005 |
| WO | WO 2005/116029 | 12/2005 |
| WO | WO 2006/034435 | 3/2006 |
| WO | WO 2006/034489 | 3/2006 |
| WO | WO 2006/044391 | 4/2006 |
| WO | WO 2006/064033 | 6/2006 |
| WO | WO 2006/117359 | 11/2006 |
| WO | WO 2006/117360 | 11/2006 |
| WO | WO 2007/025943 | 3/2007 |
| WO | WO 2007/028814 | 3/2007 |
| WO | WO 2007/031548 | 3/2007 |
| WO | WO 2007/053865 | 5/2007 |
| WO | WO 2007/054577 | 5/2007 |
| WO | WO 2007/072992 | 6/2007 |
| WO | WO 2007/093610 | 8/2007 |
| WO | WO 2007/128749 | 11/2007 |
| WO | WO 2008/011154 | 1/2008 |
| WO | WO 2008/049923 | 5/2008 |
| WO | WO 2008/055870 | 5/2008 |
| WO | WO 2008/055940 | 5/2008 |
| WO | WO 2009/015179 | 1/2009 |
| WO | WO 2009/097996 | 8/2009 |
| WO | WO 2000/056296 | 9/2009 |
| WO | WO 2009/111078 | 9/2009 |
| WO | WO 2009/151116 | 12/2009 |
| WO | WO 2010/040055 | 4/2010 |
| WO | WO 2012/040072 | 3/2012 |
| WO | WO 2012/040082 | 3/2012 |
| WO | WO 2012/071459 | 5/2012 |
| WO | WO 2013/071077 | 5/2013 |
| WO | WO 2014/120538 | 8/2014 |
| WO | WO 2015/005365 | 1/2015 |
| WO | WO 2015/095548 | 6/2015 |
| WO | WO 2016/054728 | 4/2016 |
| WO | WO 2016/144862 | 9/2016 |
| WO | WO 2016/164413 | 10/2016 |
| WO | WO 2017/139588 | 8/2017 |
| WO | WO 2017/211830 | 12/2017 |
| WO | WO 2018/035446 | 2/2018 |
| WO | WO 2018/053040 | 3/2018 |
| WO | WO 2018/131626 | 7/2018 |
| WO | WO 2018/187350 | 10/2018 |
| WO | WO 2018/193006 | 10/2018 |
| WO | WO 2020/142365 | 7/2020 |
| WO | WO 2020/205025 | 10/2020 |
| WO | WO 2020/205027 | 10/2020 |
| WO | WO 2021/076616 | 4/2021 |

OTHER PUBLICATIONS

Berg et al., "The adipocyte-secreted protein Acrp30 enhances hepatic insulin action" Nature Medicine, 7: 947-953, 2001.
Bifari et al., "Multiple target tissue effects of GLP-1 analogues on non-alcoholic fatty liver disease (NAFLD) and non-alcoholic steatohepatitis (NASH)" Pharmacological research, 137:219-229, Nov. 1, 2018.
Boland et al., "Towards a standard diet-induced and biopsy-confirmed mouse model of non-alcoholic steatohepatitis: Impact of dietary fat source" World journal of gastroenterology, 25(33):4904, Sep. 7, 2019.
Bologna et al., "Voluntary, spontaneous and reflex blinking in patients with clinically probable progressive supranuclear palsy" Brain 132: 502-510, 2009.

Boxer et al., "Advances in progressive supranuclear palsy: new diagnostic criteria, biomarkers, and therapeutic approaches" Lancet 16:552-563, 2017.
Boxer et al., "Davunetide in patients with progressive supranuclear palsy: a randomised, double-blind, placebo-controlled phase 2/3 trial" Lancet Neural. 132: 676-685, 2014.
Boxer et al., "Saccade abnormalities in autopsy-confirmed frontotemporal lobar degeneration and Alzheimer disease" Arch. Neural., 69: 509-517, 2012.
Buehring et al., "Glucocorticoid-induced osteoporosis: an update on effects and management" Journal of allergy and clinical immunology 32(5): 1019-1030, Nov. 1, 2013.
Cho et al., "Subcortical 18 F-AV-1451 binding patterns in progressive supranuclear palsy" Mav. Disard. 32: 134-140, 2017.
Clerici et al., "Rehabilitation in progressive supranuclear palsy: Effectiveness of two multidisciplinary treatments" PLoS One 12: e0170927, 2017.
ClinicalTrials.gov [Online], "Archive NCT02638038" Dec. 20, 2015, retrieved on Dec. 20, 2015 from URL<https://clinicaltrials.gov/ct2/history/NCT02638038>, 4 pages.
Collino et al., "Modulation of the oxidative stress and inflammatory response by PPAR-gamma agonists in the hippocampus of rats exposed to cerebral ischemia/reperfusion" Eur J Pharmacol., 530(1-2): 70-80, 2006.
Danne et al., "Combined SGLT1 and SGLT2 inhibitors and their role in diabetes care" Diabetes technology & therapeutics, 20(S2): 10 pages, Jun. 1, 2018.
Depo-Provera, Trademark Reg. No, 2,680,672, 1 page Year: 2003.
Glaesner et al., "Engineering and characterization of the long-acting glucagon-like peptide-1 analogue LY2189265, an Fc fusion protein" Diabetes/metabolism research and reviews, 26(4):287-296, May 2010.
Golbe et al., "A clinical rating scale for progressive supranuclear palsy" Brain 130(6): 1552-1565, 2007.
Hinz et al., "Molecular Genetics of Neurodegenerative Dementias" Cold Spring Harb. Perspect Biol., 9(4), 23 pages, 2017.
Hoglinger et al. "Identification of common variants influencing risk of the tauopathy Progressive Supranuclear Palsy" Nature Genet. 43:699-705, 2011.
Honda et al., "The selective SGLT2 inhibitor ipragliflozin has a therapeutic effect on nonalcoholic steatohepatitis in mice" PLoS One, 11(1):e0146337, 13 pages, Jan. 5, 2016.
Hughes et al., "The binaural masking level difference: cortical correlates persist despite severe brain stem atrophy in progressive supranuclear palsy" J Neuraphysial. 112: 3086-3094, 2014.
International Preliminary Report on Patentability and Written Opinion in International Application No. PCT/US2018/025923, dated Oct. 8, 2019, 10 pages.
International Preliminary Report on Patentability in International Appln. PCT/US2019/068710, dated Jul. 15, 2021, 12 pages.
International Search Report in International Appln. PCT/US2019/068706, dated Jun. 25, 2020, 21 pages.
International Search Report in International Appln. PCT/US2019/068710, dated Jun. 25, 2020, 22 pages.
Josephs et al., "The evolution of primary progressive apraxia of speech" Brain 137: 2783-2795, 2014.
Josephs et al., "Voxel-based morphometry in autopsy proven PSP and CBD" Neurabial. Aging 29: 280-289, 2008.
Kalra et al., "Glucagon-like peptide-1 receptor agonists in the treatment of type 2 diabetes: past, present, and future" Indian journal of endocrinology and metabolism, 20(2): 14 pages, Mar. 2016.
Khalil et al., "Neurofilaments as biomarkers in neurological disorders" Nature Reviews Neurology, 14(10):577-589, Oct. 2018.
Kubota et al., "Adiponectin Stimulates AMP-Activated Protein Kinase in the Hypothalamus and Increases Food Intake" Cell Metab., 6: 55-68, 2007.
Kuchay et al., "Effect of empagliflozin on liver fat in patients with type 2 diabetes and nonalcoholic fatty liver disease: a randomized controlled trial (E-LIFT Trial)" Diabetes care, 41(8):1801-1808, Aug. 1, 2018.

(56) References Cited

OTHER PUBLICATIONS

Lamb et al., "Progressive Supranuclear Palsy and Corticobasal Degeneration: Pathophysiology and Treatment Options" Curr. Treat Options Neural. 14: 42, 18 pages, 2016.
Lebovitz et al., "Rosiglitazone Clinical Trials Study Group. Rosiglitazone monotherapy is effective in patients with type 2 diabetes" The Journal of Clinical Endocrinology & Metabolism, 86(1):280-288, Jan. 1, 2001.
Ling et al., "Clinical Approach to Progressive Supranuclear Palsy" J Mov. Discord. 9(1): 3-13, 2016.
Litvan et al., "Environmental and Occupational Risk Factors for Progressive Supranuclear Palsy: Case-Control Study" Movement Disord 31: 644-652, 2016.
Magdalinou et al., "A panel of nine cerebrospinal fluid biomarkers may identify patients with atypical parkinsonian syndromes" J Neural. Neurosurg, Psychiatiy 86: 1240-124 7, 2015.
Magdalinou et al., "Cerebrospinal fluid biomarkers in parkinsonian conditions: an update and future directions" J. Neural. Neurosurg, Psychiatiy, 85(10): 1065-1075, 2014.
Marquie et al., "Validating novel tau positron emission tomography tracer [F-18]-AV-1451 (T807) on postmortem brain tissue" Ann. Neural. 78: 787-800, 2015.
Mazza et al., "The role of metformin in the management of NAFLD" Experimental diabetes research, 2012: 14 pages, Dec. 12, 2011.
Min et al., "Critical Role of Acetylation in Tau-Mediated Neurodegeneration and Cognitive Deficits" Nat. Med. 21: 1154-1162, 2015.
Murphy et al., "Effects of thiazolidinediones on bone loss and fracture" Annals of Pharmacotherapy, Dec. 2007, 41(12):2014-2018.
Pavo et al., "Effect of pioglitazone compared with metformin on glycemic control and indicators of insulin sensitivity in recently diagnosed patients with type 2 diabetes" The Journal of Clinical Endocrinology & Metabolism, 88(4):1637-1645, Apr. 1, 2003.
Petzold, "Neurofilament phosphoforms: surrogate markers for axonal injury, degeneration and loss" Journal of the neurological sciences, 233(1-2): 35 pages, Jun. 15, 2005.
Raskin et al., "Rosiglitazone short-term monotherapy lowers fasting and post-prandial glucose in patients with type II diabetes" Diabetologia, 43(3):278-284, Mar. 2000.
Rosenstock et al., "Effects of dapagliflozin, an SGLT2 inhibitor, on HbAlc, body weight, and hypoglycemia risk in patients with type 2 diabetes inadequately controlled on pioglitazone monotherapy" Diabetes care, 35(7):1473-1478, Jul. 1, 2012.
Roth et al., "Combined obeticholic acid and elafibranor treatment promotes additive liver histological improvements in a diet-induced ob/ob mouse model of biopsy-confirmed NASH" Scientific reports, 9(1):1-3, Jun. 21, 2019.
Sai et al., "Systematic design of trypsin cleavage site mutated exendin4-cysteine 1, an orally bioavailable glucagon-like peptide-1 receptor agonist" International journal of molecular sciences, 18(3):578, Mar. 2017.
Santiago et al., "A Network Approach to Diagnostic Biomarkers in Progressive Supranuclear Palsy" Mov. Discord 29(4): 550-555, 2014.
Santos-Santos et al., "Features of Patients With Nonfluent/Agrammatic Primary Progressive Aphasia With Underlying Progressive Supranuclear Palsy Pathology or Corticobasal Degeneration" JAMA Neural. 73:733-742, 2016.
Scherling et al., "CSF neurofilament concentration reflects disease severity in frontotemporal degeneration" Ann. Neural.75: 116-126, 2014.
Schneider et al., "Retinal single-layer analysis in Parkinsonian syndromes: an optical coherence tomography study" J Neural Transm, 121: 41-47, 2014.
Smith et al., "Increased basal ganglia binding of 18 F-AV-1451 in patients with progressive supranuclear palsy" Mav. Disard. 32: 108-114, 2017.

Spatola et al., "SGLT1 and SGLT1 inhibitors: a role to be assessed in the current clinical practice" Diabetes Therapy, 9(1):427-430, Feb. 2018.
Tolbol et al., "Metabolic and hepatic effects of liraglutide, obeticholic acid and elafibranor in diet-induced obese mouse models of biopsy-confirmed nonalcoholic steatohepatitis" World Journal of Gastroenterology, 24(2): 17 pages, Jan. 14, 2018.
Walsh et al., "Rest-activity rhythm disruption in progressive supranuclear palsy" Sleep Med 22; 50-56, 2016.
Whitwell et al.,"[18 F] AV-1451 tau positron emission tomography in progressive supranuclear palsy" Mov Disord. 32: 124-133, 2016.
Whitwell et al., "Midbrain atrophy is not a biomarker of progressive supranuclear palsy pathology" Eur. J Neural. 20: 1417-1422, 2013.
Yamauchi et al., "Adiponectin stimulates glucose utilization and fatty-acid oxidation by activating AMP-activated protein kinase" Nat Med., 8: 1288-1295, 2002.
Yamauchi et al., "Targeted disruption of AdipoR1 and AdipoR2 causes abrogation of adiponectin binding and metabolic actions" Nat Med., 13: 332-339, 2007.
Yanamandra et al., "Anti-tan antibody reduces insoluble tau and decreases brain atrophy" Ann Clin Transl Neurol. 2: 278-288, 2015.
Khan et al., "Biomarker Detection of Neurological Disorders through Spectroscopy Analysis," International Dental & Medical Journal of Advanced Research, 2018, 4(1):1-9.
Kuhle et al., "Fingolimod and CSF neurofilament light chain levels in relapsing-remitting multiple sclerosis," Neurology, Apr. 21, 2015, 84(16):1639-1643.
Siuly et al., "Medical big data: neurological diseases diagnosis through medical data analysis," Data Science and Engineering, Jun. 1, 2016, 1(2):54-64.
PCT International Preliminary Report on Patentability in International Appln. No. PCT/US2019/025118, dated Oct. 15, 2020, 11 pages.
Abenavoli et al., "Obeticholic acid: a new era in the treatment of nonalcoholic fatty liver disease" Pharmaceuticals, 11(4):104, 10 pages, Dec. 2018.
Afdal et al., "Is pulmonary vascular disease reversible with PPAR γ agonists?" Microcirculation, 25(3):e12444, 19 pages, Apr. 2018.
Al-Quaydheb et al., "Relation between vitamin B12 and Non-alcoholic fatty Liver Disease: A Hospital Based Study" International Journal of Advanced Research, 3:(6) 1335-1343, Jun. 2015
Assad et al, "Metabolic dysfunction in pulmonary arterial hypertension" Current hypertension reports, 17(3):20, 9 pages Mar. 1, 2015.
Behringer et al., "Pioglitazone alleviates cardiac and vascular remodelling and improves survival in monocrotaline induced pulmonary arterial hypertension" Naunyn-Schmiedeberg's archives of pharmacology, 389(4): 11 pages, Apr. 1, 2016.
Bradley et al. "Pulmonary arterial hypertension and insulin resistance" Journal of molecular and genetic medicine: an international journal of biomedical research, 2(Suppl 1), 18 pages, 2014.
Brittain et al., "Fatty acid metabolic defects and right ventricular lipotoxicity in human pulmonary arterial hypertension" Circulation, 133(20):1936-1944, May 17, 2016.
Calvier et al., "LRP1 deficiency in vascular SMC leads to pulmonary arterial hypertension that is reversed by PPARγ activation" Circulation research, 124(12):1778-1785, Jun. 7, 2019.
Calvier et al., "PPARγ links BMP2 and TGFβ1 pathways in vascular smooth muscle cells, regulating cell proliferation and glucose metabolism" Cell metabolism, 25(5): 1118-1134, May 2, 2017.
Carr et al., "FXR agonists as therapeutic agents for non-alcoholic fatty liver disease" Current atherosclerosis reports, 17(4): 16, 14 pages, Apr. 1, 2015.
CAS Registry Record for INT-131 (Jan. 19, 2001), retrieved from STN on Apr. 13, 2020. (Year: 2001).
Chen et al., "Oestrogen inhibition reverses pulmonary arterial hypertension and associated metabolic defects" European Respiratory Journal, 50(2), 14 pages, Aug. 1, 2017.
Clapp et al., "The mechanistic basis of prostacyclin and its stable analogues in pulmonary arterial hypertension: Role of membrane versus nuclear receptors" Prostaglandins & other lipid mediators, 120: 16 pages, Jul. 1, 2015.

(56) References Cited

OTHER PUBLICATIONS

Depaoli et al., "INT131 Besylate, a Selective PPAR[gamma] Modulator (SPPARM), Improved Glyce~ic Control in Patients with Type 2 Diabetes without Causing the Edema Seen with Pioglitazone" Abstract, American Diabetes Association, 2 pages Jun. 1, 2010.
Diehl et al., "Treatment with selonsertib, an inhibitor of apoptosis signal-regulating kinase 1, hepatic phospho-p38 expression and markers of hepatocellular apoptosis and necrosis in patients with nonalcoholic steatohepatitis" Journal of Hepatology, 66(1), S51-S52, 2017.
Fiorucci et al., "Cross-talk between farnesoid-X-receptor (FXR) and peroxisome proliferator-activated receptor γ contributes to the antifibrotic activity of FXR ligands in rodent models of liver cirrhosis" Journal of Pharmacology and Experimental Therapeutics, 315(1): 12 pages, Oct. 1, 2005.
Gong et al., "Hypoxia induces downregulation of PPAR-γ in isolated pulmonary arterial smooth muscle cells and in rat lung via transforming growth factor-β signaling" American Journal of Physiology-Lung Cellular and Molecular Physiology, 301(6):L899-907, Dec. 2011.
Hansmann et al., "PPARγ activation: a potential treatment for pulmonary hypertension" Science translational medicine, 1(12):12ps14, 15 pages Dec. 23, 2009.
Haznedaroglu, "Monitoring the response to tyrosine kinase inhibitor (TKI) treatment in chronic myeloid leukemia (CML)" Mediterranean journal of hematology and infectious diseases, 6(1), e2014009, 8 pages, 2014.
International Search Report and Written Opinion in international application No. PCT/US2020/055567, dated Jan. 22, 2021, 16 pages.
International Search Report and Written Opinion in International Appln. No. PCT/US2019/068688, dated Apr. 20, 2020, 17 pages.
International Search Report and Written Opinion in International Appln. PCT/US2019/068693, dated Apr. 20, 2020, 19 pages.
International Search Report and Written Opinion in International Appln. PCT/US2019/068698, dated Jul. 3, 2020, 21 pages.
International Search Report and Written Opinion in International Appln. PCT/US2019/068704, dated Jun. 25, 2020, 22 pages.
Jojima et al., "Empagliflozin (an SGLT2 inhibitor), alone or in combination with linagliptin (a DPP-4 inhibitor), prevents steatohepatitis in a novel mouse model of non-alcoholic steatohepatitis and diabetes" Diabetology & metabolic syndrome, Dec. 2016;8(1):1-11, Dec. 2016.
Jung et al., "Sitagliptin attenuates methionine/choline-deficient diet-induced steatohepatitis" Diabetes research and clinical practice, 105(1): 12 pages, Jul. 1, 2014.
Kim et al., "Rosiglitazone attenuates hypoxia-induced pulmonary arterial hypertension in rats" Respirology, 15(4):659-668, May 2010.
Legchenko et al., "PPARγ agonist pioglitazone reverses pulmonary hypertension and prevents right heart failure via fatty acid oxidation" Science translational medicine, 10(438): 18 pages, Apr. 25, 2018.
Liu et al., "Vitamin b6 prevents endothelial dysfunction, insulin resistance, and hepatic lipid accumulation in apoe-/- mice fed with high-fat diet" Journal of diabetes research, 2016, 8 pages Oct. 2016.
Machado et al., "Vitamin B5 and N-acetylcysteine in nonalcoholic steatohepatitis: a preclinical study in a dietary mouse model" Digestive diseases and sciences, 61(1):12 pages, Jan. 1, 2016.
Marangoni et al., "A candidate gene study reveals association between a variant of the Peroxisome Proliferator-Activated Receptor Gamma (PPAR-γ) gene and systemic sclerosis" Arthritis research & therapy, 17(1):Dec. 1-8, 2015.
Oliveira et al., "Vitamin C and vitamin E in prevention of nonalcoholic fatty liver disease (NAFLD) in choline deficient diet fed rats" Nutrition journal, 2(1): 1-5, Dec. 2003.
Perrotta et al., "Pulmonary hypertension and obesity: focus on adiponectin" International journal of molecular sciences, 20(4):912, 13 pages, Jan. 2019.

Phan et al., "Adipose tissue dysfunction tracks disease progression in two Huntington's disease mouse models" Human molecular genetics, Mar. 15, 2009, 18(6):1006-1016.
Prat et al., "The effect of antidiabetic medications on non-alcoholic fatty liver disease (NAFLD)" Hormones, 17(2):219-229, Jun. 2018.
Pulley, "CCR5 antagonists: from discovery to clinical efficacy" Chemokine Biology—Basic Research and Clinical Application, 2007 vol. II, 145-163, 2007.
Rashid et al., "Inhaled sildenafil as an alternative to oral sildenafil in the treatment of pulmonary arterial hypertension (PAH)" Journal of Controlled Release, 250: 23 pages, Mar. 28, 2017.
Rashid et al., "Repurposing rosiglitazone, a PPAR-γagonist and oral antidiabetic, as an inhaled formulation, for the treatment of PAH" Journal of Controlled Release, 280: 18 pages, Jun. 2018.
Saeed et al., "Disturbed vitamin A metabolism in non-alcoholic fatty liver disease (NAFLD)" Nutrients, 10(1):29, 25 pages, Jan. 2018.
Sakauchi et al., "Pleiotropic properties of ASK1. Biochimica et Biophysica Acta (BBA)-General Subjects" 1861(1):3030-3038, Jan. 1, 2017.
Sanyal et al., "LB-23 Tropifexor (TXR), an FXR Agonist for the Treatment of Nash—Interim Results from First Two Parts of Phase 2b Study Flight-FXR" Hepatology, 68(1): 2 pages Oct. 1, 2018.
Sato et al., "Vitamin E has a beneficial effect on nonalcoholic fatty liver disease: a meta-analysis of randomized controlled trials" Nutrition, 31(7-8): 22 pages, Jul. 1, 2015.
SealRocktx.com [Online], "Seal Rock Therapeutics Advancing Differentiated ASK1 Inhibitor Lead Candidate SRT-015 in Nonalcoholic Steatohepatitis (NASH)" retrieved from the internet URL<https://www.prnewswire.com/news-releases/seal-rock-therapeuticsadvancing-differentiated-ask1-inhibitor-lead-candidate-srt-015-innonalcoholic-steatohepatitis-nash-3007 47392~html>4 pages.
Struthers et al., "CCR2 antagonists" Current topics in medicinal chemistry, Sep. 1, 2010, 10(13):1278-1298.
Sumida et al., "Current and future pharmacological therapies for NAFLD/NAS" Journal of gastroenterology, 53(3): 15 pages, Mar. 2018.
Terao et al., "Design and biological evaluation of imidazo [1, 2-a] pyridines as novel and potent ASK1 inhibitors" Bioorganic & medicinal chemistry letters, 22(24):7326-7329, Dec. 15, 2012.
USP.org [online], "711 Dissolution" Dec. 1, 2011, retrieved Sep. 30, 2021, retrieved from URL <https://www.usp.org/sites/default/files/usp/document/harmonization/gen-method/stage_6_monograph_25_feb_2011.pdf>, 8 pages.
Vaddi, "TNF Signaling Pathway Inhibitors for Inflammation-CCR2 Antagonists" Target Validation in Drug Discovery, Jan. 1, 2007, Academic Press, 223-240.
Watson et al., "Pulmonary hypertension: old targets revisited (statins, PPARs, beta-blockers)" Pharmacotherapy of Pulmonary Hypertension, 531-548, 2013.
Yaghoubi et al., "Comparison of fenofibrate and pioglitazone effects on patients with nonalcoholic fatty liver disease" European journal of gastroenterology & hepatology, 29(12): 4 pages, Dec. 1, 2017.
Yang et al., "Low vitamin D status is associated with advanced liver fibrosis in patients with nonalcoholic fatty liver disease" Endocrine, 55(2): 9 pages, Feb. 1, 2017.
Zamanian et al., "Insulin resistance in pulmonary arterial hypertension" European respiratory journal, 33(2):318-324, Feb. 1, 2009.
Zhan et al., "Protective effect of probucol on liver injury induced by carbon tetrachloride in rats" Hepatology international, 5(4):899-905, Dec. 2011.
Huayu et al., "The correlation between peroxisome proliferator-activated receptor γ and liver diseases," International Journal of Epidemiology and Infectious Disease, Feb. 2013, 40(1): 62-65, English Abstract.
Pubchem. CID 162584226, "Benzenesulfonamide, 2,4-dichloro-N-(3,5-dichloro-4-(3-quinolinyloxy)phenyl)," Oct. 25, 2006 [retrieved on Mar. 22, 2021], retrieved from the Internet. <URL: https://pubchem.ncbi.nlm.nih.gov/compound/10229498>, 23 pages.
Chigurupati et al., "A step ahead of PPARγ full agonists to PPARγ partial agonists: Therapeutic perspectives in the management of diabetic insulin resistance," European J. of Pharm., 2015, 755:50-57.

(56) References Cited

OTHER PUBLICATIONS

Oshima et al., "Adiponectin increases bone mass by suspecting osteoclast and activating osteoblast," Biochem. and Bophys. Res. Comm., 2005, 331:520-526.
Avcu et al., "Association of plasma adiponectin concentrations with chronic lymphocytic leukemia and myeloproliferative diseases," International journal of hematology, Apr. 1, 2006, 83(3):254-258.
Kersey et al., "T0903131, a selective modulator of PPAR-gamma activity, increases adiponectin levels in healthy subjects," Diabetes, Jun. 1, 2004.
Nowak et al., "Differentiation therapy of leukemia: 3 decades of development," Blood, 113(16), 3655-3665.
Ray et al., "Human multiple myeloma cells express peroxisome proliferator-activated receptor γ and undergo apoptosis upon exposure to PPARγ ligands. Clinical Immunology," Nov. 1, 2004, 113(2):203-213.
Tella et al., "Prevention and treatment of postmenopausal osteoporosis," The Journal of steroid biochemistiy and molecular biology, Jul. 1, 2014, 142:155-170.
Girnun et al., "Synergy between PPARgamma ligands and platinum-based drugs in cancer," Cancer Cell, May 2007, 11(5):395-406.
PCT International Search Report and Written Opinion in International Appln. No. PCT/US2020/034480, dated Aug. 18, 2020, 15 pages.
Taylor et al., "Health Impact Analysis of Cisplatin, Carboplatin and Oxaliplatin: Quantifying the health impact of platinum compounds," Johnson Matthey Technology Review, Jan. 2017, retrieved from URL <www.technology.matthey.com/article/61/1/32-39/>, 32-39.
Abd El-Haleim et al., "Effects of combined PPAR-γ and PPAR-α agonist therapy on fructose induced NASH in rats: Modulation of gene expression", European Journal of Pharmacology, 773: 59-70, 2016.
Abdelmegeed et al., "CYP2E1 potentiates binge alcohol-induced gut leakiness, steatohepatitis, and apoptosis", Free Radical Biology and Medicine 65, 1238-1245, 2013.
Abdelmegeed et al., "PPARa Expression Protects Male Mice from High Fat-Induced Nonalcoholic Fatty Liver", The Journal of Nutrition, vol. 141, Issue 4, pp. 603-610, 2011.
Abu-Elheiga et al., "Mutant mice lacking acetyl-CoA carboxylase 1 are embryonically lethal", Proc. Nat. Acad Sci. USA, 102: 12011-12016, 2005.
Adams et al., "Hepascore: An Accurate Validated Predictor of Liver Fibrosis in Chronic Hepatitis C Infection", ClinChem., 51(10): 1867-1873, 2005.
Addy et al., "Hypoadiponectinemia is Associated with Insulin Resistance, Hypertriglyceridemia, and Fat Redistribution in Human Immunodeficiency Virus-Infected Patients Treated with Highly Active Antiretroviral Therapy", J Clin Endocrinol Metab, 88(2): 627-636, 2003.
Agerso et al., "The pharmacokinetics, pharmacodynamics, safety and tolerability of NN2211, a new long-acting GLP-1 derivative, in healthy men", Diabetologia, 45(2): 195-202, 2002.
Aki et al., "Role of adiponectin in chronic lymphocytic leukemia", Egyptian J Haematology, 37(4), 187-192, 2012.
Albers et al., Frontal Lobe Dysfunction in Progressive Supranuclear Palsy: evidence for oxidative stress and mitochondrial impairment, J Neurochem,, 74(2): 878-81, 2000.
Ali et al., "Recent advances in the development of farnesoid X receptor agonists", Ann Transl Med., 3(1): 5, 2015.
Altekruse et al., SEER Cancer Statistics Review, 1975-2007, National Cancer Institute, Table of Contents, 4 pages.
Anagnostis et al., "Comparative effects of rosuvastatin and atorvastatin on glucose metabolism and adipokine levels in non-diabetic patients with dyslipidaemia: a prospective randomised open-label study", Int J ClinPract, 65, 6, 679-683, 2011.
Anastasilakis et al., "Circulating Irisin in Healthy, Young Individuals: Day-Night Rhythm, Effects of Food Intake and Exercise, and Associations With Gender, Physical Activity, Diet, and Body Composition", J Clin Endocrinol Metab, 99(9): 3247-3255, 2014.

Angulo et al., "The NAFLD Fibrosis Score: A Noninvasive System That Identifies Liver Fibrosis in Patients with NAFLD", Hepatology, 45: 846-854, 2007.
Anonymous: "Coherus Announces Positive Phase 2b Efficacy Data on Novel Oral Therapy in Relapsing Remitting Multiple Sclerosis | Coherus Biosciences, Inc.", Jun. 28, 2016, Retrieved from the Internet: URL: https://investors.coherus.com/news-releases/news-releasedetails/.
Ansel et al., Pharmaceutical Dosage Forms and Drug Delivery Systems, 6th Ed., Williams & Wilkins, Baltimore MD, 1995.
Antoniadisa et al., "Insulin resistance in relation to melanoma risk", vol. 21, No. 6, 541-546, 2011.
Anty et al., "Liver fibrogenesis and metabolic factors," Clinics and Research in Hepathology and Gastroenterology, 2011, 35:S10-S20.
Aoyama et al., "Pioglitazone Promotes Survival and Prevents Hepatic Regeneration Failure After Partial Hepatectomy in Obese and Diabetic KK-Ay Mice", Hepa tology, vol. 49, No. 5, 1636-16454, 2009.
Aragonès et al., "PNPLA3 Expression is Related to Liver Steatosis in Morbidly ObeseWomen with Non-Alcoholic Fatty Liver Disease", Int. J. Mol. Sci., 17, 630, 13 pages 2016.
Aref et al., "Impact of serum adiponectin and leptin levels in acute leukemia", Hematology, 18( 4 ): 198-203, 2013.
Arioglu et al., "Efficacy and safety of troglitazone in the treatment of lipodystrophy syndromes.", vol. 133, No. 4, pp. 263-274, 2000.
Aronis et al., "Circulating irisin levels and coronary heart disease: association with future acute coronary syndrome and major adverse cardiovascular events", International Journal of Obesity, 39, 156-161, 2015.
Aronis et al., "Short-term walnut consumption increases circulating total adiponectin and apolipoprotein A concentrations, but does not affect makers of inflammation or vascular injury in obese humans with the metabolic syndrome: data from a double-blinded, randomized, placebo-controlled study," Metab. Clinical and Experimental, 2011, 61:577-582.
Arulmozhi et al., "GLP-1 based therapy for type 2 diabetes", European Journal of Pharmaceutical Sciences, vol. 28, pp. 96-108, 2006.
Auger et al., "Discovery and preclinical profile of Saxagliptin (BMS-477118): a highly potent, long-acting, orally active dipeptidyl peptidase IV inhibitor for the treatment of type 2 diabetes.", J Med. Chem. 48(5): 5025-5037, 2005.
Augustyns et al., "Dipeptidyl peptidase IV inhibitors as new therapeutic agents for the treatment of Type 2 diabetes", Exp, Opin. Then Patents, 13: 499-510, 2003.
Augustyns et al., "Inhibitors of proline-specific dipeptidyl peptidases: DPP IV inhibitors as a novel approach for the treatment of Type 2 diabetes", Expert Opinion on Therapeutic Patents, 15(10): 1387-1407, 2005.
Australian Office Action in Application No. 2016229982, dated Jun. 24, 2019, 4 pages.
Avcu et al., "Plasma Adiponectin Concentrations in Relation to Chronic Lymphocytic Leukemia and Chronic :rviyeloproliferative Diseases", Blood, 104(11), 4743, 2004.
Axtell et al., "T helper type 1 and 17 cell Determine Efficacy of IFN-B in Multiple Sclerosis and Experimental Encephalomyelitis", Nat Med., 16(4): 406-412, 2010.
Ballabh et al., "The blood-brain barrier: an overview: structure, regulation, and clinical implications", Neurobiol Dis, 16(1), 1-13, 2004.
Ban et al., "Structure-based design, synthesis, and nonalcoholic steatohepatits (NASH)-preventive effect of phenylpropanoic acid peroxisome proliferator-activated receptor (PPAR) beta-selective agonists," Bioorganic & Medicinal Chemistry, 2011, 19:3183-3191.
Barb et al., "Adiponectin in relation to malignancies: a review of existing basic research and clinical evidence", Am J Clin Nutr., 86(suppl): 858S-66S, 2007.
Barb et al., "Adiponectin signals in prostate cancer cells through Akt to activate the mammalian target of rapamycin pathway", Endocrine-Related Cancer 14, 995-1005, 2007.
Barb et al., "Adiponectin: a link between obesity and cancer," Expert Opinion on Investigational Drugs, 2006, 15(8):917-931.

(56) References Cited

OTHER PUBLICATIONS

Barber et al., "Structure and regulation of acetyl-CoA carboxylase genes of metazoa", Biochim. et Biophys. Acta., 1733(1): 1-28, 2005.

Baron et al., "PPAR activation differently affects microparticle content in atherosclerotic lesions and liver of a mouse model of atherosclerosis and NASH," Atherosclerosis, 2011, 218:69-76.

Bastianello et al., "Serial study of gadolinium-DTPA MRI enhancement in multiple sclerosis", Neurology, 40(4), 591-595, 1990.

Bedogni et al., "The Fatty Liver Index: a simple and accurate predictor of hepatic steatosis in the general population", BioMed Central, BMC Gastroenterology 6: 33, 7 pages, 2006.

Belalcazar et al., "Adiponectin and the mediation of HDL-cholesterol change with improved lifestyle: the Look AHEAD Study", Journal of Lipid Research, vol. 53, 2726-2733, 2012.

Belalcazar et al., "Improving Adiponectin Levels in Individuals With Diabetes and Obesity: Insights From Look AHEAD", Diabetes Care, 38: 1544-1550, 2015.

Belfort et al. "A Placebo-Controlled Trial of Pioglitazone in Subjects with Nonalcoholic Steatohepatitis", The New England Journal of Medicine, pp. 2297-2307, 2006.

Beraza et al., "Pharmacological IKK2 inhibition blocks liver steatosis and initiation of non-alcoholic steatohepatitis", Gut, 57: 655-663, 2008.

Berge et al., "Pharmaceutical Salts", Journal of Pharmaceutical Science, 66, 1-19, 1977.

Bluher et al., "Altered Levels of Adiponectin and Adiponectin Receptors May Underlie the Effect of Ciliary Neurotrophic Factor (CNTF) to Enhance Insulin Sensitivity in Diet-induced Obese Mice", Horm Metab Res., 40: 225-227, 2008.

Bluher et al., "Circulating Adiponectin and Expression of Adiponectin Receptors in Human Skeletal Muscle: Associations with Metabolic Parameters and Insulin Resistance and Regulation by Physical Training", J. Clin, Endocrinol, Metab., 91: 2310-2316, 2006.

Bluher et al., "Effects of a 1-Year Exercise and Lifestyle Intervention on Irisin, Adipokines, and Inflammatoiy Markers in Obese Children", Obesity, 22, 1701-1708, 2014.

Bluher et al., "From leptin to other adipokines in health and disease: Facts and expectations at the beginning of the 21st centmy," Metabolism Clinical & Experimental, 2015, 64:131-145.

Bluher et al., "Gene Expression of Adiponectin Receptors in Human Visceral and Subcutaneous Adipose Tissue is Related to Insulin Resistance and Metabolic Parameters and is Altered in Response to Physical Training", Diabetes Care 30: 3110-3115, 2007.

Bluher et al., "Responsiveness to Peripherally Administered Melanocortins in Lean and Obese Mice", Diabetes, vol. 53: 82-90, 2004.

Bluher et al., "Total and High-Molecular Weight Adiponectin in Relation to Metabolic Variables at Baseline and in Response to an Exercise Treatment Program", Diabetes Care 30:280-285, 2007.

Brault et al., "Statin treatment and new-onset diabetes: A review of proposed mechanisms," Metabolism Clinical & Experimental, 2014, 63:735-745.

Brazilian Office Action in Brazilian Application No. BR112013007468-8, dated May 29, 2019.

Brennan et al., "Leptin and Adiponectin: Their Role in Diabetes", Current Diabetes Reports, 7: 1-2, 2007.

Brennan et al., "Phobic Anxiety os Associated With Higher Serum Concentrations of Adipokines and Cytokines in Women With Diabetes", Diabetes Care 32: 926-931, 2009.

Brenner et al., "Decoding cell death signals in liver inflammation", J Hepatol., 59(3): 583-94, 2013.

Bright et al., "PPAR Regulation of Inflammatory Signaling in CNS Diseases", PPAR Research, vol. 2008, Article ID 658520, 12 pages, 2008.

Brunt et al., "Nonalcoholic Fatty Livery Disease (NAFLD) Activity Score and the Histopathologic Diagnosis in NAFLD: Distinct Clinicopathologic Meanings", Hepatology, 53: 810-820, 2011.

Brunt et al., "Nonalcoholic Steatohepatitis: A Proposal for Grading and Staging the Histological Lesions", Am J Gastroenterol., 94: 2467-2474, 1999.

Budas et al., "Reduction of liver steatosis and fibrosis with an ask1 inhibitor in a murine model of nash is accompanied by improvements in cholesterol, bile acid and lipid metabolism", J Hepatol., 64 (Suppl.): S170, 2016.

Buechler et al., "Adiponectin, a key adipokine in obesity related liver diseases", World J. of Gastroenterology, 17(23), 2801-2811, 2011.

Bullen et al., "Regulation of adiponectin and its receptors in response to development of diet-induced obesity in mice", Am J Physiol Endocrinol Metab 292: E1079-E1086, 2007.

Caprio et al., "Antiadipogenic Effects of the Mineralocorticoid Receptor Antagonist Drospirenone: Potential Implications for the Treatment of Metabolic Syndrome", Endocrinology, 152(1): 113-25, 2011.

CAS No. 275371-94-3, 3 pages, 2019.

CAS No. 445479-97-0, 2 pages, 2019.

Cave et al., "Nuclear receptors and nonalcoholic fatty liver disease," Biocehmica et Biophysica Acta, 2016. 1859:1083-1099.

Chalasani et al., "The Diagnosis and Management of Nonalcoholic Fatty Liver Disease: Practice Guidance From the American Association for the Study of Liver Diseases", Hepatology, 67(1): 328-357, 2018.

Chalasani et al., "The Diagnosis and Management of Non-Alcoholic Fatty Liver Disease: Practice Guideline by the American Association for the Study of Liver Diseases, American College of Gastroenterology, and the American Gastroenterological Association", Hepatology, vol. 55, No. 6, 2005-2023, 2012.

Chalasani et al., "The Diagnosis and Management of Non-alcoholic Fatty Liver Disease: Practice Guideline by the American Gastroenterological Association, American Association for the Study of Liver Diseases, and American College of Gastroenterology", Gastroenterology 142: 1592-1609, 2012.

Chen et al., "Treatment with geraniol ameliorates methionine choline-deficient diet-induced non-alcoholic steatohepatitis in rats", Journal of Gastroenterology and Hepatology 31, 1357-1365, 2015.

Cherny et al., "PBT2 Reduces Toxicity in a C. elegans Model of polyQ Aggregation and Extends Lifespan, Reduces Striatal Atrophy and Improves Motor Performance in the R6/2 Mouse Model of Huntington's Disease", Journal of Huntington's Disease, vol. 1, pp. 211-219, 2012.

Chia et al., "Incretin-Based Therapies in Type 2 Diabetes Mellitus", JCEM, vol. 93, No. 10, pp. 3703-3716, 2008.

Chitturi et al., "Etiopathogenesis of nonalcoholic steatohepatitis," Seminars in Liver Disease, 2001, 21(1):27-41.

Choe et al., "Corrigendum to 'Variants of the adiponectin gene and diabetic microvascular complications in patients with type 2 diabetes,'" Metab. Clin, Exp, 2017, 67:115.

Choe et al., "Variants of the adiponectin gene and diabetic microvascular complications in patients with type 2 diabetes," Metab. Clin, & Experimental, 2013, 62:677-85.

Choi et al., "Obesity-linked phosphorylation of PPARγ by cdk5 is a direct target of the anti-diabetic PPARγ ligands", Nature, 466, pp. 451-456, 2010.

Choi et al., "Serum adipocyte fatty acid-binding protein, retinol-binding protein 4, and adiponectin concentrations in relation to the development of the metabolic syndrome in Korean boys: a 3-y prospective cohort study", Am J ClinNutr, 93: 19-26, 2011.

Chou et al., "Adiponectin Receptor Expression in Human Malignant Tissues", Horm. Cane., 1: 136-145, 2010.

Clarke et al., Cross-Species Differential Plasma Protein Binding of MBX-102/JNJ39659100: A Novel PPAR-gamma Agonist, PPAR Res, 465715, 1-10, 2008.

Claudel et al., "The Famesoid X Receptor A Molecular Link Between Bile Acid and Lipid and Glucose Metabolism", Arterioscler Thromb Vase Biol., (10): 2020-2031, 2005.

Cohen et al., "Low LDL cholesterol in individuals of African descent resulting from frequent nonsense mutations in PCSK9", Nat. Genet, 37: 161-65, 2005.

Collino et al., "Modulation of the oxidative stress and inflammatory response by PPAR-gamma agonists in the hippocampus of rats

(56) References Cited

OTHER PUBLICATIONS exposed to cerebral ischemia/reperfusion", European Journal of Pharmacology, 530, 70-80, 2006.
Cong et al., "The establishment of a novel non-alcoholic steatohepatitis model accompanied with obesity and insulin resistance in mice," Life Sciences, 2008, 82:983-990.
Corona et al., "PPARγ as a therapeutic target to rescue mitochondrial function in neurological disease", Free Radical Biology and Medicine, 100, pp. 153-163, 2016.
Correale et al., "The blood-brain barrier in multiple sclerosis: functional roles and therapeutic targeting.", Autoimmunity, 40(2), 148-160, 2007.
Cox, "Rationally designed PPARδ-specific agonists and their therapeutic potential for metabolic syndrome", PNAS, 114 (13) 3284-3285, 2017.
Crowell et al., "Metabolic pathways link childhood adversity to elevated blood pressure in midlife adults," Obesity Research & Clinical Practice, 2016, 10:580-588.
Cusi et al., "Long-Term Piolitazone Treatment for Patients with Nonalcoholic Steatohepatits and Prediabetes or Type 2 Diabetes Mellitus", Annuals of Internal Medicine, vol. 165, No. 5, 20 pages, Sep. 6, 2016.
Cutter et al., "Development of a multiple sclerosis functional composite as a clinical trial outcome measure", BRAIN, vol. 122, pp. 871-882, 1999.
Dalamaga et al., "Adiponectin and resistin are associated with risk for myelodysplastic syndrome, independently from insulin-like growth factor-I (IGF-I) system," Eur. J. of Cancer, 2008, 44:1744-1753.
Dalamaga et al., "B-cell chronic lymphocytic leukemia risk in association with semm leptin and adiponectin: a case-control study in Greece", Cancer Causes Control, 21: 1451-1459, 2010.
Dalamaga et al., "Circulating Adiponectin and Leptin in Relation to Myelodysplastic Syndrome: A Case-Control Study", Oncology, 73: 26-32, 2007.
Dalamaga et al., "Higher fetuin-A, lower adiponectin and free leptin levels mediate effects of excess body weight on insulin resistance for myelodysplastic syndrome," Metab. Clin. & Exp., 2013, 62:1830-1839.
Dalamaga et al., "Low circulating adiponectin and resistin, but not leptin, levels are associated with multiple myeloma risk: a case-control study", Cancer Causes Control, 20: 193-199, 2009.
Dalamaga et al., "Pancreatic cancer expresses adiponectin receptors and is associated with hypoleptinemia and hyperadiponectinemia: a case-control study", Cancer Causes Control, 20: 625-633, 2009.
Dalamaga et al., "Serum adiponectin and leptin in relation to risk for preeclampsia: results from a large case-control study," Metab. Clin, and Exp., 2011, 60:1539-1544.
Dalamaga et al., "The Role of Adiponectin in Cancer: A Review of Current Evidence", Endocrine Reviews 33: 547-594, 2012.
Danese et al., "Analytical evaluation of three enzymatic assays for measuring total bile acids in plasma using a fully-automated clinical chemistry platform", PLoS One. 12(6): e0179200, 13 pages, 2017.
De Ledinghen et al., "Controlled attenuation parameter for the diagnosis of steatosis in non-alcoholic fatty liver disease", J Gastroenterol Hepatol., (4): 848-55, 2016.
Deacon et al., "Dipeptidyl Peptidase IV Inhibition Potentiates the Insulinotropic Effect of Glucagon-Like Peptide 1 in the Anesthetized Pig", Diabetes 47: 764-769, 1998.
Deacon et al., "Inhibitors of dipeptidyl peptidase IV: a novel approach for the prevention and treatment of Type 2 diabetes?", Exp. Opin. Investig. Drugs, 13: 1091-1102, 2004.
Delahanty et al., "Genetic Predictors of Weight Loss and Weight Regain After Intensive Lifestyle Modification,Metformin Treatment, or Standard Care in the Diabetes Prevention Program", Diabetes Care 35: 363-366, 2012.
Delyani, "Mineralocorticoid receptor antagonists: The evolution of utility and pharmacology", Kidney Int., 57(4): 1408-11, 2000.

Depaoli et al., "Can a selective PPARγ modulator improve glycemic control in patients with type 2 diabetes with fewer side effects compared with pioglitazone?", Jul. 2014, Diabetes Care, 37(7):1918-23, Epub Apr. 10, 2014.
Di Lascio et al., "Steato-Score: Non-Invasive Quantitative Assessment of Liver Fat by Ultrasound Imaging", Ultrasound Med Biol., 44(8): 1585-1596, 2018.
DiMasi et al., "The price of innovation: new estimates of drug development costs", J Health Econ., 22, pp. 151-185, 2003.
Ding et al., "Exendin-4, a glucagon-like protein-1 (GLP-1) receptor agonist, reverses hepatic steatosis inob/ob mice†", Hepatoiogy, 43(1): 173-81, 2006.
Disanto et al., "Serum neurofilament light chain levels are increased in patients with a clinically isolated syndrome.", J Neural. Neurosurg, Psychiatry 87(2): 126-129, 2015.
Disanto et al., "Serum Neurofilament light: A biomarker of neuronal damage in multiple sclerosis : Serum NfL as a Biomarker in MS", Annals of Neurology., vol. 81, No. 6, pp. 857-870, 2017.
Domenici et al., "Peroxisome proliferator-activated receptors alpha and gamma2 polymorphisms in nonalcoholic fatty liver disease: A study in Brazilian patients," Gene, 2013, 529:326-331.
Dongiovanni et al., "Peroxisome Proliferator-Activated Receptor Genetic Polymorphisms and Nonalcoholic Fatty Liver Disease: Any Role in Disease Susceptibility?", vol. 2013, Article ID 452061, 9 pages, 2013.
Donthamsetty et al., "Nonalcoholic steatohepatitc (NASH) mice are protected from higher hepatotoxicity of acetaminophen upon induction of PPARa with clofibrate," Toxicology and Applied Pharmacology, 2008, 230:327-337.
Doyle et al., "Biophysical signatures of noncovalent aggregates formed by a glucagonlike peptide-1 analog: A prototypical example of biopharmaceutical aggregation", J. Pharm Sci., 94(12): 2749-2763, 2005.
Drew et al., "PPAR-γ: Therapeutic Potential for Multiple Sclerosis", PPAR Research, vol. 2008, Article ID 627463, Hindawi Publishing Corporation, doi: 10.1155/2008/627463, 9 pages, 2008.
Drucker, "Enhancing incretin action for the treatment of type 2 diabetes." Diabetes Care, 26: 2929-2940, 2003.
Dufour, "NASH and thiazolidinediones: Not to be taken lightly," Journal of Hepatology, 2007, 47:451-453.
Dunn et al., "Peroxisome proliferator-activated receptor (PPAR) alpha expression in T cells mediates gender differences in development of T cell-mediated autoimmunity", J_Exp. Med., vol. 204, No. 2, 321-330, 2007.
Dunn et al., "Peroxisome proliferator-activaled receptor delta limits the expansion of pathogenic Th cells during central nervous system autoimmunity", J_Exp, Med., vol. 207, No. 8, 1599-1608, 2010.
Dunn et al., "Selective modulation of PPAR-gamma activity can lower plasma glucose without typical thiazolidinedione side-effects in patients with Type 2 diabetes", J Diabetes Complications, 25(3), 151-158, 2011.
Dunn et al., "The Gender Gap in Multiple Sclerosis", Jama Neural., 2013.
Duparc et al., "Hepatocyte MyD88 affects bile acids, gut microbiota and metabolome contributing to regulate glucose and lipid metabolism", Gut., 66: 620-632, 2017.
Dyson et al., "Non-alcoholic fatty liver disease: a practical approach to treatment", Frontline Gastroenterol., 5: 277-86, 2014.
Elbrond et al., "Pharmacokinetics, pharmacodynamics, safety, and tolerability of a single-dose of NN2211, a long-acting glucagon-like peptide 1 derivative, in healthy male subjects.", Diabetes Care., 25(8): 1398-1404, 2002.
Epstein et al., "Drug evaluation: PSN-9301, a short-acting inhibitor of dipeptidyl peptidase IV.", Curr Opin Investig Drugs, 8(4):331-337, 2007.
Eshraghian et al., "Non-alcoholic fatty liver disease and thyroid dysfunction: A systematic review", World J Gastroenterol., 20(25): 8102-8109, 2014.
European Office Action in European Application No. 11827285.5, dated Jul. 5, 2018.
European Office Action in European Application No. 14746632, dated Apr. 3, 2019, 4 pages.

(56) References Cited

OTHER PUBLICATIONS

Extended European Search Report in Application No. 17842205, dated Mar. 12, 2020, 12 pages.
Extended European Search Report in Application No. 17851479, dated May 4, 2020.
Extended European Search Report in Application No. 18741523.7, dated Jul. 16, 2020, 8 pages.
Extended European Search Report in Application No. PCT/US2016021162, dated Oct. 4, 2018, 8 pages.
Eyer and Peterson, "Neurofilament-deficient axons and perikaryal aggregates in viable transgenic mice expressing a neurofilament-β-galactosidase fusion protein", Neuron 12: 389-405, 1994.
Fargnoli et al., "Adherence to healthy eating patterns is associated with higher circulating total and high-molecular-weight adiponectin and lower resistin concentrations in women from the Nurses' Health Study", Am J Clin Nutr., 88: 1213-1224, 2008.
Fargnoli et al., "Resistin is associated with biomarkers of inflammation while total and high-molecular weight adiponectin are associated with biomarkers of inflammation, insulin resistance, and endothelial function", European Journal of Endocrinology 162, 281-288, 2010.
Farrell et al., "Nonalcoholic Fatty Liver Disease: From Steatosis to Cirrhosis", Hepatology, 43: S99-S112, 2006.
Fasting et al., "Maternal Levels of Corticotropin-Releasing Hormone during Pregnancy in Relation to Adiponectin and Leptin in Early Childhood", J Clin Endocrinol Metab 94: 1409-1415, 2009.
Feghali et al., "Cytokines in acute and chronic inflammation", Front Biosci (Landmark Ed), 2, d12-26, 1997.
Feinstein et al., "Peroxisome proliferator-activated receptor-γ agonists prevent experimental autoimmune encephalomyelitis", Ann. Neurol., vol. 51, pp. 694-702, 2002.
Feldstein et al., "Cytokeratin-18 fragment levels as noninvasive biomarkers for nonalcoholic steatohepatitis: a multicenter validation study.", Hepatology, 50(4): 1072-2078, 2009.
Fernandez-Botran R, et al., "Cytokine expression and microglial activation in progressive supranuclear palsy", Parkinsonism Relat Disord., 17(9):683-688, 2011.
Ferrer et al., "Phosphorylated map kinase (ERK.I, ERK2) expression is associated with early tau deposition in neurones and glial cells, but not with increased nuclear DNA vulnerability and cell death, in Alzheimer disease, Pick's disease, progressive supranuclear palsy and corticobasal degeneration", Brain Pathol., 11(2): 144-158, 2001.
Festuccia et al., "Peroxisome proliferator-activated receptor-gamma-mediated positive energy balance in the rat is associated with reduced sympathetic drive to adipose tissues and thyroid status", Endocrinology, 149 (5), 2121-2130, 2008.
Fialova et al., "Serum and cerebrospinal fluid light neurofilaments and antibodies against them in clinically isolated syndrome and multiple sclerosis", Journal of Neuroimmunology, vol. 262, No. 1, pp. 113-120, 2013.
Fiorenza et al., "Lipodystrophy: pathophysiology and advances in treatment", Nat. Rev. Endocrinol. 7, 137-150, 2011.
Fisher et al., "Drug metabolizing enzyme induction pathways in experimental non-alcoholic steatohepatitis", Arch Toxicol., 82: 959-964, 2008.
Ford et al., "Prevalence of the Metabolic Syndrome Among US Adults Findings From the Third National Health and Nutrition Examination Survey", JAMA, vol. 287 (3), pp. 356-359, 2002.
Fowler, Diabetes Treatment, Part 3: Insulin and Incretins. Clinical Diabetes, 26(1):35-39, 2008.
Fowler et at, "Host-derived adiponectin is tumor-suppressive and a novel therapeutic target for multiple myeloma and the associated bone disease", Blood, 118(22), 5872-5882, 2011.
Francque et al., "PPARa gene expression correlates with severity and histological treatment response inpatients with non-alcoholic steatohepatitis," Journal of Hepatology, 2015,63:164-173.
Friedrich et al., "Response of fibroblast growth factor 19 and bile acid synthesis after a body weight-adjusted oral fat tolerance test in overweight and obese NAFLD patients: a non-randomized controlled pilot trial", BA1C Gastroenterol., 76-85, 2018.
Fujita et al., "Dysfunctional Very-Low-Density Lipoprotein Synthesis and Release is a Key Factor in Nonalcoholic Steatohepatitis Pathogenesis", Hepatology, 50: 772-780, 2009.
Fujita et al., "Telmisartan, An Angiotensin II Type 1 Receptor Blocker, Controls Progress of Nonalcoholic Steatohepatitis in Rats", 52: 3455-3464, 2007.
Gaemers et al., "Lipotoxicity and steatohepatitis in an overfed mouse model for non-alcoholic fatty liver disease," Biochemica et Biophysica Acta, 2011, 1812:447-458.
Gaiottino et al., "Increased Neurofilament Light Chain Blood Levels in Neurodegenerative Neurological Diseases", PLoS ONE, vol. 8, No. 9, pp. e75091, 2013.
Gale et al., "Energy Homeostasis, Obesity and Eating Disorders: Recent Advances in Endocrinology", J. Nutr. 134: 295-298, 2004.
Garattini et al., "New approaches to cancer therapy.", Ann, Oneal., 14, pp. 813-816, 2003.
Garcia-Ruiz et al., "NADPH oxidase is implicated in the pathogenesis of oxidative phosphorylation dysfunction in mice fed a high-fat diet", Scientific Reports, 6: 23664, 13 pages, 2016.
Gasbarrino et al., "Circulating Chemerin is Associated With Carotid Plaque Instability, Whereas Resistin is Related to Cerebrovascular Symptomatology", Arterioscler Thromb Vase Biol., 36: 1670-1678, 2016.
Gastaldelli et al., "Pioglitazone in the treatment of NASH: the role of adiponectin", Aliment Pharmacol Ther, 32:769-775, 2010.
Gatta et al., "Survival of European children and young adults with cancer diagnosed 1995-2002", Eur. J Cancer, 45, pp. 992-1005, 2009.
Gavrila et al., "Diurnal and Ultradian Dynamics of Serum Adiponectin in Healthy Men: Comparison with Leptin, Circulating Soluble Leptin Receptor, and Cortisol Patterns", J Clin Endocrinol Metab 88: 2838-2843, 2003.
Gavrila et al., "Serum Adiponectin Levels Are Inversely Associated with Overall and Central Fat Distribution but Are Not Directly Regulated by Acute Fasting or Leptin Administration in Humans: Cross-Sectional and Interventional Studies", J Clin Endocrinol Metab, 88(10): 4823-4831, 2003.
George et al., "Nonalcoholic Fatty Liver Disease: Pathogenesis and Potential for Nuclear Receptors as Therapeutic Targets", Molecular Pharmaceutics, vol. 5, No. 1, 49-59, 2007.
Georgescu et al., "Angiotensin-receptor blockers as therapy for mildto-moderate hypertension-associated non-alcoholic steatohepatitis", World J Gastroenterol, 15(8): 942-954, 2009.
Gialamas et al., "Serum adiponectin levels and tissue expression of adiponectin receptors are associated with risk, stage, and grade of colorectal cancer," Metabolism Clinical and Experimental, 2011, 60:1530-1538.
Gillman et al., "Breast-feeding, Adipokines, and Childhood Obesity", Epidemiology 18: 730-732, 2007.
Gisslen et al., "Plasma Concentration of the Neurofilament Light Protein (NFL) is a Biomarker of CNS Injury in HIV Infection: A Cross-Sectional Study", EBioMedicine 3:135-140, 2016.
Godoy et al., "iNT131 increases dendritic arborization and protects against A3 toxicity by inducing mitochondrial changes in hippocampal neurons", Biochemical and Bioptiysical Research Communications, vol. 490, No. 3, pp. 955-962, 2017.
Gold et al., "Understanding pathogenesis and therapy of multiple sclerosis via animal models: 70 years of merits and culprits in experimental autoimmune encephalomyelitis research", Brain, 129, 1953-1971, 2006.
Gouni-Berthold et al., "Short-term treatment with ezetimibe, simvastatin or their combination does not alter circulating adiponectin, resistin or leptin levels in healthy men", Clinical Endocrinology 68, 536-541, 2008.
Graham et al., "Antisense inhibition of proprotein convertase subtilisin/kexin type 9 reduces serum LDL in hyperlipidemic mice", J. Lipid Res., 48: 763-67, 2007.
Grammes et al., "The PPARy agonist pioglitazone crosses the blood-brain barrier and reduces tumor growth in a human xenograft model", Cancer Chemother Pharmacol., 71(4), 929-936, 2013.

(56) References Cited

OTHER PUBLICATIONS

Gupte et al., "Rosiglitazone Attenuates Age- and Diet-Associated Nonalcoholic Steatohepatitis in Male Low-Density Lipoprotein Receptor Knockout Mice", Hepatology, 52: 2001-2011, 2010.
Hameed et al., "Emerging therapies for nonalcoholic fatty liver disease," Clin Liver Dis., 2016, 20:365-385.
Heidemann et al., "Total and High-Molecular-Weight Adiponectin and Resistin in Relation to the Risk for Type 2 Diabetes in Women", vol. 149, No. 5, 307-316, 2008.
Higgins et al., "Selective peroxisome proliferator-activated receptor gamma (PPAR-gamma) modulation as a strategy for safer therapeutic PPAR-gamma activation", Am J Clin Nutr, 91(1), 267S-272S, 2010.
Higgins et al., "The Development of INT131 as a Selective PPARγ Modulator: Approach to a Safer Insulin Sensitizer", PPAR Research vol. 2008, Article ID 936906, 9 pages, 2008.
Hinds et al., "Does bilirubin prevent hepatic steatosis through activation of the PPARa nuclear receptor?," Med. Hypth., Aug. 2016, 96:54-7.
Hivert et al., "Circulating IL-18 and the risk of type 2 diabetes in women", Diabetologia, 52: 2101-2108, 2009.
Hivert et al., "Higher Adiponectin Levels Predict Greater Weight Gain in Healthy Women in the Nurses' Health Study", Obesity, 19, 409-415, 2011.
Ho et al., "Obelicholic acid, a synthetic bile acid agonist of the farnesoid X receptor, attenuates experimental autoimmune encephalomyelitis", PNAS, vol. 113, No. 6, 1600-1605, 2016.
Hofmann et al., "Low Levels of Circulating Adiponectin Are Associated with Multiple 1\tfyeloma Risk in Ovenveight and Obese Individuals", Cancer Res, 76(7), 1935-1941, 2016.
Holst, "Treatment of Type 2 diabetes mellitus with agonists of the GLP-1 receptor or DPP-IV inhibitors", Exp. Opin. Emerg. Drugs, 9: 155-166, 2004.
Holz et al., "Glucagon-Like Peptide-1 Synthetic Analogs: New Therapeutic Agents for Use in the Treatment of Diabetes Mellitus", Chepumy, OG., Curr Med Chem., 10(22): 2471-2483, 2003.
Horton et al., "Molecular biology of PCSK9: its role in LDL metabolism", Trends Biochem. Sci., 32: 71-77, 2007.
Hossain et al., "The prevention and treatment of hypoadiponectinemia-associated human diseases by up-regulation of plasma adiponectin", Life Sciences, vol. 135, pp. 55-67, 2015.
Hsu et al., "A Carboxyl-terminal Extension of the Zinc Finger Domain Contributes to the Specificity and Polarity of Peroxisome Proliferator-activated Receptor DNA Binding", J Biol. Chem., 273(43), p. 27988-27997, 1998.
Hsu et al., "Monascin and ankaflavin act as natural AMPK activators with PPARa agonist activity to down-regulate nonalcoholic steatohepatitis in high-fat diet-fed C57BL/6 mice," Food Chem. Toxic., Nov. 2013, 64:94-103.
Huffman et al., "Abdominal Obesity, Independent from Caloric Intake, Accounts for the Development of Intestinal Tumors in Apc1638N/+ Female Mice", Cancer Prev Res; 6(3): 177-187, 2012.
Huh et al., "FNDC5 and irisin in humans: I. Predictors of circulating concentrations in serum and plasma and II. mRNA expression and circulating concentrations in response to weight loss and exercise," Metabolism, Dec. 2012, 61(12):1725-38.
Inamura et al., "Prediagnosis Plasma Adiponectin in Relation to Colorectal Cancer Risk According to KRAS Mutation Status", Jnci J Natl Cancer Inst, vol. 108, No. 4, 10 pages, 2016.
Inoue et al., "Bachl gene ablation reduces steatohepatitis in mouse MCD diet model", J. Clin Biochem. Nutr., vol. 48, No. 2, 161-166, 2011.
International Search Report and Written Opinion in International Application No. PCT/US14/12656, 5 pages, dated May 13, 2014.
International Search Report and Written Opinion in International Application No. PCT/US17/47578, dated Nov. 17, 2017, 9 pages.
International Search Report and Written Opinion in International Application No. PCT/US18/14240, dated Mar. 19, 2018, 18 pages.
International Search Report and Written Opinion in International Application No. PCT/US2009/059384, dated May 25, 2010, 13 pages.
International Search Report and Written Opinion in International Application No. PCT/US2010/044495, dated Apr. 29, 2011, 11 pages.
International Search Report and Written Opinion in International Application No. PCT/US2016/021162, 10 pages, dated May 23, 2016.
International Search Report and Written Opinion in International Application No. PCT/US2018/025923, dated Jul. 24, 2018.
International Search Report and Written Opinion in International Application No. PCT/US2019/025118, dated May 6, 2019, 18 pages.
International Search Report Cand Written Opinion in International Application No. PCT/US2011/052100, 13 pages, May 1, 2012.
Ishak et al., "Histological grading and staging of chronic hepatitis", J Hepatol., 22: 696-699, 1995.
Isreal Office Action in Application No. 248954, dated Jan. 6, 2018, 3 pages.
Japanese Office Action in Application No. 2017-566609, dated Dec. 24, 2019, English Translation, 15 pages.
Jeftic et al., "Galectin-3 Ablation Enhances Liver Steatosis, but Attenuates Inflammation and IL-33-Dependent Fibrosis in Obesogenic Mouse Model of Nonalcoholic Steatohepatitis", Mol Med., 21: 453-465, 2015.
Jeon et al., "Genistein alleviates the development of nonalcoholic steatohepatitis in ApoE-/- mice fed a high-fat diet", Mol. Nutr. Food Res., 58, 830-841, 2014.
Jha et al., "Role of Adipose Triglyceride Lipase (PNPLA2) in Protection From Hepatic Inflammation in Mouse Models of Steatohepatitis and Endotoxemia", Hepatology, 59: 858-869, 2014.
Jiang et al., "PPAR-gamma agonists inhibit production of monocyte inflammatory cytokines.", Nature, 391:82-86, 1998.
Jiang et al., "PPAR-γ agonists inhibit production of monocyte inflammatory cytokines", Nature 391: 82-86, 1998.
Jin et al., "Neuroprotective effects of PPARγ agonist rosiglitazone in N171-82Q mouse model of Huntington's disease", Journal of Neurochemistry, vol. 125, No. 3., pp. 410-419, 2013.
Joshi-Barve et al., "Alcoholic, Nonalcoholic, and Toxicant-Associated Steatohepatitis: Mechanistic Similarities and Differences", Cell Mol Gastroenterol Hepatol., 1: 356-367, 2015.
Joung et al., "Early Life Adversity is Associated With Elevated Levels of Circulating Leptin, Irisin, and Decreased Levels of Adiponectin in Midlife Adults", J Clin Endocrinol Metab, 99(6): E1055-E1060, 2014.
Kaiser et al., "A pilot test of pioglitazone as an add-on in patients with relapsing remitting multiple sclerosis", Journal of Neuroimmunology, 211, 124-130, 2009.
Kakazu et al., "The influence of pioglitazone on the plasma amino acid profile in patients with nonalcoholic steatohepatitis (NASH)", Hepatol Int., 7: 577-585, 2013.
Kaklamani et al., "Adiponectin pathway polymorphisms and risk of breast cancer in African Americans and Hispanics in the Women's Health Initiative," Breast Cancer Res. Trea., Apr. 2013, 139:461-8.
Kaklamani et al., "Polymorphisms of ADIPOQ and ADIPOR1 and prostate cancer risk," Metabolism, Sep. 2011, 60(9):1234-43.
Kaklamani et al., "Variants of the Adiponectin (ADIPOQ) and Adiponectin Receptor 1 (ADIPOR1) Genes and Colorectal Cancer Risk", JAMA., 300(13): 1523-1531, 2008.
Kaklamani et al., "Variants of the Adiponectin and Adiponectin Receptor 1 Genes and Breast Cancer Risk", Cancer Res., 68(9): 3178-84, 2008.
Kallwitz et al., "Role of peroxisome proliferators-activated receptors in the pathogenesis and treatment of nonalcoholic fatty liver disease," Worl J. Gastroenterol., Jan. 2008, 14(1): 22-8.
Kanakasabai et al., "Peroxisome proliferator-activated receptor delta agonists inhibit T helper type 1 (Th1) and Th17 responses in experimental allergic encephalomyelitis", Immunology, 130, 572-588, 2010.

(56) References Cited

OTHER PUBLICATIONS

Kang and Chen, "Curcumin eliminates oxidized LDL roles in activating hepatic stellate cells by suppressing gene expression of lectin-like oxidized LDL receptor-1," Lab. Invest., Nov. 2009, 89:1275-90.

Kang et al., "Variants of the Adiponectin and Adiponectin Receptor-1 Genes and Posttransplantation Diabetes Mellitus in Renal Allograft Recipients," J. Clin. Endocrinol. Metab., Jan. 2012, 97(1):E129-35.

Kapadia et al., "Mechanisms of anti-inflammatory and neuroprotective actions of PPAR-gamma agonists", Front Biosci.; 13: 1813-1826, 2009.

Karachialiou et al., "Real-time liquid biopsies become a reality in cancer treatment", Ann. Transl. Med, 3(3): 36, 3 pages, 2016.

Karagozian et al., "Obesity-associated mechanisms of hepatocarcinogenesis", Metabolism, 63(5), 507-617, 2014.

Karakosta et al., "Cord blood leptin levels in relation to child growth trajectories," Metabolism, Mar. 2016, 65:874-82.

Karas et al., "Relations of Plasma Total and High-Molecular-Weight Adiponectin to New-Onset Heart Failure in Adults ‡65 Years of Age (from the Cardiovascular Health Study)," Am. J. Cardiol., 2014, 113:328-34.

Karla et al., "Glucagon-like peptide-I receptor agonists in the treatment of type 2 diabetes: Past, present, and future", Indian J Endocrinol Metab., 20(2): 254-267, 2016.

Kato et al., "Therapeutic effects of angiotensin II type 1 receptor blocker, irbesartan, on non-alcoholic steatohepatitis using FLS-ob/ob male mice," Internatl. J. Mole. Med., Feb. 2012, 30:107-13.

Katsiki et al., "Non-alcoholic fatty liver disease and dyslipidemia: An update," Metabolism, May 2016, 65:1109-23.

Katsiki, "Statins in relation to adiponectin: A significant association with clinical implications,", Atherosclerosis, Aug. 2016, 253:270-2.

Kawaguchi et al., "Pioglitazone prevents hepatic steatosis, fibrosis, and enzyme-altered lesions in rat liver cirrhosis induced by a choline-deficient L-amino acid-defined diet," Biochem. Biophys. Res. Comm., 2004, 315:187-95.

Kawahara et al., "Peroxisome Proliferator-Activated Receptor γ (PPARγ)-Independent Specific Cytotoxicity against Immature Adipocytes Induced by PPARγ Antagonist T0070907," Biol. Pharm. Bull., Jun. 2013, 36(9):1428-34.

Kelesidis et al., "Adiponectin and cancer: a systematic review," Br. J. Cancer, Mar. 2006, 94:1221-5.

Khandekar et al., "Noncanonical agonist PPARγ ligands modulate the response to DNA damage and sensitize cancer cells to cytotoxic chemotherapy.", Proc. Nat. Acad Sci. USA, vol. 115, No. 3, pp. 561-566, 2018.

Kharitonenkov et al., "FGF-21 as a novel metabolic regulator", J Clin. Invest., 115:1627-1635, 2005.

Kim et al., "Development and characterization of a glucagon-like peptide 1-albumin conjugate: the ability to activate the glucagon-like peptide 1 receptor in vivo,", Diabetes 52: 751-759, 2003.

Kim et al., "Intratracheal exposure to multi-walled carbon nanotubes induces a nonalcoholic steatohepatitislike phenotype in C57BL/6J mice," Nanotoxicology, Sep. 2014, 9(5):613-23.

Kim et al., "Lifestyle modification increases circulating adiponectin concentrations but does not change vaspin concentrations," Metabolism, Jan. 2011, 60:1294-9.

Kizer et al., "Associations of Total and High-Molecular-Weight Adiponectin With All-Cause and Cardiovascular Mortality in Older Persons," Circulation, Dec. 2012, 126(25):2951-61.

Kizer et al., "Total and High-Molecular-Weight Adiponectin and Risk of Coronary Heart Disease and Ischemic Stroke in Older Adults," J. Clin. Endocrinol. Metab., Jan. 2013, 98(1):255-63.

Kizer et al., "Total and High-Molecular-Weight Adiponectin and Risk of Incident Diabetes in Older People," Diabetes Care, Feb. 2012, 35:415-23.

Kleiner et al., "Design and Validation of a Histological Scoring System for Nonalcoholic Fatty Liver Disease", Hepatology, 41: 1313-1321, 2005.

Klotz et al., "The nuclear receptor PPARgamma selectively inhibits Th17 differentiation in a T cell-intrinsic fashion and suppresses CNS autoimmunity", JEM, 206(10): 2079-2089, 2006.

Komeda, "Obesity and NASH in Japan," Hept. Res., Oct. 2005, 33:83-6.

Körner et al., "Total and High-Molecular-Weight Adiponectin in Breast Cancer: In Vitro and in Vivo Studies," J. Clin. Endocrinol. Metab., Mar. 2007, 92(3):1041-8.

Koros et al., "Interventions in progressive supranuclear palsy", Parkinsonism and Related Disorders, vol. 22, S93-S95, 2016.

Kourouma et al., "Effects of 4-nonylphenol on oxidant/antioxidant balance systeminducing hepatic steatosis in male rat," Toxicol. Rep., Oct. 2015, 2:1423-33.

Kristiansen et al., "Obese diet-induced mouse models of nonalcoholic steatohepatitis-tracking disease by liver biopsy", World J Hepatol., 8(16): 673-684, 2016.

Kuhle et al., "A comparative study of CSF neurofilament light and heavy chain protein in MS", Mult Scler 19: 1597-1603, 2013.

Kuhle et al., "Comparison of three analytical platforms for quantification of the neurofilament light chain in blood samples: ELISA, electrochemiluminescence immunoassay and Simoa.", Clin. Chem. Lab Med 54(10): 1655-1661, 2016.

Kuhle et al., "Serum neurofilament light chain in early relapsing remitting MS is increased and correlates with CSF levels and with MRI measures of disease severity", Mult. Scler. 22(12): 1550-1559, 2016.

Kummer et al., "PPARs in Alzheimer's disease", PPAR Research, ID 403896, 1-8 pages, 2008.

Kuwashiro et al., "Telmisartan improves nonalcoholic steatohepatitis in medaka (Oryzias latipes) by reducing macrophage infiltration and fat accumulation," Cell Tissue Res., Feb. 2011, 344:125-34.

Kyung-Kim et al., "PAR-1622 is a selective peroxisome proliferator-activated receptor gamma partial activator with preserved antidiabetic efficacy and broader safety profile for fluid retention", Arch Pharm Res, 32(5), 721-727, 2009.

Lake et al., "Transcription factor binding site enrichment analysis predicts drivers of altered gene expression in nonalcoholic steatohepatitis," Biochem. Pharmacol., Nov. 2016, 122:62-71.

Lalloyer et al., "Peroxisome Proliferator—Activated Receptor- Gene Level Differently Affects Lipid Metabolism and Inflammation in Apolipoprotein E2 Knock-In Mice," Arterioscler. Thromb. Vasc. Biol., Mar. 2011, 31:1573 -9.

Lanvin, "Vitamin E treatment of nonalcoholic steatohepatitis in children: A pilot study 2000", The Journal of Pediatrics; Issue 136, vol. 6, pp. 734-738, 2000.

Larter et al., "Peroxisome proliferator-activated receptor-a agonist, Wy 14 643, improves metabolic indices, steatosis and ballooning in diabetic mice with non-alcoholic steatohepatitis," J. Gastroenterol, Hepatol., Feb. 2012, 27(2):341-50.

Leclercq, "Pathogenesis of steatohepatitis : insights from the study of animal models," Acta Gastroenterol, Belg., Jan.-Mar. 2007, 70(1):25-31.

Lee et al., "Effects of leptin and adiponectin on pancreatic β-cell function," Metabolism, Apr. 2011, 60:1664-72.

Lee et al., "Selective PPARγ modulator INT131 normalizes insulin signaling defects and improves bone mass in diet-induced obese mice", Am J Physiol Endocrinol Metab, 302(5), E552-560, 2012.

Lehmann et al., "An antidiabetic thiazolidinedione is a high affinity ligand for peroxisome proliferator-activated receptor gamma (PPAR gamma)", J. Biol. Chem. 270: 12953-12956, 1995.

Lemoine et al., "Altered hepatic expression of SREBP-1 and PPARg is associated with liver injury in insulin-resistant lipodystrophic HIV-infected patients," AIDS, Sep. 2011, 20:387-95.

Lemoine et al., "Hepatic molecular effects of rosiglitazone in human non-alcoholic steatohepatitis suggest long-term pro-inflammatory damage," Heptal. Res., 2014, 44:1241-7.

Lemoine et al., "PPAR and Liver Injury in HIV-Infected Patients," PPAR Res., Jan. 2009, 2009:906167.

Leroux et al., "Toxic lipids stored by Kupffer cells correlates with their pro-inflammatory phenotype at an early stage of steatohepatitis," J. Hept., 2012, 57:141-9.

(56) References Cited

OTHER PUBLICATIONS

Li et al., "Effects of endoxins on the expression of peroxisome proliferator-activated receptor alpha in the development of nonalcoholic steatohpatitis in rats," Chin. J. Hepatol., Feb. 2006, 13(2):89-91.
Li et al., "The effects of PPAR-gamma ligand pioglitazone on platelet aggregation and arterial thrombus formation", Cardiovascular Research 65, 907-912, 2005.
Liang et al., "Salsalate attenuates diet induced non-alcoholic steatohepatitis in mice by decreasing lipogenic and inflammatory processes," Br. J. Pharmacol., Aug. 2015, 172:5293-305.
Libbey et al., "Experimental autoimmune encephalomyelitis as a testing paradigm for adjuvants and vaccines", 29(17), 3356-3362, 2011.
Lichtinghagen et al., "The Enhanced Liver Fibrosis (ELF) score: normal values, influence factors and proposed cut-off values.", J Hepatol., 59(2): 236-242, 2013.
Ligibel et al., "Impact of a mixed strength and endurance exercise intervention on levels of adiponectin, high molecular weight adiponectin and leptin in breast cancer survivors," Cancer Causes Control, May 2009, 20:1523-8.
Lin et al., "Lipid and inflammatory biomarkers and kidney function decline in type 2 diabetes," Diabetologia, Nov. 2009, 53:263-7.
Liss and Finck, "PPARs and nonalcoholic fatty liver disease," Biochimie, Dec. 2016, 136:65-74.
Liu et al., "Adiponectin administration prevents weight gain and glycemic profile changes in diet-induced obese immune deficient Rag1-/- mice lacking mature lymphocytes," Metabolism, Sep. 2016, 65:1720-30.
Liu et al., "Antioxidant Mechanisms in Nonalcoholic Fatty Liver Disease", Curr. Drug Tar., 16(12): 1301-1314, 2015.
Liu et al., "Lack of mature lymphocytes results in obese but metabolically healthy mice when fed a high-fat diet", International Journal of Obesity 39, 1548-1557, 2015.
Liu et al., "The ameliorating effect of rosiglitazone on experimental nonalcoholic steatohepatitis is associated with regulating adiponectin receptor expression in rats," Euro. J. Pharmacol., Oct. 2010, 650:384-9.
Liu et al., "The role of fibroblast growth factor 21 in the pathogenesis of non-alcoholic fatty liver disease and implications for therapy.", Metabolism, 64(3): 380-90, 2015.
Lo et al., "Adipsin is an Adipokine that Improves β Cell Function in Diabetes", Cell, 158, pp. 41-53, 2014.
Lomonaco et al., "Nonalcoholic Fatty Liver Disease: Current Issues and Novel Treatment Approaches", Drugs, 73, 1-14, 2013.
Loyer et al., "Liver microRNA-21 is overexpressed in non-alcoholic steatohepatitis and contributes to the disease in experimental models by inhibiting PPARα expression," Gut, Sep. 2015, 65:1882-94.
Lubkowska et al., "Adiponectin as a Biomarker of Osteoporosis in Postmenopausal Women: Controversies", Hindawi Publishing Corporation, Disease .Markers, vol. 2014, Article ID 975178, p. 2, 2014.
Lutchman et al., "The Effects of Discontinuing Pioglitazone in Patients with Nonalcoholic Steatohepatitis," Hepatology, 2007, 46(2):424-9.
Lv et al., "Noninvasive Quantitative Detection Methods of Liver Fat Content in Nonalcoholic Fatty Liver Disease.", J. Clin Transl Hepatol., 6(2): 217-221, 2018.
Lycke et al., "Neurofilament protein in cerebrospinal fluid: a potential marker of activity in multiple sclerosis", J Neural. Neurosurg, Psychiatry 64(3):402-404, 1998.
Ma et al., "Hepatoprotective effects of geniposide in a rat model of nonalcoholic steatohepatitis," J. Pharm, Pharmacol., Januaiy 2011, 63:587-93.
Madar et al., "Discovery of 2-[4-{{2-(2S,5R)-2-Cyano-5-ethynyl-1-pyrrolidinyl]-2-oxoethyl]amino]-4-methyl-1-piperidinyl]-4-pyridinecarboxylic Acid (ABT-279): A Very Potent, Selective, Effective, and Well-Tolerated Inhibitor of Dipeptidyl Peptidase-IV, Useful for the Treatment of Diabetes", J. Med. Chem, 49(21 ):6416-6420, 2006.

Maechiba et al., "Disposition of the new antidiabetic agent pioglitazone in rats, dogs, and monkeys", Arzneimittel-forschung, 47(1), 29-35, 1997.
Magkos and Mantzoros, "Body fat redistribution and metabolic abnormalities in HIV-infected patients on highly active antiretroviral therapy: novel insights into pathophysiology and emerging opportunities for treatment," Metabolism, 2011, 60:749-53.
Magkos et al., "Leptin replacement improves postprandial glycemia and insulin sensitivity in human immunodeficiency virus-infected lipoatrophic men treated with pioglitazone: a pilot study," Metabolism, Oct. 2010, 60:1045-9.
Maglich et al., "The nuclear receptor CAR (NR1i3) regulates serum triglyceride levels under conditions of metabolic stress," J. Lipid Res., Oct. 2008, 50:439-45.
Mamalakis et al., "Depression and serum adiponectin and adipose omega-3 and omega-6 fatty acids in adolescents", Pharmacology, Biochemistiy and Behavior 85, 474-479, 2006.
Mantzoros et al., "Adherence to the Mediterranean dietary pattern is positively associated with plasma adiponectin concentrations in diabetic women1-3," Am. J. Clin. Nutr., 2006, 84:328-35.
Mantzoros et al., "Adiponectin and Breast Cancer Risk," J. Clin. Endocrinol. Metab., Mar. 2004, 89(3):1102-7.
Mantzoros et al., "Circulating Adiponectin Levels Are Associated with Better Glycemic Control, More Favorable Lipid Profdle, and Reduced Inflammation in Women with Type 2 Diabetes," J. Clin. Endcorinol, Metab., Aug. 2005, 90(8):4542-8.
Mantzoros et al., "Cord Blood Leptin and Adiponectin as Predictors of Adiposity in Children at 3 Years of Age: A Prospective Cohort Study," Pediatrics, 2009, 123:682-9.
Mantzoros et al., "Maternal diet and cord blood leptin and adiponectin concentrations at birth", Clinical Nutrition 29, 622-626, 2010.
Mantzoros et al., "Serum adiponectin concentrations in relation to maternal and perinatal characteristics innewbomsm" Eur. J. Endocrinol., 2004, 151:741-6.
Marino et al., "Glucocorticoid Receptor Induces Hepatic Steatosis by Augmenting Inflammation and Inhibition of the Peroxisome Proliferator-activated Receptor (PPAR)", The Journal of Biological Chemistry vol. 291, No. 50, pp. 25776-25788, 2016.
Martinez et al., "A mechanistic approach to understanding the factors affecting drug absorption: A review of fundamentals", J Clin Pharmacol 42; 620-643, 2002.
Mas et al., "IL-6 Deficiency Attenuates Murine Diet-Induced Non-Alcoholic Steatohepatitis," PLoS One, Nov. 2009, 4(11):e7929.
Maso et al., "Circulating Adiponectin and Endometrial Cancer Risk", J Clin Endocrinol Metab 89: 1160-1163, 2004.
Maso et al., "Relationship between a wide range of alcohol consumptions, components of the insulin-like growth factor system and adiponectin", European Journal of Clinical Nutrition, 61,221-225, 2007.
Matarese et al., "Leptin and Adipocytokines: Bridging the Gap Between Immunity and Atherosclerosis", Current Pharmaceutical Design, 13, 3676-3680, 2007.
Matsunami et al., "Regulation of synthesis and oxidation of fatty acids by adiponectin receptors (AdipoR1/R2) and insulin receptor substrate isoforms (IRS-1/-2) of the liver in a nonalcoholic steatohepatitis animal model", Metabolism Clinical and Experimental 60, 805-814, 2011.
McPherson et al., "Simple non-invasive fibrosis scoring systems can reliably exclude advanced fibrosis inpatients with non-alcoholic fatty liver disease", Gut, 59 (9): 1265-1269, 2010.
Melistas et al., "Association of the C45TOG and C276GOT polymorphisms in the adiponectin gene with insulin resistance in nondiabetic Greek women," Eur. J. Endocrinol., 2009, 161:845-52.
Mencarelli et al., "VSL#3 Resets Insulin Signaling and Protects against NASH and Atherosclerosis in a Model of Genetic Dyslipidemia and Intestinal Inflammation," PLoS One, Sep. 2012, 7(9):e45425.
Mergulhao et al., "Recombinant protein secretion in *Escherichia coli*", Biotechnol. Advances 23: 177-202, 2005.
Mexican Office Action in Mexican Application No. MX/a/2013/003160, dated Apr. 13, 2018, 5 pages.
Michalakis et al., "In prostate cancer, low adiponectin levels are not associated with insulin resistance," Eur. J. Clin. Invest. 45:572-8.

(56) References Cited

OTHER PUBLICATIONS

Michalakis et al., "Seram Adiponectin Concentrations and Tissue Expression of Adiponectin Receptors Are Reduced in Patients with Prostate Cancer: A Case Control Study," Cancer Epidemiol., Biomarkers Prev., Febraaty 2007, 16(2):308-13.
Miller et al., "A Controlled Trial of Natalizumab for Relapsing Multiple Sclerosis", The New England Journal of Medicine, vol. 348, pp. 15-23, 2003.
Miller et al., "Efficacy of six months' therapy with oral rosiglitazone maleate in relapsingremitting multiple sclerosis, 1 oth Annual Meeting of the Americas Committee for Treatment and Research in Multiple Sclerosis", 1 page, 2005.
Minagar et al., "Blood-brain barrier disruption in multiple sclerosis", Multi Seier, 9(6), 540-549, 2003.
Mintziori et al., "Emerging and future therapies for nonalcoholic steatohepatitis in adults", Expert Opinion on Pharmacotherapy, 17:14, 1937-1946, 2016.
Mishra et al., "Current Treatment Strategies for Non-Alcoholic Fatty Liver Disease (NAFLD)", Current Drag Discoveiy Technologies, 4, 133-140, 2007.
Mitsiades et al., "Circulating Adiponectin is Inversely Associated with Risk of Thyroid Cancer: In Vivo and in Vitro Studies", J Clin Endocrinol Metab, 96(12): E2023-E2028, 2011.
Miyamura et al., "Drug-induced Nonalcoholic Steatohepatitis", Yakugaku Zasshi, 136(4) 579-582, 2016.
Mokhtari et al., "Combination therapy in combating cancer.", Oncotarget, vol. 8, No. 23, p. 38022-38043, 2017.
Molica et al., "Does adiponectin act as an antiangiogenic factor in B-ceH chronic lymphocytic leukemia?", Adv Hematol., 2009: 287974, 6 pages 2009.
Monzillo et al., "Effect of Lifestyle Modification on Adipokine Levels in Obese Subjects with Insulin Resistance", Resistance. Obes Res., 11: 1048-1054, 2003.
Moon et al., "Adiponectin and metformin additively attenuate IL lb-induced malignant potential of colon cancer", Endocrine-Related Cancer 20, 849-859, 2013.
Moon et al., "Amylin-induced downregulation of hippocampal neurogenesis is attenuated by leptin in a STAT3/AMPK/ERK-dependent manner in mice", Diabetologia, 56: 627-634, 2013.
Moon et al., "Direct Role of Adiponectin and Adiponectin Receptors in Endometrial Cancer: In Vitro and Ex Vivo Studies in Humans", Mol Cancer Ther; 10(12); 2234-2243, 2011.
Moon et al., "Salutary effects of adiponectin on colon cancer: in vivo and in vitro studies in mice", Gut., 62: 561-570, 2013.
Motani et al., "A selective modulator of PPARy", J Mal. Biol., 386(5), 1301-1311, 2009.
Mukundan et al., "PPAR-delta senses and orchestrates clearance of apoptotic cells to promote tolerance", Nat Med., 15(11): 1266-1272, 2009.
Musso et al., "Impact of current treatments on liver disease, glucose metabolism and cardiovascular risk in non-alcoholic fatty liver disease (NAFLD): a systematic review and meta-analysis of randomised trials", Diabetologia, 55(4), 885-904, 2012.
Musso et al., "New Pharmacologic Agents That Target Inflammation and Fibrosis in Nonalcoholic Steatohepatitis-Related Kidney Disease", Clinical Gastroenterology and Hepatology 15: 972-985, 2017.
Nagasawa et al., "Effects of bezafibrate, PPAR pan-agonist, and GW501516, PPARδ agonist, on development of steatohepatitis in mice fed a methionine- and choline-deficient diet", European Journal of Pharmacology 536, 182-191, 2006.
Nagaya et al., "Mechanism of the development of nonalcoholic steatohepatitis after pancreaticoduodenectomy", BBA Clinical 3, 168-174, 2015.
Nakagami et al., "Nifedipine prevents hepatic fibrosis in a non-alcoholic steatohepatitis model induced by an L-methionine-and choline-deficient diet", Molecular Medicine Reports 5: 37-40, 2012.
Nakagami et al., "Prevention and regression of non-alcoholic steatohepatitis (NASH) in a rat model by metabosartan, telmisartan", International Journal of Molecular Medicine 26: 477-481, 2010.
Nakagami et al., "The roles of PPARs in digestive diseases", NiPPon Rinsho, vol. 63, No. 4, 665-671, 2005.
Nakajima et al., "The roles of PPARs in digestive diseases" 63(4): 665-671, 2005.
Nakayama et al., "Effects of adiponectin transgenic expression in liver of nonalcoholic steatohepatitis model mice", Metabolism Clinical and Experimental 58, 901-908, 2009.
Nan et al., "Rosiglitazone prevents nutritional fibrosis and steatohepatitis in mice", Scandinavian Journal of Gastroenterology, 44: 358-365, 2009.
Natarajan et al., "Peroxisome proliferator-activated receptor-gamma agonists inhibit experimental allergic encephalomyelitis by blocking IL-12 production, IL-12 signaling and Th1 differentiation", Genes & Immunity, 3: 59-70, 2002.
Nauck et al., "Gastric Inhibitory Polypeptide and Glucagon-Like Peptide-1 in the Pathogenesis of Type 2 Diabete.", Diabetes, 53 (Suppl. 3):S 190-196, 2004.
Naumann et al., "A simple synthesis of dihydroxybipyridyls", Synthesis 4: 279-281, 1990.
Neuman et al., "Biomarkers in Nonalcoholic Fatty Liver Disease", Can J Gastroenterol Hepatol., 28(11): 607-618, 2014.
Neuschwander-Tetri et al., "Famesoid X nuclear receptor ligand obeticholic acid for non-cirrhotic, non-alcoholic steatohepatitis (FLINT): a multicentre, randomised, placebo-controlled trial", Lancet, 385(9972), 956-965, 2014.
Neuschwander-Tetri et al., "Improved Nonalcoholic Steatohepatitis After 48 Weeks of Treatment With the PPAR-y Ligand Rosiglitazone", Hepatology 38: 1008-1017, 2003.
Neuschwander-Tetr et al., "Interim results of a pilot study demonstrating the early effects of the PPAR-g ligand rosiglitazone on insulin sensitivity, aminotransferases, hepatic steatosis and body weight in patients with non-alcoholic steatohepatitis", Journal of Hepatology 38, 434-440, 2003.
Ng et al., "Potential Neuroprotective Effects of Adiponectin in Alzheimer's Disease",International Journal of Molecular Sciences, vol. 18, No. 3, 592, 13 pages, 2017.
Nordhoff et al., "The reversed binding of β-phenethylamine inhibitors of DPP-IV: X-ray structures and properties of novel fragment and elaborated inhibitors", Bioorganic Medical Chemistry Leiters 16: 1744-1748, 2006.
Novakova et al., "Monitoring disease activity in multiple sclerosis using serum neurofilament light protein", Neurology, vol. 89, No. 22, pp. 2230-2237, 2017.
Nozaki et al., "Deficiency of iNOS-derived NO accelerates lipid accumulation-independent liver fibrosis in nonalcoholic steatohepatitis mouse model", BMC Gastroenterology, 15: 42, 14 pages, 2015.
Odetti et al., "Lipoperoxidation is selectively involved in progressive supranuclear palsy", J Neuropathol Exp Neural., 59(5):393-397, 2000.
Ogasawara et al., "A novel and comprehensive mouse model of human non-alcoholic steatohepatitis with the full range of dysmetabolic and histological abnormalities induced by gold thioglucose and a high-fat diet", vol. 31, Issue 4, 542-551, 2011.
Ohara et al., "Neurofilament Deficiency in Quaff Caused by Nonsense Mutation in Neurofilament-L Gene", J Cell Biol. 121: 387-395, 1993.
Ono et al., "Bofutsushosan, a Japanese herbal (Kampo) medicine, attenuates progression of nonalcoholic steatohepatitis in mice", J Gastroenterol, 49: 1065-1073, 2014.
Ota et al., "Insulin Resistance Accelerates a Dietary Rat Model of Nonalcoholic Steatohepatitis", Gastroenterology, 132: 282-293, 2007.
Park et al., "Adiponectin as an Anti-fibrotic and Anti-inflammatory Adipokine in the Liver", Curr Pathobiol Rep., 3( 4): 243-252, 2015.
Park et al., "Circulating Irisin in Relation to Insulin Resistance and the Metabolic Syndrome", J Clin Endocrinol Metab, 98(12): 4899-4907, 2013.
Park, "Current status of liver disease in Korea: Nonalcoholic fatty liver disease", Korean J. Hepatol., 15(Suppl 6): S34-S39, 2009.
Paruthi et al., "Adipokines in the HIV/HAART-associated lipodystrophy syndrome", Metabolism Clinic and Experimental 62, 1199-1205, 2013.
Pawella et al., "Perilipin discerns chronic from acute hepatocellular steatosis", Journal of Hepatology, vol. 60, 633-642, 2014.

(56) References Cited

OTHER PUBLICATIONS

Pawlak et al., "Molecular mechanism of PPARa action and its impact on lipid metabolism, inflammation and fibrosis in non-alcoholic fatty liver disease", Journal of Hepatology, vol. 62, 720-733, 2015.
Pawlak et al., "The Transrepressive Activity of Peroxisome Proliferator-Activated Receptor Alpha is Necessaiy and Sufficient to Prevent Liver Fibrosis in Mice", Hepatology 60: 1593-1606, 2014.
Pazaitou-Panayiotou et al., "Serum Adiponectin and Insulin-Like Growth Factor 1 in Predominantly Female Patients With Thyroid Cancer: Association With the Histologic Characteristics of the Tumor",EndocrPract., 22: 68-75, 2016.
Pederson et al., "Improved Glucose Tolerance in Zucker Fatty Rats by Oral Administration of the Dipeptidyl Peptidase IV Inhibitor Isoleucine Thiazolidide", Diabetes 47: 1253-1258, 1998.
Pei et al., "Discovery of ((4R,5S)-5-amino-4-(2,4,5-trifluorophenyl)cyclohex-l-enyl)-(3-(trifluoromethyl)-5,6-dihydro-[1,2,4]triazolo[4,3-a]pyrazin-7(8H)-yl)methanone (ABT-341), a highly potent, selective, orally efficacious, and safe dipeptidyl peptidase IV inhibitor for the treatment of type 2 diabetes.", J. Med. Chem., 49(22): 6439-6442, 2006.
Perez et al., "Bile-acid-induced cell injury and protection.", World J Gastroenterol., 15(14): 1677-1689, 2009.
Perng et al., "A prospective study of maternal prenatal weight and offspring cardiometabolic health in midchildhood", Annals of Epidemiology 24, 793-800, 2014.
Pershadsingh et al., "Effect of pioglitazone treatment in a patient with secondary multiple sclerosis", Journal of Neuroinflammation, 1: 3, 4 pages, 2004.
Perumpail et al., "Clinical epidemiology and disease burden of nonalcoholic fatty liver disease.", World J Gastroenterol., 23(47): 8263-8438, 2017.
Petridou et al., "Adiponectin in relation to childhood myeloblastic leukaemia", British Journal of Cancer, 94, 156-160, 2006.
Petridou et al., "Blackwell Publishing, Ltd. Neonatal leptin levels are strongly associated with female gender, birth length, IGF-I levels and formula feeding", Clinical Endocrinology, 62, 366-371, 2005.
Petridou et al., "Circulating Adiponectin Levels and Expression of Adiponectin Receptors in Relation to Lung Cancer: Two Case-Control Studies", Oncology, 73: 261-269, 2007.
Petridou et al., "Growth velocity during the first postnatal week of life is not related to adiponectin or leptin", Paediatric and Perinatal Epidemiology, 18, 395, 2004.
Petridou et al., "Insulin resistance: an independent risk factor for lung cancer?", Metabolism Clinic and Experimental 60, 1100-1106, 2011.
Petridou et al., "Neonatal leptin levels are strongly associated with female gender, birth length, IGF-I levels and formula feeding", Clinical Endocrinology, 62, 366-371, 2005.
Petridou et al., "Plasma Adiponectin Concentrations in Relation to Endometrial Cancer: A Case-Control Study in Greece", J. Clin. Endocrinol Metab 88: 993-997, 2003.
Petridou et al., "Serum Adiponectin as a Predictor of Childhood Non-Hodgkin's Lymphoma:ANationwide Case-Control Study", J Clin Oncol 27: 5049-5055, 2009.
Piguet et al., "Hypoxia aggravates non-alcoholic steatohepatitis in mice lacking hepatocellular PTEN", Clinical Science, 118, 401-410, 2010.
Polyzos et al., "Activin A and follistatin in patients with nonalcoholic fatty liver disease", Metabolism, 2016, 65:1550-1558.
Polyzos et al., "Adipocytokines and cytokeratin-18 in patients with nonalcoholic fatty liver disease: Introduction of CHA index", vol. 12 No.5, 749-757, 2013.
Polyzos et al., "Adipokines in nonalcoholic fatty liver disease," Metabolism, 2016, 65:1062-1079.
Polyzos et al., "Adiponectin as a potential therapeutic agent for nonalcoholic steatohepatitis", Hepatology Research, 40: 446-447, 2010.
Polyzos et al., "Adiponectin as a target for the treatment of nonalcoholic steatohepatitis with thiazolidinediones: A systematic review," Metabolism, 2016, 65:1297-1306.
Polyzos et al., "Adiponectin in non-alcoholic fatty liver disease treatment: therapeutic perspectives and unresolved dilemmas", Int J Clin Pract, 65, 3, 372-374, 2011.
Polyzos et al., "Adipose tissue, obesity and non-alcoholic fatty liver disease," Minerva Endocrinologica, Jun. 2017, 42(2):92-108.
Polyzos et al., "Circulating leptin in non-alcoholic fatty liver disease: a systematic review and meta-analysis", Diabetologia 59: 30-43, 2016.
Polyzos et al., "Irisin in patients with nonalcoholic fatty liver disease," Metabolism, 2014, 63:207-217.
Polyzos et al., "Leptin in nonalcoholic fatty liver disease: A narrative review," Metabolism, 2015, 64:60-78.
Polyzos et al., "Necessity for timely noninvasive diagnosis of nonalcoholic fatty liver disease", Metabolism, 63(2), 161-167, 2014.
Polyzos et al., "Nonalcoholic Fatty Liver Disease: The Pathogenetic Roles of Insulin Resistance and Adipocytokines", Current Molecular Medicine 9, 299-314, 2009.
Polyzos et al., "Nonalcoholic fatty liver disease: Updates on associations with the metabolic syndrome and lipid profile and effects of treatment with PPAR-γ agonists," Metabolism, 2017, 66:64-68.
Polyzos et al., "Nonlinear Distribution of Adiponectin in Patients With Nonalcoholic Fatty Liver Disease Limits Its Use in Linear Regression Analysis", J Clin Gastroenterol vol. 44, No. 3, 229-230, Mar. 2010.
Polyzos et al., "Serum total adiponectin in nonalcoholic fatty liver disease: a systematic review and meta-analysis," Metabolism, 2011, 60:313-326.
Polyzos et al., "The multi-hit process and the antagonistic roles of tumor necrosis factor-alpha and adiponectin in non alcoholic fatty liver disease", Hippokratia 13, 2: 127-128, 2009.
Polyzos et al., "The role of adiponectin in the pathogenesis and treatment of non-alcoholic fatty liver disease", Diabetes, Obesity and Metabolism, 12, 365-383, 2010.
Polyzos, "Adiponectin in Health and Disease: Current Evidence and Therapeutic Perspectives," Current Medicinal Chemistiy, 2012, 19(32):5425.
Portincasa et al., "Current Pharmacological Treatment of Nonalcoholic Fatty Liver," Current Medicinal Chemistiy, 2006, 13:2889-2900.
Poste et al., "Lipid Vesicles as Carriers for Introdzhg Biologically Active Materials into Cells", Prescott, Ed., Methods in Cell Biology, vol. XIV, Academic Press, New York, N.Y., p. 33, Chapter 4 , 1976.
Powell et al., "LX2761, a Sodium/Glucose Cotransporter 1 Inhibitor Restricted to the Intestine, Improves Glycemic Control in Mice", J Pharmacol Exp Ther., 362(1): 85-97, 2017.
Qi et al., "Adiponectin Genetic Variability, Plasma Adiponectin, and Cardiovascular Risk in Patients With Type 2 Diabetes", Diabetes 55: 1512-1516, 2006.
Qi et al., "Dietary Fibers and Glycemic Load, Obesity, and Plasma Adiponectin Levels in Women With Type 2 Diabetes", Diabetes Care 29: 1501-1505, 2006.
Racke et al., "PPARs in Neuroinflammation", PPAR Research, vol. 2008, Article ID 638356, Hindawi Publishing Corporation, 2008.
Raji et al., "Insulin Resistance and Vascular Dysfunction in Nondiabetic Asian Indians", J Clin Endocrinol Metab 89: 3965-3972, 2004.
Ratziu et al., "Elafibranor, an Agonist of the Peroxisome Proliferator-Activated Receptor-α and -δ, Induces Resolution of Nonalcoholic Steatohepatitis Without Fibrosis Worsening", Gastroenterology, vol. 150, Issue 5, pp. 1147-1159.e5, 2016.
Ratziu et al., "Nonalcoholic steatohepatitis," Ann. Endocrinol., 2005, 66(2 Pt2):1S71-1S80.
Reddy et al., "Clinical and genetic predictors of weight gain in patients diagnosed with breast cancer," Br. J. Cancer, Aug. 2013, 109:872-81.
Reeder et al., "Quantitative assessment of liver fat with magnetic resonance imaging and spectroscopy", J Magn Reson Imaging., 34, 4, 729-749, 2011.
Remingtons Pharmaceutical Sciences, 18th Ed., Mack Publishing, Easton PA, 13 pages, 1990, Table of Contents.

(56) References Cited

OTHER PUBLICATIONS

Remington's The Science and Practice of Pharmacy, 21st Ed, 4 pages, 2005, Table of Contents.
Ricote et al., "The peroxisome proliferator-activated receptor-gamma is a negative regulator of macrophage activation.", Nature, 391: 79-82, 1998.
Rigby et al., "Smooth centile curves for skew and kurtotic data modelled using the Box-Cox power exponential distribution.", Stat Med 23: 3053-3076, 2004.
Rissin et al., "Single-Molecule enzyme-linked immunosorbent assay detects serum proteins at subfemtomolar concentrations", Nat Biotechnol 28: 595-599, 2010.
Rivera et al., "Toll-Like receptor-2 deficiency enhances non-alcoholic steatohepatitis" BMC Gastroenterol., 2010, 10:52.
Rohrer et al., "Serumneurofilamentlightchainproteinis a measure of disease intensity in frontotemporal dementia", Neurology 87(13): 1329-1336, 2016.
Rojas et al., "Plasma neurofilament light chain predicts progression in progressive supranuclear palsy", Annals of Clin. and Trans., Neurology, vol. 3, No. 3, pp. 216-225, 2016.
Ronis et al., "Global Deletion of Glutathione S-Transferase A4 Exacerbates Developmental Nonalcoholic Steatohepatitis," The American Journal of Pathology, Feb. 2017, 187(2)418-430.
Ronis et al., "Medium chain triglycerides dose-dependently prevent liver pathology in a rat model of non-alcoholic fatty liver disease," Exper.Biol. Med., 2013, 238:151-62.
Rosenstock et al., "Efficacy and Safety of the Dipeptidyl Peptidase-4 Inhibitor Sitagliptin Added to Ongoing Pioglitazone Therapy in Patients with Type 2 Diabetes: A 24-Week, Multicenter, Randomized, Double-Blind, Placebo-Controlled, Parallel-Group Study", Clinical Therapeutics, vol. 28, No. 10, ages 1556-1568, 2006.
Rossi et al., "Neuroinflammation drives anxiety and depression in relapsing-remitting multiple sclerosis"; Neurology; vol. 89, pp. 1338-1347, 2017.
Roth et al., "Vitamin D Deficiency in Obese Rats Exacerbates Nonalcoholic Fatty Liver Disease and Increases Hepatic Resistin and Toll-Like Receptor Activation," Hepatology, Apr. 2012, 55(4): 1103-11.
Ruschke et al., "Gene expression of PPARg and PGC-la in human omental and subcutaneous adipose tissues is related to insulin resistance markers and mediates beneficial effects of physical training," Eur. J. Endocrinol., 2010, 162:515-23.
Rusli et al., "Fibroblast growth factor 21 reflects liver fat accumulation and dysregulation of signalling pathways in the liver of C57BL/6J mice", Sci. Rep., 29: 1-16, 2016.
Sahebkar et al., "New peroxisome proliferator-activated receptor agonists: potential treatments for atherogenic dlyslipidemia and non-alcoholic fatty liver disease", Expert Opin Pharmacother, 15(4), 493-503, 2014.
Sahin-Efe et al., "Advances in adipokines," Metabolism, 2012, 61:1659-1665.
Sanyal et al., "Piolitazone, Vitamin E, or Placebo for Nonalcoholic Steatohepatits", The New England Journal of Medicine, pp. 1675-1685, 2010.
Sarafidis et al., "Protection of the kidney by thiazolidinediones: An assessment from bench to bedside", Kidney International, 206, 70: 1223-1233, 2006.
Sasaki et al., "Aggregate formation and phosphorylation of neurofilament-L Pro22 Charcot-Marie-Tooth disease mutants", Hum. Mal .Genet. 15: 943-952, 2006.
Satapathy et al., "Epidemiology and Natural History of Nonalcoholic Fatty Liver Disease.", Semin Liver Dis., 3 5(3): 221-235, 2015.
Scheen, "Cardiovascular Effects of New Oral Glucose-Lowering Agents", Circ Res 122: 1439-1459, 2018.
Scheer et al., "Day/night variations of high-molecular-weight adiponectin and lipocalin-2 in healthy men studied under fed and fasted conditions," Diabetologia, 2010, 53:2401-5.
Schmidt et al., "Anti-inflammatory and antiproliferative actions of PPAR-y agonists on T lymphocytes derived from MS patients", Journal of Leukocyte Bilogy, vol. 75, 2004.
Schreuder et al., "The hepatic response to FGF19 is impaired in patients with nonalcoholic fatty liver disease and insulin resistance.", Gastrointest., Physiol., 2010, 298: G440-445, 2010.
Schultz et al., "Hepatic Adverse Effects of Fructose Consumption Independent of Overweight/Obesity," Int. J. Mol, Sci., 2013, 14:21873-86.
Scorletti et al., "Omega-3 Fatty Acids, Hepatic Lipid Metabolism, and Nonalcoholic Fatty Liver Disease", Ann. Rev. Nutr., 33, 231-248, 2013.
Sebokova et al., "Dipeptidyl Peptidase IV Inhibitors: The Next Generation of New Promising Therapies for the Management of Type 2 Diabetes", Current Topics in Medicinal Chemistry 7: 547-555, 2007.
Seidah et al., "The secretory proprotein convertase neural apoptosis-regulated convertase 1 (NARC-1): Liver regeneration and neuronal differentiation", Proc. Nat. Acad Sci. USA, 100: 928-33, 2003.
Serviddio et al., "Free radical biology for medicine: learning from nonalcoholic fatty liver disease," Free Radical Biology and Medicine, 2013, 65:952-968.
Seth et al., "Environmental Toxin-Linked Nonalcoholic Steatohepatitis and Hepatic Metabolic Reprogramming in Obese Mice," Toxicological Sci., 2013, 134(2):291-303.
Shah et al., "MicroRNAs in Liver Disease: Bench to Bedside," Journal of Clinical and Experimental Hepatology, Sep. 2013, 3(3):231-242.
Shalini et al., "Old, new and emerging functions of caspases", Cell Death Differ., 22(4): 526-539, 2015.
Shapiro and Bruck, "Therapeutic potential of curcumin in non-alcoholic steatohepatitis," Nutr. Res. Rev., 2005, 18:212-21.
Sharma et al., "The Riddle of Nonalcoholic Fatty Liver Disease: Progression From Nonalcoholic Fatty Liver to Nonalcoholic Steatohepatitis," Journal of Clinical and Experimental Hepatology, Jun. 2015, 5(2):147-158.
Shea et al., "Independent Circadian and Sleep/Wake Regulation of Adipokines and Glucose in Humans," J. Clin. Endocrinol, Metab., May 2005, 90(5):2537-44.
Sher et al., "Relationship Between Serum Adiponectin and Prostate Cancer Grade," The Prostate, 2008, 68:1592-8.
Shetty et al., "Circulating Adiponectin and Resistin Levels in Relation to Metabolic Factors, Inflammatory Markers, and Vascular Reactivity in Diabetic Patients and Subjects at Risk for Diabetes," Diabetes Care, Oct. 2004, 27(10):2450-7.
Shi et al., "Effects of apigenin on protein expressions of PPARs in liver tissues of rats with nonalcoholic steatohepatitis," Clin. J. Hepatol., Feb. 2015, 23(2):124-9.
Shi, "Caspase Activation: Revisiting the Induced Proximity Model", Cell, 117(7): 855-858, 2004.
Shieh et al., "Increase of hepatic fat accumulation by liver specific expression of Hepatitis B virus X protein in zebrafish," Biochimica et Biophysica Acta, 2010, 1801:721-730.
Shih et al., "Synergistic Effect of Cyanidin and PPAR Agonist against Nonalcoholic Steatohepatitis-Mediated Oxidative Stress-Induced Cytotoxicity through MAPK and Nrf2 Transduction Pathways," J. Agric. Food Chem., 2012, 2924-33.
Shinoda et al., "Regulation of bone formation by adiponectin through autocrine/paracrine and endocrine pathvvays," Journal of Cellular Biochemistiy, vol. 99, No. 1, pp. 196-208, 2006.
Shiri-Sverdlov et al., "Early diet-induced non-alcoholic steatohepatitis in APOE2 knock-in mice and its prevention by fibrates," Journal of Hepatology, 2006, 44:732-741.
Sleilati et al., "Efficacy and safety of pioglitazone in treatment of a patient with an atypical partial lipodystrophy syndrome.", Pioglitazone and Lipodystrophy, Endocr Pract., vol. 13, No. 6, pages 656-661, 2007.
Smith et al., "Clinical worsening in multiple sclerosis is associated with increased frequency and area of gadopentetate dimeglumine-enhancing magnetic resonance imaging lesions", Ann Neurol, 33(5), 480-489, 1993.

(56) References Cited

OTHER PUBLICATIONS

Sohn et al., "Lactobacillus paracasei Induces M2-Dominant Kupffer Cell Polarization in a Mouse Model of Nonalcoholic Steatohepatitis," Dig. Dis. Sci., 2015, 60:3340-50.
Sorrentino et al., "A clinical-morphological study on cholestatic presentation of nonalcoholic fatty liver disease.", Dig Dis Sci., 50(6): 1130-1135, 2005.
Souza-Mello, "Peroxisome proliferator-activited receptors as targets to treat non-alcoholic fatty liver disease", World J Hepatol., 7(8): 1012-1019, 2015.
Spyridopoulos et al., "Low adiponectin levels are associated with renal cell carcinoma: A case-control study," Int. J. Cancer, 2007, 120:1573-8.
Staels et al., "Hepatoprotective Effects of the Dual Peroxisome Proliferator-Activated Receptor Alpha/Delta Agonist, GFT505, in Rodent Models of Nonalcoholic Fatty Liver Disease/Nonalcoholic Steatohepatitis," Hepatology, Dec. 2013, 58:1941-52.
Stefano et al., "Nonalcoholic Steatohepatitis (NASH) in OB/OB Mice Treated with Yo Jyo Hen Shi Ko (YHK): Effects on Peroxisome Proliferator-Activated Receptors (PPARs) and Microsomal Triglyceride Transfer Protein (MTP)," Dig, Dis. Sci. 2007, 52:3448-54.
Steinman et al., "Piet Mondrian's trees and the evolution in understanding multiple sclerosis, Charcot Prize Lecture 2011", Multiple Sclerosis Journal, 19(1), 5-14, 2012.
Steinman et al., "Virtues and pitfalls of EAE for the development of therapies for multiple sclerosis", Trends in Immunology, vol. 26, No. 11, 2005.
Stephen et al., "Nonalcoholic Fatty Liver Disease and Bariatric Surgery", Expert Rev Gastroenterol Hepatol, 5(2): 163-171, 2012.
Storer et al., "Peroxisome proliferator-activated receptor-gamma agonists inhibit the activation of microglia and astrocytes: Implications for multiple sclerosis", Journal of Neuroimmunology, vol. 161, pp. 113-122, 2005.
Strum et al., "Rosiglitazone induces mitochondrial biogenesis in mouse brain", 11 (1), 45-51, 2007.
Stuebe et al., "Duration of Lactation and Maternal Adipokines at 3 Years Postpartum," Diabetes, Apr. 2011, 60:1277-85.
Stuebe et al., "Gestational Glucose Tolerance and Maternal Metabolic Profile at 3 Years Postpartum," Obsterics & Gynecology, Nov. 2011, 118(5):1065-1073.
Su et al., "A novel therapy for colitis utilizing PPARgamma ligands to inhibit the epitheliah inflammatory response", The Journal of Clinical Investigation, vol. 104, No. 4, 1999.
Sumida et al., "Current and future pharmacological therapies for NAFLD/NASH", J Gastroenterol., 53: 362-376, 2018.
Sun et al., "Leptin and Soluble Leptin Receptor Levels in Plasma and Risk of Type 2 Diabetes in U.S. Women," Diabetes, Mar. 2010, 59:611-8.
Svegliati-Baroni et al., "A Model of Insulin Resistance and Nonalcoholic Steatohepatitis in Rats," The American Journal of Pathology, Sep. 2006, 169(3):846-860.
Svegliati-Baroni et al., "Glucagon-like peptide-lreceptor activation stimulates hepatic lipid oxidation and restores hepatic signalling alteration induced bya high-fat diet in nonalcoholic steatohepatitis," Liver Internatl., 2011, 31(9)1285-97.
Sweeney et al., "The role of adipokines in relation to HIV lipodystrophy," AIDS, 2007, 21:895-904.
Tacke, "Cenicriviroc for the treatment of non-alcoholic steatohepatitis and liver fibrosis.", Expert Opin Investig Drugs, 27(3): 301-311, 2018.
Tahan et al., "Rosiglitazone Attenuates Liver Inflammation in a Rat Model of Nonalcoholic Steatohepatitis," Dig. Dis. Sci., Apr. 2007, 52:3465-72.
Takahashi et al., "Inhibitory Effects of Japanese Herbal Medicines Sho-saiko-to and Juzen-taiho-to on Nonalcoholic Steatohepatitis in Mice," PLoS One, Jan. 2014, 9(1):e87279.
Tanaka and Aoyama, "PPAR and NASH," Japanese Journal of Clinical Medicine, 2006, 64(6):1089-94, English abstract.
Tanaka et al., "Dysregulated expression of fatty acid oxidation enzymes and iron-regulatory genes in livers of Nrf2-null mice," J. Gastroenterol. Hepatol., 2012, 27:1711-7.
Tanaka et al., "Role of fibroblast growth factor 21 in the early stage of NASH induced by methionine- and choline-deficient diet," Biochimica et Biophysica Acta, 2015, 1852:1242-1252.
Tanaka, et al., "Role of PPARs in the pathophysiology of nonalcoholic fatty liver disease," Japanese Journal of Clinical Medicine, 2005, 63(4):700-706, English abstract.
Tang et al., "Curcumin Eliminates Leptin's Effects on Hepatic Stellate Cell Activation via Interrupting Leptin Signaling," Endocrinology, Jul. 2009, 150(7):3011-20.
Tarantino et al., "Pathogenesis of hepatic steatosis: the link between hypercortisolism and non-alcoholic fatty liver disease.", W. J. Gastroenterol., 19: 6735-6743, 2013.
Taygerly et al., "Discovery of INT131: A selective PPAR-gamma modulator that enhances insulin sensitivity", Bioorg Med Chem, 21(4), 979-992, 2013.
Teoh et al., "Short-Term Therapy with Peroxisome Proliferation-Activator Receptor-Agonist Wy-14,643 Protects Murine Fatty Liver Against Ischemia-Reperfusion Injury," Hepatology, Mar. 2010, 51(3):996-1006.
Teunissen et al., "Combination of CSF N-acetylaspartate and neurofilaments in multiple sclerosis", Neurology 72(15): 1322-1329, 2009.
Teunissen et al., "Neurofilaments as biomarkers in multiple sclerosis", Mult. Scler. 18(5): 552-556, 2012.
The United States Pharmacopeia, 23rd Ed. pp. 1843-1844, 1995.
Thorkildsen et al., "Glucagon-like peptide 1 receptor agonist ZP10A increases insulin mRNA expression and prevents diabetic progression in db/db mice.", J. Pharmacol Exp Ther., 307(2): 490-496, 2003.
Tilg and Moschen, "Evolving therapies for non-alcoholoic steatohepatitis," Expert Opin. Drug Discov., 2014, 9(6):687-696.
Tomita et al., "Free Cholesterol Accumulation in Hepatic Stellate Cells: Mechanism of Liver Fibrosis Aggravation in Nonalcoholic Steatohepatitis in Mice," Hepatology, 2014, 59(1):154-69.
Tomita et al., "Hepatic AdipoR2 Signaling Plays a Protective Role Against Progression of Nonalcoholic Steatohepatitis in Mice," Hepatology, Aug. 2008, 48(2):458-73.
Tong, "Acetyl-coenzyme A carboxylase: crucial metabolic enzyme and attractive target for drug discovery.", Cell. Malec. Life Sci., 62(16): 1784-1803, 2005.
Tourdias et al., "Neuroinflammatory imaging biomarkers: relevance to multiple sclerosis and its therapy", Neurotherapeutics, 10(1), 111-123, 2013.
Tsiodras and Mantzoros, "Leptin and Adiponectin in the HIV Associated Metabolic Syndrome:Physiologic and Therapeutic Implications," Am. J. Infectious Dis., 2006, 2(3):141-52.
Tsiodras, et al., "The HIV-1/HAART associated metabolic syndrome—Novel adipokines, molecular associations and therapeutic implications," Journal of Infection, 2010, 61:101-113.
Tsukamoto et al., "Fat paradox of steatohepatitis," J. Gastroenterol. Hepatol., 2008, 23(Suppl. 1):S104-7.
Turton et al., "A role for glucagon-like peptide-I in the central regulation of feeding." Nature, 379: 69-72, 1996.
Tushuizen et al.,"Incretin mimetics as a novel therapeutic option for hepatic steatosis". Liver Int., 26(8): 1015-1017, 2006.
Tworoger et al., "Plasma Adiponectin Concentrations and Risk of Incident Breast Cancer", J Clin Endocrinol Metab 92: 1510-1516, 2007.
Tworoger et al., "Relationship of Plasma Adiponectin With Sex Hormone and Insulin-like Growth Factor Levels", Obesity, 15: 2217-2224, 2007.
Tziomalos et al., "Nonalcoholic fatty liver disease and stains", Metabolism, 64: 1215-1223, 2015.
Uno et al., "Tranilast, an Antifibrogenic Agent, Ameliorates a Dietary Rat Model of Nonalcoholic Steatohepatitis", Hepatology 48: 109-118, 2008.
Uto, et al., "The peroxisome proliferator-activated receptor-gamma agonist, pioglitazone, inhibits fat accumulation and fibrosis in the livers of rats fed a choline-deficient, L-amino acid-defined diet," Hepatology Research, 2005, 32:235-242.

(56) References Cited

OTHER PUBLICATIONS

Vamvini et al., "Differential Effects of Oral and Intravenous Lipid Administration on Key Molecules Related to Energy Homeostasis", J. Clin Endocrinol Metab 101: 1989-1997, 2016.
Vamvini et al., "Irisin mRNA and circulating levels in relation to other myokines in healthy and morbidly obese humans", European Journal of Endocrinology 169 829-834, 2013.
Van Herek et al., "Animal Models of Nonalcoholic Fatty Liver Disease—A Starter's Guide", Nutrients., 9(10): 1072, 13 pages, 2017.
Van Raalte et al., "Peroxisome Proliferator-Activated Receptor (PPAR)-α: A Pharmacological Target with a Promising Future", D.H., PharmRes., 21(9): 1531-1538, 2004.
Vanni, et al., "From the metabolic syndrome to NAFLD or vice versa?" Digestive and Liver Disease, 2010, 42:320-330.
Varhaug et al., "Neurofilament light chain predicts disease activity in relapsing-remitting MS", Neurology—Neuroimmunology Neuroinflammation, vol. 5, No. 1, p. e422, 2017.
Velayudham et al., "VSL#3 Probiotic Treatment Attenuates Fibrosis Without Changes in Steatohepatitis in a Diet-Induced Nonalcoholic Steatohepatitis Model in Mice", Hepatology 49: 989-997, 2009.
Verdi et al., "Peroxisome Proliferator-Activated Receptor L162V Polymorphism in Nonalcoholic Steatohepatitis and Genotype 1 Hepatitis C Virus-Related Liver Steatosis", Journal of Investigative Medicine vol. 53 No. 7, 353-359, 2005.
Vernon et al., "Systematic review: the epidemiology and natural history of non-alcoholic fatty liver disease and non-alcoholic steatohepatitis in adults", Aliment Pharmacol Ther., 34:274-285, 2011.
Villegas et al., "Rosiglitazone, an agonist of peroxisome proliferator-activated receptor gamma, protects against gastric ischemia-reperfusion damage in rats: role of oxygen free radicals generation", European Journal of Phamacology, 505, 195-203, 2004.
Villhauer et al., "1-[[(3-Hydroxy-1-adamantyl)amino]acetyl]-2-cyano-(S)-pyrrolidine: A Potent, Selective, and Orally Bioavailable Dipeptidyl Peptidase IV Inhibitor with Antihyperglycemic Properties", J Med Chem 46: 2774-2789, 2003.
Villhauer et al., "1-[2-[(5-Cyanopyridin-2-yl)amino]ethylamino]acetyl-2-(S)-pyrrolidinecarbonitrile: A Potent, Selective, and Orally Bioavailable Dipeptidyl Peptidase IV Inhibitor with Antihyperglycemic Properties", J Med Chem 45: 2362-2365, 2002.
Von Tils et al., "Type II secretion in Yersinia—a secretion system for pathogenicity and environmental fitness", Front. Cell Infect. Microbial. 2(160): 1-11, 2012.
Wada et al., Eplerenone ameliorates the phenotypes of metabolic syndrome with NASH in liver-specific SREBP-lc Tg mice fed high-fat and high-fructose diet:, Am. J. Physiol. Endocrinol. J. Phy. 305: E1415-E1425, 2013.
Walker et al., "Subcutaneous Abdonninai Adipose Tissue Subcompartments: Potential Role in Rosiglitazone Effects", Obesity, vol. 16, pp. 1983-1991, 2008.
Walter, et al., "Adiponectin reduces connective tissue growth factor in human hepatocytes which is already induced in non-fibrotic non-alcoholic steatohepatitis," Experimental and Molecular Pathology, 2011, 91:740-744.
Wang et al. "Peroxisome proliferator-activated receptor gamma in malignant diseases" Critical 1-59 Reviews in Oncology/Hematology, vol. 58, p. 1-14, 2006.
Wang et al., "Stat3-Mediated Activation of MicroRNA-23a Suppresses Gluconeogenesis in Hepatocellular Carcinoma by Down-Regulating Glucose-6-Phosphatase and Peroxisome Proliferator-Activated Receptor gamma, Coactivator 1 Alpha", Hepatology 56: 186-197, 2012.
Wang et al., "Targeting CASP8 and FADD-like apoptosis regulator ameliorates nonalcoholic steatohepatitis in mice and nonhuman primates", Nat. Med, 23: 439-449, 2017.
Wang, et al., "Association between the Pro12Ala polymorphism of PPAR-gamma gene and the non-alcoholic fatty liver disease," Gene, 2013, 528:328-334.
Wang, et al., "Molecular regulation of miRNAs and potential biomarkers in the progression of hepatic steatosis to NASH," Biomark. Med., 2015, 9(11): 1189-1200.
Wang, et al., "Raspberry ketone protects rats fed high-fat diets against nonalcoholic steatohepatitis," J. Med. Food., 2012, 15(5):495-503.
Weber, "Dipeptidyl peptidase IV inhibitors for the treatment of diabetes.", J. Med. Chem., 47:4135-4141, 2004.
Wedick et al., "Effects of caffeinated and decaffeinated coffee on biological risk factors for type 2 diabetes: a randomized controlled trial", Nutrition Journal, 10: 93, 9 pages, 2011.
Wei et al., "Low Plasma Adiponectin Levels and Risk of Colorectal Cancer in Men: A Prospective Study", J Natl Cancer Inst. 97: 1688-1694, 2005.
Werner, "Preclinical pharmacology of the new GLP-1 receptor agonist AVE0010.", Ann Endocrinol (Paris), 69(2): 164-5, 2008.
Williams et al., "Adiponectin receptor expression is elevated in colorectal carcinomas but not in gastrointestinal stromal tumors", Endocrine-Related Cancer, 15 289-299, 2008.
Williams et al., "Coffee Consumption is Associated With Higher Plasma Adiponectin Concentrations in Women With or Without Type 2 Diabetes", Diabetes Care 31:504-507, 2008.
Williams et al., "Sleep Duration and Snoring in Relation to Biomarkers of Cardiovascular Disease Risk Among Women With Type 2 Diabetes", Diabetes Care 30: 1233-1240, 2007.
Wilson et al., "The Simoa HD-1 Analyzer: A Novel Fully Automated Digital Immunoassay Analyzer with Single-Molecule Sensitivity and Multiplexing,", J Lab Autom 21(4): 533-547, 2015.
Wolfe et al., "Effect of dieting on plasma leptin, soluble leptin receptor, adiponectin and resistin levels in healthy volunteers", Clinical Endocrinology 61, 332-338, 2004.
Wright, "Renal Na+-glucose cotransporters", Am J Physiol Renal Physiol 280: F10, 9 pages, 2001.
Wu et al., "Dietary fucoxanthin increases metabolic rate and upregulated mRNA expressions of the PGC-lalpha network, mitochondrial biogenesis and fusion genes in white adipose tissues of mice.", Afarine Drugs, 12(2): 964-982, 2014.
Wu et al., "PPARg is essential for protection against nonalcoholic steatohepatitis", Gene Therapy, 17, 790-798, 2010.
Xia et al., "Characterization of long noncoding RNA transcriptome in highenergy diet induced nonalcoholic steatohepatitis minipigs", Scientific Reports 6: 30709, 11 pages, 2016.
Xia et al., "Transcriptome Analysis on the Inflammatory Cell Infiltration of Nonalcoholic Steatohepatitis in Bama Minipigs Induced by a Long-Term High- Fat, High-Sucrose Diet", PLoS ONE 9(11): e113724, 2014.
Yakaryilmaz et al., "Effects of vitamin E treatment on peroxisome proliferatoractivated receptor-a expression and insulin resistance in patients with non-alcoholic steatohepatitis: results of a pilot study", Internal Medicine Journal 37, 229-235, 2007.
Yamada et al., "Characteristics of hepatic fatty acid compositions in patients with nonalcoholic steatohepatitis", Liver International ISSN 1478-3223, 2014.
Yamada et al., "Suppressive Role of PPARγ-Regulated Endothelial Nitric Oxide Synthase in Adipocyte Lipolysis", PLoS ONE 10(8): e0136597, 15 pages, 2015.
Yamaguchi et al., "Blockade of interleukin-6 signaling enhances hepatic steatosis but improves liver injury in methionine choline-deficient diet-fed mice", Laboratory Investigation, 90, 1169-1178, 2010.
Yang et al., "Regulation of Immune Responses and Autoimmune Encephalomyelitis by PPARs", PPAR Research, vol. 2010, Article ID 104705, 11 pages, 2010.
Yang et al., "Role of PPARgamma in renoprotection in Type 2 diabetes: molecular mechanisms and therapeutic potential", Clinical Science, 116, 17-26 2009.
Yang et al., "The emerging role of adiponectin in cerebrovascular and neurodegenerative diseases", Biochimica et Biophysica Acta, vol. 1852, No. 9, pp. 1887-1894, 2015.
Yannakoulia et al., "Body Fat Mass and Macronutrient Intake in Relation to Circulating Soluble Leptin Receptor, Free Leptin Index, Adiponectin, and Resistin Concentrations in Healthy Humans", Clin Endocrinol Metab 88: 1730-1736, 2003.

(56) References Cited

OTHER PUBLICATIONS

Yannakoulia et al., "Dietary factors associated with plasma high molecular weight and total adiponectin levels in apparently healthy women", European Journal of Endocrinology 159, R5-R10, 2008.
Yannakoulia, et al., "A dietary pattern characterized by high consumption of whole-grain cereals and low-fat dairy products an dlow consumption of refined cereals is positively associated with plasma adiponectin levels in healthy women," Metabolism Clinical and Experimental, 2008, 57:824-830.
Yates et al., "Neurofilament subunit (NFL) head domain phosphorylation regulates axonal transport of neurofilaments", Eur. J Cell Biol. 88: 193-202, 2009.
Yew et al., "Selective peroxisome proliferator-activated receptor-gamma modulation to reduce cardiovascular risk in patients with insulin resistance", Recent Pat on Cardiovasc Drag Discove, 7(1), 33-41, 2012.
Yki-Jarvinen et al., "The fatty liver and insulin resistance", Current Molecular Medicine (Hilversum), vol. 5, No. 3, pp. 287-295, 2005.
Yoneda et al., "Life Style-Related Diseases of the Digestive System: Gene Expression in Nonalcoholic Steatohepatitis Patients and Treatment Strategies", J Pharmacol Sci 105, 151-156, 2007.
Yoneda et al., "PPAR gamma ligand pioglitazone as a therapeutic strategy in nonalcoholic steatohepatitis (NASH)", Folia Pharmacol. Jpn., 128, 235-238, 2006.
Yuan et al., "Cardioprotective effects of peroxisome proliferator activated receptor gamma activators on actue myocarditis: anti-inflammatory actions associated with nuclear factor kappaB blockade", Heat, 91: 1203-1208, 2005.
Zambon et al., "The role of fenofibrate in clinical practice", Diabetes Vase Dis Res., 4(suppl 3): S15-S20, 2007.
Zhang et al., "Peroxisome proliferator-activaled receptor (PPAR) alpha and -gamma regulate IFNgamma and IL-17A production by human T cells in a sex-specific way", PNAS, vol. 109, No. 24, 9505-9510, 2012.
Zhang et al., "Selective Modulators of PPARy Activity: Molecular Aspects Related to Obesity and Side-Effects." PPAR Research vol. 2007, 7 pages, 2007.
Zhang, et al., "Association between resistin + 299A/A genotype and nonalcoholic fatty liver disease in Chinese patients with type 2 diabetes mellitus," Gene, 2013, 529:340-344.
Zhang, et al., "PPARalpha/gamma and antagonists differently affect hepatic lipid metabolism, oxidative stress and inflammatory cytokine production in steatohepatitic rats," Cytokine, 2015, 75:127-135.
Zhao et al., "An experimental study on the reverse mechanism of PPAR-Y agonist rosiglitazone in rats with non-alcoholic steatohepatitis", Chin. J. Hapatol., vol. 15, No. 6, 450-455, 2007.
Zhao et al., "Pioglitazone ameliorates nonalcoholic steatohepatitis by down-regulating hepatic nuclear factor-kappa B and cyclooxygenases-2 expression in rats", Chin Med J., 125(13): 2316-2321, 2012.
Zheng et al., "Fish consumption and CHD mortality: an updated meta-analysis of seventeen cohort studies", Public Health Nutr., 15(4): 725-737, 2012.
Zheng, et al., "Exposure to ambient particulate matter induces a NASH-like phenotype and impairs hepatic glucose metabolism in an animal model," Journal of Hepatology, 2013, 58:148-154.
Zhu et al., "Delayed Maturation of Regenerating Myelinated Axons in Mice Lacking Neurofilaments", Exp. Neural. 148: 299-316, 1997.

Ziamajidi, et al., "Amelioration by chicory seed extract of diabetes- and oleic acid-induced non-alcoholic fatty liver disease (NAFLD)/non-alcoholic steatohepatitis (NASH) via modulation of PPARalpha and SREBP-1," Food and Chemical Toxicology, 2013, 58:198-209.
Ziemke et al., "Adiponectin in insulin resistance: lessons from translational research", Am J Clin Nutr 91(suppl): 258S-61S, 2010.
Zou, et al., "High-fat emulsion-induced rat model of nonalcoholic steatohepatitis," Life Sciences, 2006, 79:1100-1107.
International Preliminary Report on Patentability in International Appln. No. PCT/US2019/068688, dated Oct. 14, 2021, 9 pages.
International Preliminary Report on Patentability in International Appln. No. PCT/US2019/068693, dated Oct. 14, 2021, 10 pages.
International Preliminary Report on Patentability in International Appln. No. PCT/US2019/068698, dated Oct. 14, 2021, 12 pages.
International Preliminary Report on Patentability in International Appln. No. PCT/US2019/068704, dated Oct. 14, 2021, 13 pages.
International Preliminary Report on Patentability in International Appln. No. PCT/US2019/068706, dated Oct. 14, 2021, 11 pages.
Sahebkar et al., "Role of selective peroxisome proliferator-activated receptor modulators in managing cardiometabolic disease: tale of a roller-coaster" Diabetes, Obesity and Metabolism, 16(9):780-792, Sep. 2014.
Anonymous, "Assessment report for Komboglyze" Jun. 1, 2011, retrieved on Jan. 5, 2022, retrieved from URL<https:/www.ema.europa.eu/en/documents/assessment-report/komboglyze-epar-public-assessment-report_en.pdf>, 77 pages.
Badr, "PPAR research: Successful launching and promising future" PPAR research. 2009(543584): 3 pages, Jul. 30, 2009.
Dufour et al., "Combination therapy for non-alcoholic steatohepatitis: rationale, opportunities and challenges" Gut, 69(10):1877-1884, Oct. 1, 2020.
Fakhredin et al.. "Imaging in multiple sclerosis: a new spin on lesions" Journal of medical imaging and radiation oncology, 60(5):577-586, Oct. 2016.
Perakakis et al., "The Selective Peroxisome Proliferator-Activated Receptor Gamma Modulator CHS-131 Improves Liver Histopathology and Metabolism in a Mouse Model of Obesity and Nonalcoholic Steatohepatitis" Hepatology communication. 4(9):1302-1315, Sep. 2020.
Pourkavoos, "Unique risks, benefits, and challenges of developing drug-drug combination products in a pharmaceutical industrial setting" Combination Products in Therapy, 2(1): 31 pages, Jan. 1, 2012.
Sanyal et al., "A pilot study of vitamin E versus vitamin E and pioglitazone for the treatment of nonalcoholic steatohepatitis" Clinical Gastroenterology and Hepatology, 2(12):1107-1115, Dec. 1, 2004.
Shimada et al, "Ppary Agonists for the Disease of Gastrointestinal Tract and Liver", Dokkyo Medical University, 2010, 68:312-316 (with English abstract).
Tahara et al., "SGLT2 inhibitor ipragliflozin alone and combined with pioglitazone prevents progression of nonalcoholic steatohepatitis in a type 2 diabetes rodent model" Physiological reports, 7(22):e14286, 16 pages, Nov. 7, 2019.
Younossi, "Emerging research on MGL-3196 for the treatment of nonalcoholic steatohepatitis" Gastroenterology & hepatology, 15(6):317-319, Jun. 2019.

* cited by examiner

METHODS FOR THE TREATMENT OF NONALCOHOLIC FATTY LIVER DISEASE AND/OR LIPODYSTROPHY

CROSS-REFERENCE TO RELATED APPLICATIONS

This application is a continuation of U.S. patent application Ser. No. 16/744,433, filed on Jan. 16, 2020, now U.S. Pat. No. 10,772,865, which is a continuation of U.S. patent application Ser. No. 15/062,331, filed on Mar. 7, 2016, now U.S. Pat. No. 10,555,929, which claims priority to U.S. Provisional Application No. 62/130,488, filed Mar. 9, 2015, each of which are herein incorporated by reference in their entireties.

BACKGROUND OF THE INVENTION

A healthy liver contains a minimal amount of fat. When a significant number (usually more than 5%) of the cells in the liver have abnormal fat accumulation the liver is considered diseased. Fatty liver diseases consist of two main categories based on whether they are caused by excessive alcohol consumption or not. Fatty liver diseases that are not caused by excessive alcohol consumption are termed nonalcoholic fatty liver diseases ("NAFLDs"), which consist of simple nonalcoholic fatty liver ("NAFL") and in a significant portion of subjects proceeds to a more severe form associated with inflammation, called nonalcoholic steatohepatitis ("NASH"). NAFL and/or NASH may also include scarring of the liver known as liver fibrosis or in a more severe form, liver cirrhosis. Scarring of the liver reduces liver function up to and including liver failure.

NAFLDs have many non-mutually exclusive causes including malnutrition, overeating, obesity, diabetes, medications and hyperlipidemia. However, the main cause of NAFLDs appears to be high-fat, high-calorie diets leading to an excess amount of energy which exceeds the storage capacity of adipose tissue and thus is stored in the liver. NASH is positively correlated with the metabolic syndrome (i.e. diseases related to diabetes mellitus type 2, such as insulin resistance, trunk obesity, hyperlipidemia and hypertension) although the correlation is not 100%.

Over the past 20 years, the number of cases of NAFLDs has nearly doubled. Almost 30% of people in developed countries are estimated to have NAFL or NASH including 20% of adults in the United States. The best method of prevention and treatment of NAFLDs include a low-calorie diet and exercise. However, due to voluntary non-compliance, an inability to exercise and/or long term diet restriction, many patients must also be treated with pharmaceuticals.

Current pharmaceutical treatments that have been proposed or tested in prior trials, although not yet approved for NAFLDs include vitamin C, vitamin E, betaine, metformin, orlistat, selenium, thiazolidinediones ("TZDs"), urodeoxycholic acid, and pentoxifilline. Ongoing FDA-approved trials include: GR-MD-02, a galactose-containing polysaccharide manufactured by Galectin Therapeutics Inc., for the treatment of NASH with attendant liver fibrosis; a Hadassah, LTD drug technology, which includes feeding patients with natural antibodies to intestinal flora associated with NAFLDs; and obeticholic acid for treatment of NASH with attendant liver fibrosis being conducted by Intercept Pharmaceuticals, Inc.

A diverse array of other agents have been proposed as either direct or indirect treatments for NAFLDs (e.g.: interleukin-22 (U.S. Patent Application Publication No. 20140377222); piperine derivatives (U.S. Patent Application Publication No. 20140371271); nuclear transport modifiers (U.S. Patent Application Publication No. 20140336113) and *Bifidobacterium pseudocatenulatum* strain CECT 7765 (U.S. Patent Application Publication No. 20140369965).

Lipodystrophic syndromes present with either a complete or partial lack of adipose tissue. Although less prevalent than NAFLDs, lipodystrophic syndromes have a more severe presentation. Patients with generalized lipodystrophy (i.e. congenital and/or acquired) have metabolic abnormalities consistent with the metabolic syndrome and hepatomegaly due to fatty infiltration of the liver. Patients with congenital partial lipodystrophy also present with metabolic complications including insulin resistance, usually accompanied by hypertriglyceridemia, hyperlipidemia and possibly hyperglycemia.

The treatment plan for lipodystrophic syndrome is similar to that for NAFLDs including diet, exercise and treatment of underlying metabolic disturbances. Many of the same drugs used to treat NAFLDs have been implemented to treat lipodystrophic syndromes. A recently approved medication for treating congenital complete generalized lipodystrophy associated with metabolic dysfunction is leptin.

Despite the attention that NAFLDs and lipodystrophic syndromes have recently received there is still no effective pharmaceutical options for their treatment. The lack of an effective treatment combined with the rapid rise in prevalence of the diseases creates an immediate need in the art for new drugs and methods of treatment for NAFLDs and/or lipodystrophic syndromes.

BRIEF SUMMARY OF THE INVENTION

The present invention provides a method of treating a disease associated with insulin resistance selected from a nonalcoholic fatty liver disease ("NAFLD"), a lipodystrophic syndrome or a combination thereof comprising administering to a subject in need thereof a therapeutically effective amount of a compound of formula (I):

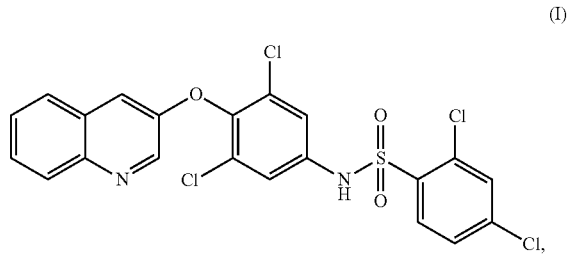 [SMILES: O=S(=O)(Nc1cc(Cl)c(Oc2cnc3ccccc3c2)c(Cl)c1)c1ccc(Cl)cc1Cl]

or a pharmaceutically acceptable salt, ester or prodrug thereof.

The compound of formula (I) is also known as 2,4-Dichloro-N-[3,5-dichloro-4-(3-quinolinyloxy)phenyl]benzenesulfonamide (ACD/IUPAC name) and is referred to as INT131 throughout the specification.

In another embodiment, the present invention provides a method of treating a disease associated with insulin resistance selected from an NAFLD, a lipodystrophic syndrome or a combination thereof comprising administering to a subject in need thereof a therapeutically effective amount of a compound of formula (I) and an effective amount of vitamin E.

In a preferred embodiment, the present invention provides a method of treating a disease associated with insulin resistance selected from an NAFLD, a lipodystrophic syndrome or a combination thereof comprising administering to a subject in need thereof a therapeutically effective amount of a compound of formula (I) and an effective amount of vitamin E concomitantly, simultaneously or consecutively.

In another preferred embodiment, the present invention provides a method of treating a disease associated with insulin resistance selected from an NAFLD, a lipodystrophic syndrome or a combination thereof comprising administering to a subject in need thereof a compound of formula (I) at amount of from about 0.1 to about 10.0 milligrams ("mg") per day, preferably from about 1 to about 2 mg per day, more preferably about 1 or about 2 mg per day and vitamin E at an amount from about 1 to about 10,000 international units ("IU") per day, preferably from about 400 to about 1,000 IU per day, and more preferably at about 400, 800 or 1,000 IU per day.

The present invention provides a method of treating an NAFLD comprising administering to a subject in need thereof a therapeutically effective amount of a compound of formula (I):

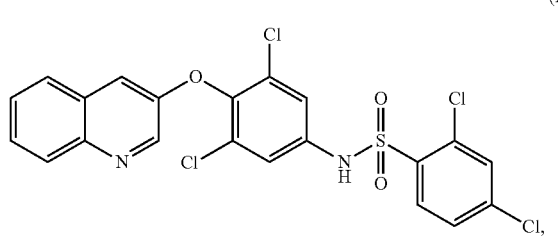

or a pharmaceutically acceptable salt, ester or prodrug thereof.

In a preferred embodiment the present invention provides a method of treating nonalcoholic fatty liver (NAFL) comprising administering to a subject in need thereof a therapeutically effective amount of INT131 or a pharmaceutically acceptable salt, ester or prodrug thereof.

In another preferred embodiment the present invention provides a method of treating NAFL with attendant liver fibrosis comprising administering to a subject in need thereof a therapeutically effective amount of INT131 or a pharmaceutically acceptable salt, ester or prodrug thereof.

In another preferred embodiment the present invention provides a method of treating NAFL with attendant liver cirrhosis comprising administering to a subject in need thereof a therapeutically effective amount of INT131 or a pharmaceutically acceptable salt, ester or prodrug thereof.

In another preferred embodiment the present invention provides a method of treating nonalcoholic steatohepatitis (NASH) comprising administering to a subject in need thereof a therapeutically effective amount of INT131 or a pharmaceutically acceptable salt, ester or prodrug thereof.

In another preferred embodiment the present invention provides a method of treating NASH with attendant liver fibrosis comprising administering to a subject in need thereof a therapeutically effective amount of INT131 or a pharmaceutically acceptable salt, ester or prodrug thereof.

In another preferred embodiment the present invention provides a method of treating NASH with attendant liver cirrhosis comprising administering to a subject in need thereof a therapeutically effective amount of INT131 or a pharmaceutically acceptable salt, ester or prodrug thereof.

In another preferred embodiment the present invention provides a method of treating an NAFLD comprising administering to a subject in need thereof from about 0.1 to about 10.0 mg per day of INT131 or a pharmaceutically acceptable salt, ester or prodrug thereof, preferably from about 1 to about 5 mg per day, more preferably about 1 or about 2 mg per day.

In another preferred embodiment the present invention provides a method of treating an NAFLD comprising administering to a subject in need thereof a therapeutically effective amount of INT131 or a pharmaceutically acceptable salt, ester or prodrug thereof wherein the method provides an NAFLD activity score ("NAS") of 7 or less, preferably 5 or less and more preferably 3 or less.

In another embodiment the present invention provides a pharmaceutical composition for the treatment of a disease associated with insulin resistance selected from an NAFLD, a lipodystrophic syndrome or a combination thereof comprising INT131.

In another preferred embodiment the present invention provides a pharmaceutical composition for the treatment of an NAFLD comprising INT131.

In another preferred embodiment the present invention provides a pharmaceutical composition for the treatment of a lipodystrophic syndrome comprising INT131.

In another preferred embodiment the present invention provides a method of treating a lipodystrophic syndrome comprising administering to a subject in need thereof a therapeutically effective amount of INT131 or a pharmaceutically acceptable salt, ester or prodrug thereof.

In a preferred embodiment the present invention provides a method of treating a generalized lipodystrophy comprising administering to a subject in need thereof a therapeutically effective amount of INT131 or a pharmaceutically acceptable salt, ester or prodrug thereof.

In another preferred embodiment the present invention provides a method of treating a congenital generalized lipodystrophy comprising administering to a subject in need thereof a therapeutically effective amount of INT131 or a pharmaceutically acceptable salt, ester or prodrug thereof.

In another preferred embodiment the present invention provides a method of treating an acquired generalized lipodystrophy comprising administering to a subject in need thereof a therapeutically effective amount of INT131 or a pharmaceutically acceptable salt, ester or prodrug thereof.

In another preferred embodiment the present invention provides a method of treating a partial lipodystrophy comprising administering to a subject in need thereof a therapeutically effective amount of INT131 or a pharmaceutically acceptable salt, ester or prodrug thereof.

In another preferred embodiment the present invention provides a method of treating a congenital partial lipodystrophy comprising administering to a subject in need thereof a therapeutically effective amount of INT131 or a pharmaceutically acceptable salt, ester or prodrug thereof.

In another preferred embodiment the present invention provides a method of treating an acquired partial lipodystrophy comprising administering to a subject in need thereof a therapeutically effective amount of INT131 or a pharmaceutically acceptable salt, ester or prodrug thereof.

In another embodiment the present invention provides a method of treating hyperlipidemia comprising administering to a subject suffering from a lipodystrophic syndrome and hyperlipidemia a therapeutically effective amount of INT131 or a pharmaceutically acceptable salt, ester or prodrug thereof.

In another embodiment the present invention provides a method of treating hyperlipidemia comprising administering to a subject suffering from a lipodystrophic syndrome, an NAFLD and hyperlipidemia a therapeutically effective amount of INT131 or a pharmaceutically acceptable salt, ester or prodrug thereof.

In another preferred embodiment the present invention provides a method of treating hyperglycemia comprising administering to a subject suffering from lipodystrophic syndrome and hyperglycemia a therapeutically effective amount of INT131 or a pharmaceutically acceptable salt, ester or prodrug thereof.

In another preferred embodiment the present invention provides a method of treating hyperglycemia comprising administering to a subject suffering from a lipodystrophic syndrome, an NAFLD and hyperglycemia a therapeutically effective amount of INT131 or a pharmaceutically acceptable salt, ester or prodrug thereof.

DETAILED DESCRIPTION OF THE INVENTION

INT131 is compound distinct from thiazolidinediones that activates a specific subset of PPARγ-dependent pathways. Specifically, INT131 was designed to activate anti-inflammatory, anti-oxidative stress, and neuroprotective pathways without activating edemagenic and lipogenic inducing pathways, which are activated by thiazolidinedione (TZD) drugs.

The free base and certain pharmaceutically acceptable salts of INT131 are described in International Patent Publication No. WO/2001/000579, and U.S. Pat. Nos. 6,583,157 B2 and 7,041,691 B1. U.S. Pat. No. 7,223,761 B2 discloses that the benzenesulfonic acid (besylate) salt of INT131, and polymorphs thereof.

Definitions

As used herein the term "nonalcoholic fatty liver disease" or "NAFLD" refers to all diseases of the liver caused by steatosis that are not a result of the excessive consumption of alcohol. NAFLDs include, but are not limited to, simple nonalcoholic fatty liver ("NAFL"), nonalcoholic steatohepatitis ("NASH"), NAFL with attendant liver fibrosis, NAFL with attendant liver cirrhosis, NASH with attendant liver fibrosis, NASH with attendant liver cirrhosis, and fatty liver disease resulting from hepatitis, obesity, diabetes, insulin resistance, hypertriglyceridemia, abetalipoproteinemia, glycogen storage diseases, Weber-Christian disease, Wolman disease, pregnancy or lipodystrophy.

As used herein the term "simple nonalcoholic fatty liver disease" or "NAFL" refers to a liver that has greater than 5% by weight fat content.

As used herein the term "lipodystrophic syndrome" or "lipodystrophic syndromes" or "lipodystrophy" refers to a disorder characterized by either complete or partial lack of adipose tissue in a subject affected by the disorder. Partial lack of adipose tissue can be localized to a particular anatomical region of the body of the subject and may include a gain of adipose tissue in a separate anatomical region. Lipodystrophy may also present with hyperlipidemia and/or hyperglycemia.

As used herein the term "hyperlipidemia" refers to lipid or triglyceride content of the blood exceeding normal values well known in the art.

As used herein the term "hyperglycemia" refers to glucose content of the blood exceeding normal values well known in the art.

As used herein the term "generalized lipodystrophy" refers to a disorder characterized by a complete lack of adipose tissue. Generalized lipodystrophy may be either congenital or acquired.

As used herein the term "congenital generalized lipodystrophy" or "CGL" refers to a disorder characterized by a complete lack of adipose tissue as a result of a congenital defect. Congenital generalized lipodystrophy, although not limited to the following types, may occur as a result of Seip-Berardinelli syndrome, a mutation to the AGPAT2 gene (i.e. Type 1 CGL), a mutation to the BSCL2 gene (i.e. Type 2 CGL), a mutation to the CAV1 gene (i.e. Type 3 CGL) or a mutation to the PTRF gene (i.e. Type 4 CGL).

As used herein the term "acquired generalized lipodystrophy" refers to a disorder characterized by a complete lack of adipose tissue as a result of the subject's post-birth environment.

As used herein the term "congenital partial lipodystrophy" refers to a disorder characterized by a partial lack of adipose tissue as a result of a congenital defect. Congenital partial lipodystrophy, although not limited to the following types, may occur as a result of Kobberling's syndrome (i.e. familial partial lipodystrophy ("FPLD") type 1), Dunnigan's syndrome (i.e. FPLD type 2), a mutation to the PPARγ gene (i.e. FPLD type 3), a mutation to the AKT2 gene (FPLD type 4), a mutation to the PLIN1 gene (i.e. FPLD type 5), a mutation to the CAV1 gene, or mandibuloacral dysplasia.

As used herein the term "acquired partial lipodystrophy" refers to a disorder characterized by a partial lack of adipose tissue as a result of the subject's post-birth environment.

As used herein the term "subject" refers to animals such as mammals, including but not limited to, primates (e.g., humans), cows, sheep, goats, horses, dogs, cats, rabbits, rats, mice and the like. In preferred embodiments, the subject is a human.

As used herein the term "therapeutically effective amount" refers to that amount of the compound being administered sufficient to prevent development of or alleviate to some extent one or more of the symptoms or the signs of the condition or disorder being treated.

The terms "treat", "treating" and "treatment" refer to a method of alleviating or abrogating a disease and/or its attendant symptoms or signs.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either net or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either net or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isbutyric, oxalic, maleic, malonic, benzoic, succinic, suberic, fumeric mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", *Journal of Pharmaceutical Science*, 1977, 66, 1-19). Certain specific compounds of the present inventions contain both basic and acidic functionalities that allow the compounds to be converted into either base or acid addition salts.

The neutral forms of the compounds may be registered by contacting the salt with abase or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In additional to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may be bioavailable by oral administration whereas the parent drug is not. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity. Additional examples include peptidyl derivatives of a compound of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium (3H), iodine-125 ($^{125}$I) or carbon-14 ($^{14}$C). All isotopic variations of the compounds of the present invention, whether radioactive or not, are intended to be encompassed within the scope of the present invention.

As used herein the term "composition" is intended to encompass a product comprising the specified ingredients in the specified amounts, as well as any product which results, directly or indirectly, from a combination of the specified ingredients in the specified amounts.

Embodiments of the Invention

New uses of the known compound INT131 have now been discovered. Specifically, INT131 has now been discovered to treat disorders associated with insulin resistance selected from an NAFLD, a lipodystrophic syndrome or a combination thereof. As seen below, treatment with INT131 of trial subjects suffering from an NAFLD results in a reduction in the subject's NAS.

In particular, the compound of formula (I),

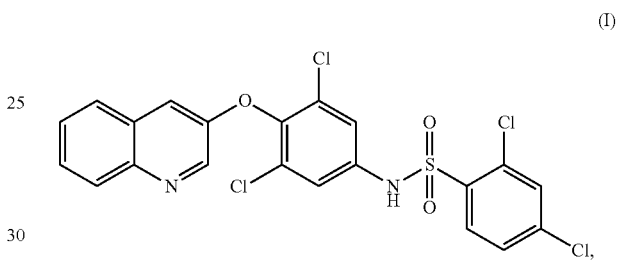

has been found to be unexpectedly effective for NAFLDs.

This compound is also known as INT131.

Compositions of the Invention

The present invention also provides pharmaceutical compositions that comprise compounds of the present invention formulated together with one or more pharmaceutically acceptable carriers. The pharmaceutical compositions can be specially formulated for oral administration in solid or liquid form, for parenteral administration or for rectal administration.

The pharmaceutical compositions of this invention can be administered to humans and other mammals orally, rectally, parenterally, intracisternally, intravaginally, transdermally (e.g. using a patch), transmucosally, sublingually, pulmonary, intraperitoneally, topically (as by powders, ointments or drops), bucally or as an oral or nasal spray. The terms "parental" or "parenterally," as used herein, refers to modes of administration which include intravenous, intramuscular, intraperitoneal, intrasternal, subcutaneous and intraarticular injection and infusion.

In another aspect, the present invention provides a pharmaceutical composition comprising a component of the present invention and a physiologically tolerable diluent. The present invention includes one or more compounds as described above formulated into compositions together with one or more physiologically tolerable or acceptable diluents, carriers, adjuvants or vehicles that are collectively referred to herein as diluents, for parenteral injection, for intranasal delivery, for oral administration in solid or liquid form, for rectal or topical administration, among others.

Compositions suitable for parenteral injection may comprise physiologically acceptable, sterile aqueous or non-aqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), vegetable oils (such as olive oil), injectable organic esters such as ethyl oleate, and suitable mixtures thereof.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol, glycerol monostearate, and PEG caprylic/capric glycerides; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Example

Protocol

A 48 week double blind, placebo controlled, randomized, parallel group study will be conducted to evaluate the effect of INT131 on hepatic histology of obese patients with NASH. Specifically, at least 225 subjects are chosen that fit the following criteria: (1) age 18 to 75 years old; (2) body mass index (BMI) greater than 25 kg/m$^2$ and less than 40 kg/m$^2$; (3) NAFLD fibrosis score greater than or equal to 1.0 and less than 4.0; (4) average daily alcohol consumption of 10 g/day or less; (5) NAFLD activity score ("NAS") of 3 or greater; (6) histologically proven steatohepatitis on a diagnostic liver biopsy performed within 6 months of randomization, confirmed central laboratory reading of slides (steatosis >5% lobular inflammation, any amount of ballooning); (7) women who meet the following criteria: women of childbearing potential with a negative urine pregnancy test at Screening who agree to use 1 or more approved methods of birth control during the study. Approved methods of birth control are: hormonal contraception, intrauterine device, diaphragm plus spermicide, female condom plus spermicide. Abstinence from heterosexual intercourse will be acceptable only if it is the preferred and usual lifestyle of the subject regardless of study participation; abstinence should be practiced for the duration of the study and until 8 weeks after taking the last dose of study drug; or women who have been postmenopausal for at least 2 years (with amenorrhea for at least 1 year) or have had a hysterectomy, bilateral salpingo-oophorectomy, or tubal ligation prior to signing the informed consent form; (8) no participation in a previous study of NASH; (9) no participation in a study with an investigational drug or device study within the 28 days prior to randomization (Week 0/Day 0) or a period equal to 5 times the half-life of the investigational agent (whichever is longer); (10) no use of the following medication within the last 6 months or during the trial (anti-depressant, antipsychotics or other dopamine antagonists, dietary supplements including tryptophan or vitamin E, estrogens, progestins, glucocorticosteroids, insulin, thiazolidinediones, dipeptidy peptidase (DPP) IV inhibitors and other GLP-1-based therapies, orlistat, phentermine, topiramate, lorcaserin, buproprion or other weight reducing medication, metreleptin, vitamin E, multivitamins, ferrum, ursodeoxycholic acid, interferon, tamoxifene, methotrexate, amiodarone, biologic agents, any medication affecting hemostasis, such as antiplatelet agents, aspirin or oral anticoagulants); (10) No alanine amino transferase (ALT) and aspartate amino transferase (AST) of 5× the upper limit of normal ("ULN"); (11) no unexplained serum creatinine phosphokinase (CPK) >3×ULN; (12) no known alcohol and/or any other drug abuse or dependence within the last 5 years; (13) no average daily alcohol consumption of >20 g/day (0.7 ounces); (14) no regular consumption >3 caffeinated beverages per day (ie, coffee, sodas, not chocolate and caffeinated tea; (15) no type 1 diabetes mellitus (16) no uncontrolled glycemia (Glycosolated Hemoglobin A1C≥9%) and/or HbA1C increment >1% within 6 months prior to enrollment or OR type 2 diabetes with recurrent major hypoglycemic or hypoglycemic unawareness, (17) no known history or the presence of clinically significant cardiovascular disease, New York Heart Association (NYHA) Class III or IV congestive heart failure; (18) no known history or the presence of clinically significant gastrointestinal, metabolic disorder other than diabetes mellitus, neurologic, pulmonary, endocrine, psychiatric, neoplastic disorder, or nephrotic syndrome; (19) No history of bariatric surgery; (20) no presence or history of malignancy, except for successfully treated non metastatic basal or squamous cell carcinoma of the skin and carcinoma in situ of the cervix; (20) no major systemic infections, including human immunodeficiency virus (HIV): (21) no unresolved Hepatitis B or C infection (defined as positive hepatitis B surface antibody [HBsAb], hepatitis B core antibody [HBcAb], or hepatitis C virus [HCV] RNA); (22) no history of any disease or condition known to interfere with absorption, distribution, metabolism or excretion of drugs including bile salt metabolism, (i.e., inflammatory bowel disease), previous intestinal surgery; chronic pancreatitis, celiac disease or previous vagotomy; (23) no weight loss >5% in the 6 months prior to randomization; (24) no uncontrolled hypertension (systolic blood pressure >160 mmHg and diastolic blood pressure >100 mmHg) (Mancia 2013)≤3 months prior to Screening; (25) no breastfeeding and pregnant mothers, and/or women who plan to get pregnant during the course of the study; (26) no medical history or multiple drug allergies (anaphylactoid drug reaction in >2 drug groups); (27) no uncontrolled hyperthyroidism or hypothyroidism; (28) no use of the following medications ≤12 months prior to screening: antidepressant, antipsychotics or other dopamine antagonists, dietary supplements including tryptophan, estrogens, progestins, glucocorticosteroids, insulin, thiazolidinediones, dipepetidy peptidase (DPP) IV inhibitors and other glucagon-like (GLP-1) based therapies and/or Pioglitazone, sibutramine, orlistat, rimonabant, phentermine, topirarmate, vitamin E, multivitamins, ferrum, ursodeoxycholic acid, interferon, tamoxifen, methotrexate, amiodarone, biologic agents, an medication affecting homostasis, such as antiplatelet agents aspirin or oral anti-coagulants; (Homeopathic and/or alternative treatments; (29) no use of vitamin E, fish oil, or urosodeoxycholic acid <3 months prior to diagnostic liver biopsy; (30) no renal dysfunction estimated glomerular filtration rate (eGFR) <40; (31) no presence of any other condition or illness that in the opinion of the Investigator would put the subject at increased risk or affect the ability to participate in the study; (32) not unable or unwilling to sign informed consent; and (33) no instance of liver cirrhosis (in the alternative, a trial may be developed wherein the subjects may have instances of liver cirrhosis) or clinical evidence of decompensated chronic liver disease: radiological or clinical evidence of ascites, current or previous hepatic encephalopathy and evidence of portal hypertension or varices on endoscopy; other liver disease (viral hepatitis, autoimmune hepatitis, primary sclerosing cholangitis, primary biliary cirrhosis and overlap syndromes, drug-induced liver disease, hemochromatosis, Wilson's disease, α1-antitrypsin deficiency); type 1 diabetes mellitus; type 2 diabetes with recurrent uncontrolled hyperglycemia or major hypoglycaemia or hypoglycaemic unawareness; valvular heart disease; depression or thoughts of suicide; severe anemia or leucopenia; pancreatitis; uncontrolled hypothyroidism or hyperthyroidism or other endocrinopathy such as adrenal insufficiency; renal failure; thrombotic disorders; any malignancy; breastfeeding, pregnancy or plan for pregnancy; addiction to any drug; medical history of multiple drug allergies (defined as anaphylactoid drug reactions) or allergy to INT 131. In another example of this trial subjects would be allowed to be on stable doses of antidiabetic medications such as metformin for the duration of the study.

The at least 225 subjects are randomly and evenly assigned to 3 groups of equal number of subjects. The first group receives 1.25 mg of INT131 once per day for 48 weeks, the second group receives 2 mg of INT131 once per day for 48 weeks, and the third group receives a placebo once per day for 48 weeks. In another example, the study could be terminated at the 24 week time point. In yet another example, the study would last up to 72 weeks. At the beginning of the trial (i.e. week 0) and at least weeks 4, 12, 24, 48 and 50 and up to 10 total visits, each of the at least 225 subjects are tested for changes in NAS, steatosis grade (via fatty liver index, "FLI"), portal and lobular inflammation grade, ballooning grade and fibrosis stage (via NAFLD fibrosis score), as described by Kleiner et al., Design and validation of a histological scoring system for nonalcoholic fatty liver disease, *Hepatology* 2005, 41(6), 1313-21. Each of the 300 subjects are also tested for changes in 1) anthropometric characteristics (i.e. weight, BMI, waist and hip circumference); 2) liver function tests (i.e. aspartate aminotransferase (AST), alkaline aminotransferase (ALT), gamma-glutamyl transpeptidase (GGT), alkaline phosphatase (ALP), creatinine phosphokinase (CPK), and total and direct bilirubin); 3) serum lipid profile (i.e. total cholesterol, triglycerides, and high-density lipoprotein cholesterol); 4) insulin resistance (via oral glucose tolerance test "OGTT" and/or homeostatic model of assessment-insulin resistance, "HOMA-IR"); 5) adipokines (i.e. leptin, adiponectin and vaspin), markers of liver function (such as fetuin and irisin); 6) results of nuclear magnetic resonance spectroscopy ("NMR-spec") of liver; 7) bone density and body fat mass and distribution via dual-energy x-ray absorptiometry (DEXA) at all or some of the above time points as indicated; 8) high sensitivity C reactive protein ("hCRP"); liver fibrosis markers ELF™ (such as hyaluronic acid ("HA"), procollagen III amino terminal peptidase ("PII-INP"), and metalloproteinase 1 tissue inhibitor ("TIMP-1"); and bone markers (such as procollagen type 1 aminoterminal propeptide ("P1NP") and osteocalcin). Patient will undergo liver biopsies at screening and at Week 9 and Week 48. Pharmacokinetic ("PK") samples will be collected at baseline and at Week 9, Week 28 and Week 48. Pharmacodynamic ("PD") samples will be collected at baseline and at Week 9 and Week 48.

The following tasks will be completed on Day 1 (1) perform an abbreviated physical examination including vital signs, weight, height, waist and hip circumference; (2) medical history review; (3) obtain fasting morning blood and urine samples for safety labs including serum lipid profile and liver function tests; (4) obtain blood samples for PK analyses; (5) obtain blood samples for PD analyses; (5) perform liver biopsy if not performed in last two weeks; (5) for woman of child bearing potential perform urine pregnancy test; (6) concomitant medication review; (7) document any serious adverse events since signing of informed consent; (8) dispense study medication.

The following tasks will be completed during Week 5: (1) perform an abbreviated physical examination including vital signs, weight, height, waist and hip circumference; (2) obtain fasting morning blood and urine samples for safety labs including serum lipid profile and liver function tests; (3) concomitant medication review; (4) record all adverse events and (5) record returned study medication and dispense study medication.

The following tasks will be completed during Week 9: (1) perform an abbreviated physical examination including vital signs, weight, height, waist and hip circumference; (2) obtain fasting morning blood and urine samples for safety labs including serum lipid profile and liver function tests; (3) obtain blood samples for PK analyses; (4) obtain blood samples for PD analyses; (5) concomitant medication review; (6) record all adverse events; and (7) record returned study medication and dispense study medication.

The following tasks will be completed during Weeks 17, 23, 28, 35, and 41: (1) perform an abbreviated physical examination including vital signs, weight, height, waist and hip circumference; (2) obtain fasting morning blood and urine samples for safety labs including serum lipid profile and liver function tests; (3) obtain blood samples for PK analyses; (4) obtain blood samples for PD analyses at week 28 only; (5) record all adverse events; (6) record returned study medication and dispense study medication.

The following tasks will be completed during Week 48 or Early Termination Visit: (1) perform an abbreviated physical examination including vital signs, weight, height, waist and hip circumference; (2) obtain fasting morning blood and urine samples for safety labs including serum lipid profile and liver function tests; (3) obtain blood samples for PK analyses; (4) obtain blood samples for PD analyses; (5) obtain ultrasound guided liver biopsy after collection of blood samples. To be done after collection of all blood samples; (6) calculate NFS; (7) concomitant medication review; (8) record all adverse events and (9) record returned study medication. Sufficient data will also be collected during all time points to calculate the indexes outlined below.

Endpoints

The primary endpoint of the study will be a 2 point reduction NAS steatosis (part of NAS) grade at week 48 compared to baseline. The secondary endpoints of the study will include: (1) change in NAS steatosis grade at week 9 compared to baseline; (2) change in hepatic histology as assessed by NAS at week 9 and week 48 compared to baseline: (3) changes in NAFLD fibrosis score (NFS) at week 9 and 48 compared to baseline; (4) changes in Fatty liver index (FLI) at week 9 and 48 compared to baseline; (5) changes in BMI and waist to hip ratio at Week 9 and 48 compared to baseline; and (6) changes from baseline in the following parameters will be evaluated at weeks 9 and 48: (i) liver function tests including γ-glutamyl transferase (GGT); (ii) high sensitivity CRP; (iii) serum lipid profile; (iv) insulin resistance; (v) adiponectin; (vi) liver fibrosis biomarker via ELF: HA, PIIINP, and TIMP-1; and (vii) bone markers: P1NP and Osteocalcin.

Safety

All patients will be provided with a diet and mild aerobic exercise routine. Blood and urine samples for safety labs will be collected at screening and at Week 9 and Week 48 or more frequently if warranted. Safety endpoints will include: (1) monitoring treatment emergent adverse events; (2) valuation of subject discontinuation and withdrawal information; (3) assessment of changes in safety laboratory parameters, including hematology, clinical chemistry, pregnancy tests and (4) assessment of changes in vital signs, physical examination and electrocardiogram findings.

Methods

BMI is calculated by the formula: body weight (kg)/height$^2$ (m$^2$).

HOMA-IR is calculated by the formula: glucose (mmol/L)×insulin (μU/mL)/22.5.

NAFLD fibrosis score is calculated by the formula: $-1.675+0.037*$age (years)$+0.094*$BMI (kg/m$^2$)$+1.13*$IFG (impaired fasting glucose)/diabetes mellitus (yes=1, no=0)$+0.99*$AST/ALT ratio$-0.013*$platelet ($*10^9$/L)$-0.66*$albumin (g/dL).

FLI is calculated by the formula: $(e^{0.953*Log\ e(triglycerides)+0.139*BMI+0.718*Log\ e(GGT)+0.053*(waist\ circumference)-15.745})/(1+e^{0.953*Log\ e(triglycerides)+0.139*BMI+0.718*Log\ e(GGT)+0.053*(waist\ circumference)-15.745})*100$.

Insulin sensitivity will be quantified by the quantitative insulin sensitivity check index (QUICKI) using the formula: QUICKI=1/[log(glucose) (mg/dL)+log(insulin) (U/mL)]

NAS is calculated by the unweighted sum of the scores for steatosis, lobular inflammation and ballooning, which are determined via liver biopsy. Steatosis is scored from 0 to 3 wherein 0 indicates less than 5% of hepatocytes contain abnormal fat accumulation, 1 indicates 5-33%, 2 indicates 34-66% and 3 indicates more than 66%. Lobular inflammation is scored from 0 to 3 wherein 0 indicates no inflammation, 1 indicates less than two, 2 indicates from 2 to 4 and 3 indicates more than 4. Ballooning is scored from 0 to 2 wherein 0 indicates no hepatocyte ballooning, 1 indicates few ballooned hepatocytes and 2 indicates many ballooned hepatocytes. Thus, the total for NAS ranges from 0 to 8. For more detail see Kleiner et al., Design and validation of a histological scoring system for nonalcoholic fatty liver disease, *Hepatology* 2005, 41(6), 1313-21 and LaBrecque D, et al., (ed.) World Gastroenterology Organisation Global Guidelines: Nonalcoholic fatty liver disease and nonalcoholic steatohepatitis, 2012, Jun., 1-29 available at http:// www.worldgastroenterology.org/NAFLD-NASH.html, each of which is incorporated herein by reference in its entirety.

NMR-spec is conducted under the following conditions: 1H-MRS is used to calculate the precise fat content of the liver. Single-voxel MR spectra will be acquired in a 3T MRI Scanner with the integrated body coil using a point-resolved spectroscopy (PRESS) technique and local shimming. Voxels (size 20×20×20 mm$^3$) will be placed in the right liver lobe (segment VII) trying to avoid bile ducts and larger vessels. Scans will be acquired during a matter of seconds while participants are holding their breath to avoid artifacts. TR=3,500 ms, TE=25 ms, 512 data points, bandwidth, BW=1,000 Hz/pixel, without water suppression.

Results

Subjects receiving either 1.25 or 2 mg of INT131 have a reduction in their NAS, steatosis grade, portal and lobular inflammation grade, ballooning grade and/or fibrosis stage when comparing week 0 to week 48, which is statistically significant versus the placebo group. Subjects receiving either 1.25 or 2 mg of INT131 also have an improvement in their liver function test(s) as well as most if not all other metabolic parameters outlined above.

What is claimed is:

1. A method of treating nonalcoholic steatohepatitis (NASH) comprising administering to a subject in need thereof a therapeutically effective amount of a compound of formula (I), or a pharmaceutically acceptable salt thereof;

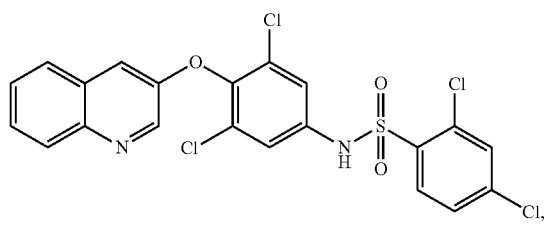

(I)

wherein the compound of formula (I), or a pharmaceutically acceptable salt thereof is administered orally.

2. The method of claim 1, wherein the subject is a human.

3. The method of claim 1, wherein the NASH is NASH with attendant liver fibrosis.

4. The method of claim 1, wherein the NASH is NASH with attendant liver cirrhosis.

5. The method of claim 1, wherein the amount of formula (I), or a pharmaceutically acceptable salt thereof, is from about 0.1 to about 10.0 mg per day.

6. The method of claim 5, wherein the amount of formula (I), or a pharmaceutically acceptable salt thereof, is from about 0.1 to about 5.0 mg per day.

7. The method of claim 6, wherein the amount of formula (I), or a pharmaceutically acceptable salt thereof, is about 1 mg per day.

8. The method of claim 6, wherein the amount of formula (I), or a pharmaceutically acceptable salt thereof, is about 1.5 mg per day.

9. The method of claim 6, wherein the amount of formula (I), or a pharmaceutically acceptable salt thereof, is about 2 mg per day.

10. The method of claim 6, wherein the amount of formula (I), or a pharmaceutically acceptable salt thereof, is about 3 mg per day.

11. The method of claim 1, wherein the compound of the formula (I) is administered as a pharmaceutically acceptable salt.

12. The method of claim 11, wherein the amount of the pharmaceutically acceptable salt of formula (I) is from about 0.1 to about 10.0 mg per day.

13. The method of claim 12, wherein the amount of the pharmaceutically acceptable salt of formula (I) is from about 0.1 to about 5.0 mg per day.

14. The method of claim 13, wherein the amount of the pharmaceutically acceptable salt of formula (I) is about 1 mg per day.

15. The method of claim 13, wherein the amount of the pharmaceutically acceptable salt of formula (I) is about 1.5 mg per day.

16. The method of claim 13, wherein the amount of the pharmaceutically acceptable salt of formula (I) is about 2 mg per day.

17. The method of claim 13, wherein the amount of the pharmaceutically acceptable salt of formula (I) is about 3 mg per day.

18. The method of claim 11, wherein the pharmaceutically acceptable salt of the compound of formula (I) is the besylate salt.

19. The method of claim 18, wherein the amount of the besylate salt of the compound of formula (I), is equivalent to from about 0.1 mg to about 10.0 mg of the free base.

20. The method of claim 19, wherein the amount of the besylate salt of the compound of formula (I), is equivalent to from about 0.5 mg to about 5.0 mg of the free base.

21. The method of claim 20, wherein the amount of the besylate salt of the compound of formula (I), is equivalent to about 1 mg of the free base.

22. The method of claim 20, wherein the amount of the besylate salt of the compound of formula (I), is equivalent to about 1.5 mg of the free base.

23. The method of claim 20, wherein the amount of the besylate salt of the compound of formula (I), is equivalent to about 2 mg of the free base.

24. The method of claim 20, wherein the amount of the besylate salt of the compound of formula (I), is equivalent to about 3 mg of the free base.

25. The method of claim 1, wherein the method provides an NAFLD activity score (NAS) of 7 or less.

26. The method of claim 25 wherein the NAS is 5 or less.

27. The method of claim 25 wherein the NAS is 3 or less.

* * * * *